United States Patent
Sabatini et al.

(10) Patent No.: US 10,168,338 B2
(45) Date of Patent: Jan. 1, 2019

(54) METHODS OF IDENTIFYING MODULATORS OF SESTRIN-GATOR-2 INTERACTION FOR MODULATING MTORC1 ACTIVITY

(71) Applicant: Whitehead Institute for Biomedical Research, Cambridge, MA (US)

(72) Inventors: David M. Sabatini, Cambridge, MA (US); Lynne Chantranupong, Cambridge, MA (US); Rachel L. Wolfson, Cambridge, MA (US); Jose Orozco, Boston, MA (US); Robert A. Saxton, Cambridge, MA (US); Shomit Sengupta, Belmont, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 15/511,007

(22) PCT Filed: Sep. 11, 2015

(86) PCT No.: PCT/US2015/049727
§ 371 (c)(1),
(2) Date: Mar. 13, 2017

(87) PCT Pub. No.: WO2016/040824
PCT Pub. Date: Mar. 17, 2016

(65) Prior Publication Data
US 2017/0285043 A1 Oct. 5, 2017

Related U.S. Application Data

(60) Provisional application No. 62/049,922, filed on Sep. 12, 2014, provisional application No. 62/155,795, filed on May 1, 2015.

(51) Int. Cl.
*G01N 33/50* (2006.01)
*G01N 33/53* (2006.01)
*G01N 33/68* (2006.01)

(52) U.S. Cl.
CPC ..... *G01N 33/6872* (2013.01); *G01N 33/5041* (2013.01); *G01N 33/53* (2013.01); *G01N 2500/02* (2013.01)

(58) Field of Classification Search
None
See application file for complete search history.

(56) References Cited

U.S. PATENT DOCUMENTS

| | | |
|---|---|---|
| 2014/0249045 A1 | 9/2014 | Kim et al. |
| 2017/0027897 A1 | 2/2017 | Sabatini et al. |
| 2017/0082633 A1 | 3/2017 | Sabatini et al. |

FOREIGN PATENT DOCUMENTS

| | | |
|---|---|---|
| WO | WO 2013/043012 A2 | 3/2013 |
| WO | WO 2013/053919 A2 | 4/2013 |
| WO | WO 2014/153118 A1 | 9/2014 |
| WO | WO 2015/061607 A1 | 4/2015 |
| WO | WO 2015/168617 | 11/2015 |
| WO | WO2015/173398 | 11/2015 |
| WO | WO 2016/040824 | 3/2016 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Ben-Sahra, I., et al. "Sestrin2 integrates Akt and mTOR signaling to protect cells against energetic stress-induced death." *Cell Death & Differentiation*, Dec. 14, 2013, vol. 20, pp. 611-619.
Bar-Peled, Liron, et al. "A Tumor suppressor complex with GAP activity for the Rag GTPases that signal amino acid sufficiency to mTORC1." *Science*, May 31, 2013, vol. 340, No. 6136, pp. 1100-1106.
Parkhitko, A. A., et al, "Kinase mTOR: regulation and role in maintenance of cellular homeostasis, tumor development, and aging." *Biochemistry (Moscow)*, Feb. 2014, vol. 79, No. 2, pp. 88-101.
Chantranupong, Lynne, et al. "The Sestrins interact with GATOR2 to negatively regulate the amino-acid-sensing pathway upstream of mTORC1." *Cell Reports*, Sep. 14, 2014, vol. 9, pp. 1-8.
Parmigiani, Anita, et al. "Sestrins inhibit mTORC1 kinase activation through the GATOR complex." *Cell Reports*, Oct. 19, 2014, vol. 9, pp. 1281-1291.
Kim, Jeong Sig, et al. "Sestrin2 inhibits mTORC1 through modulation of GATOR complexes." *Scientific Reports*,Mar. 30, 2015, vol. 5 pp. 1-10.
International Search Report and Written Opinion for International Application No. PCT/US2015/049727, dated Apr. 11, 2016.
Bar-Peled, Liron, and David M. Sabatini. "Regulation of mTORC1 by amino acids." *Trends in cell biology* 24.7 (2014): 400-406.
Wang, Shuyu, et al. "Lysosomal amino acid transporter SLC38A9 signals arginine sufficiency to mTORC1." *Science* 347.6218 (2015): 188-194.
Jewell, Jenna L., et al. "Differential regulation of mTORC1 by leucine and glutamine." Science 347.6218 (2015): 194-198.
Rebsamen, Manuele, et al. "SLC38A9 is a component of the lysosomal amino acid sensing machinery that controls mTORC1." Nature 519.7544 (2015): 477-481.
Sabatini, David M., Abstract "Cell Growth Signaling in Cancer Development," National Institutes of Health Grant No. R01 CA129105-01A1, funded on Apr. 8, 2008, through R01 CA129105-09, funded on Jan. 27, 2016.

(Continued)

*Primary Examiner* — Christine J Saoud
*Assistant Examiner* — Jon M Lockard
(74) *Attorney, Agent, or Firm* — Lisa M. Warren, Esq.; Morse, Barnes-Brown & Pendleton, P.C.

(57) ABSTRACT

The present invention provides methods of identifying modulators of mTORC1 based upon their effect on GATOR2-Sestrin binding or Sestrin-leucine binding; and the use of such modulators to alter mTORC1 activity in a cell and to treat disease and conditions that are effected by mTORC1 activity.

12 Claims, 36 Drawing Sheets
Specification includes a Sequence Listing.

(56) References Cited

OTHER PUBLICATIONS

Sabatini, David M., Abstract "Regulation of the MTOR Growth Pathway by Nutrients," National Institutes of Health Grant No. R01 CA103866-01, funded on Mar. 23, 2004, through R01 CA103866-13, funded on May 20, 2016.

Sabatini, David M., Abstract "Translational Control by Rapamycinsensitive Signaling," National Institutes of Health Grant No. R01 AI047389-01, funded on Apr. 1, 2000, through R37 AI047389-17, funded on Apr. 21, 2016.

Maiese, Kenneth, et al. "mTOR: on target for novel therapeutic strategies in the nervous system." *Trends in molecular medicine* 19.1 (2013): 51-60.

Lamming, Dudley W., et al. "Rapalogs and mTOR inhibitors as anti-aging therapeutics." *The Journal of clinical investigation* 123.3 (2013): 980-989.

Kitada, Munehiro, et al., "Nutrient Sensing and Regulation of Cellular Functions," Kagaku to seibutsu (*Chemistry and Biology*), 2013, vol. 51, pp. 294-301.

International Search Report and Written Opinion issued in International Application No. PCT/US2015/028885, dated Nov. 2, 2015.

Extended European Search Report in Application No. EP 15 78 6697 dated Aug. 9, 2017.

Extended European Search Report in Application No. EP 15840018.4, dated Jan. 24, 2018.

Non-Final Office Action in U.S. Appl. No. 15/308,605 dated Feb. 26, 2018.

Notice of Allowance and Fee(s) Due in U.S. Appl. No. 15/308,605, dated Jun. 27, 2018.

\* cited by examiner

FIGS. 9D - 9E

SEQ ID NO:1 - gi|7657437|ref|NP_055269.1| sestrin-1 isoform 1 [Homo sapiens]

MAEGENEVRWDGLCSRDSTTRETALENIRQTILRKTEYLRSVKETPHRPSDGLSNTESSDGLNKLLAHLL

MLSKRCPFKDVREKSEFILKSIQELGIRIPRPLGQGPSRFIPEKEILQVGSEDAQMHALFADSFAALGRL

DNITLVMVFHPQYLESFLKTQHYLLQMDGPLPLHYRHYIGIMAAARHQCSYLVNLHVNDFLHVGGDPKWL

NGLENAPQKLQNLGELNKVLAHRPWLITKEHIEGLLKAEEHSWSLAELVHAVVLLTHYHSLASFTFGCGI

SPEIHCDGGHTFRPPSVSNYCICDITNGNHSVDEMPVNSAENVSVSDSFFEVEALMEKMRQLQECRDEEE

ASQEEMASRFEIEKRESMFVFSSDDEEVTPARAVSRHFEDTSYGYKDFSRHGMHVPTFRVQDYCWEDHGY

SLVNRLYPDVGQIIDEKFHIAYNLTYNTMAMHKDVDTSMLRRAIWNYIHCMFGIRYDDYDYGEINQLLDR

SFKVYIKTVVCTPEKVTKRMYDSFWRQFKHSEKVHVNLLLIEARMQAELLYALRAITRYMT

FIG. 17A

SEQ ID NO:9 - gi|315709500|ref|NP_001186862.1| sestrin-1 isoform 2 [Homo sapiens]

MRLAAAANEAYTAPLAVSGLLGCKQCGGGRDQDEELGIRIPRPLGQGPSRFIPEKEILQVGSEDAQMHAL

FADSFAALGRLDNITLVMVFHPQYLESFLKTQHYLLQMDGPLPLHYRHYIGIMAAARHQCSYLVNLHVND

FLHVGGDPKWLNGLENAPQKLQNLGELNKVLAHRPWLITKEHIEGLLKAEEHSWSLAELVHAVVLLTHYH

SLASFTFGCGISPEIHCDGGHTFRPPSVSNYCICDITNGNHSVDEMPVNSAENVSVSDSFFEVEALMEKM

RQLQECRDEEEASQEEMASRFEIEKRESMFVFSSDDEEVTPARAVSRHFEDTSYGYKDFSRHGMHVPTFR

VQDYCWEDHGYSLVNRLYPDVGQLIDEKFHIAYNLTYNTMAMHKDVDTSMLRRAIWNYIHCMFGIRYDDY

DYGEINQLLDRSFKVYIKTVVCTPEKVTKRMYDSFWRQFKHSEKVHVNLLLIEARMQAELLYALRAITRY

SEQ ID NO:10 - gi|315709502|ref|NP_001186863.1| sestrin-1 isoform 3 [Homo sapiens]

MHALFADSFAALGRLDNITLVMVFHPQYLESFLKTQHYLLQMDGPLPLHYRHYIGIMAAARHQCSYLVNL

HVNDFLHVGGDPKWLNGLENAPQKLQNLGELNKVLAHRPWLITKEHIEGLLKAEEHSWSLAELVHAVVLL

THYHSLASFTFGCGISPEIHCDGGHTFRPPSVSNYCICDITNGNHSVDEMPVNSAENVSVSDSFFEVEAL

MEKMRQLQECRDEEEASQEEMASRFEIEKRESMFVFSSDDEEVTPARAVSRHFEDTSYGYKDFSRHGMHV

PTFRVQDYCWEDHGYSLVNRLYPDVGQLIDEKFHIAYNLTYNTMAMHKDVDTSMLRRAIWNYIHCMFGIR

YDDYDYGEINQLLDRSFKVYIKTVVCTPEKVTKRMYDSFWRQFKHSEKVHVNLLLIEARMQAELLYALRA

ITRYMT

FIG. 17C

SEQ ID NO:2 -gi|13899299|ref|NP_113647.1| sestrin-2 [Homo sapiens]

MIVADSECRAELKDYLRFAPGGVGDSGPGEEQRESRARRGPRGPSAFIPVEEVLREGAESLEQHLGLEAL

MSSGRVDNLAVVMGLHPDYFTSFWRLHYLLLHTDGPLASSWRHYIAIMAAARHQCSYLVGSHMAEFLQTG

GDPEWLLGLHRAPEKLRKLSEINKLLAHRPWLITKEHIQALLKTGEHTWSLAELIQALVLLTHCHSLSSF

VFGCGILPEGDADGSPAPQAPTPPSEQSSPPSRDPLNNSGGFESARDVEALMERMQQLQESLLRDEGTSQ

EEMESRFELEKSESLLVTPSADILEPSPHPDMLCFVEDPTFGYEDFTRRGAQAPPTFRAQDYTWEDHGYS

LIQRLYPEGGQLLDEKFQAAYSLTYNTIAMHSGVDTSVLRRAIWNYIHCVFGIRYDDYDYGEVNQLLERN

LKVYIKTVACYPEKTTRRMYNLFWRHFRHSEKVHVNLLLLEARMQAALLYALRAITRYMT

FIG. 17D

SEQ ID NO:3 -gi|31377591|ref|NP_653266.2| sestrin-3 isoform 1 [Homo sapiens]

MNRGGGSPSAAANYLLCTNCRKVLRKDKRIRVSQPLTRGPSAFIPEKEVVQANTVDERTNFLVEEYSTSG
RLDNITQVMSLHTQYLESFLRSQFYMLRMDGPLPLPYRHYIAIMAAARHQCSYLINMHVDEFLKTGGIAE
WLNGLEYVPQRLKNLNEINKLLAHRPWLITKEHIQKLVKTGENNWSLPELVHAVVLLAHYHALASFVFGS
GINPERDPEISNGFRLISVNNFCVCDLANDNNIENASLSGSNFGIVDSLSELEALMERMKRLQEEREDEE
ASQEEMSTRFEKEKKESLFVVSGDTFHSFPHSDFEDDMIITSDVSRYIEDPGFGYEDFARRGEEHLPTFR
AQDYTWENHGFSLVNRLYSDIGHLLDEKFRMVYNLTYNTMATHEDVDTTMLRRALFNYVHCMFGIRYDDY
DYGEVNQLLERSLKVYIKTVTCYPERTTKRMYDSYWRQFKHSEKVHVNLLLMEARMQAELLYALRAITRH
LT

FIG. 17E

SEQ ID NO:11 -gi|409971404|ref|NP_001258523.1| sestrin-3 isoform 2 [Homo sapiens]

MSLHTQYLESFLRSQFYMLRMDGPLPLPYRHYIAIMKLVKTGENNWSLPELVHAVVLLAHYHALASFVFG

SGINPERDPEISNGFRLISVNNFCVCDLANDNNIENASLSGSNFGIVDSLSELEALMERMKRLQEEREDE

EASQEEMSTRFEKEKKESLFVVSGDTFHSFPHSDFEDDMIITSDVSRYIEDPGFGYEDFARRGEEHLPTF

RAQDYTWENHGFSLVNRLYSDIGHLLDEKFRMVYNLTYNTMATHEDVDTTMLRRALFNYVHCMFGIRYDD

YDYGEVNQLLERSLKVYIKTVTCYPERTTKRMYDSYWRQFKHSEKVHVNLLLMEARMQAELLYALRAITR

HLT

FIG. 17F

SEQ ID NO:4 -sp|Q9NXC5|MIO_HUMAN WD repeat-containing protein mio OS=Homo sapiens GN=MIOS PE=1 SV=2

MSGTKPDILWAPHHVDRFVVCDSELSLYHVESTVNSELKAGSLRLSEDSAATLLSINSDT

PYMKCVAWYLNYDPECLLAVGQANGRVVLTSLGQDHNSKFKDLIGKEFVPKHARQCNTLA

WNPLDSNWLAAGLDKHRADFSVLIWDICSKYTPDIVPMEKVKLSAGETETTLLVTKPLYE

LGQNDACLSLCWLPRDQKLLLAGMHRNLAIFDLRNTSQKMFVNTKAVQGVTVDPYFHDRV

ASFYEGQVAIWDLRKFEKPVLTLTEQPKPLTKVAWCPTRTGLLATLTRDSNIIRLYDMQH

TPTPIGDETEPTIIERSVQPCDNYIASFAWHPTSQNRMIVVTPNRTMSDFTVFERISLAW

SPITSLMWACGRHLYECTEEENONSLEKDIATKMRLRALSRYGLDTEQVWRNHILAGNED

PQLKSLWYTLHFMKQYTEDMDQKSPGNKGSLVYAGIKSIVKSSLGMVESSRHNWSGLDKQ

SDIQNLNEERILALQLCGWIKKGTDVDVGPFLNSLVQEGEWERAAAVALFNLDIRRAIQI

LNEGASSEKGDLNLNVVAMALSGYTDEKNSLWREMCSTLRLQLNNPYLCVMFAFLTSETG

SYDGVLYENKVAVRDRVAFACKFLSDTQLNRYIEKLTNEMKEAGNLEGILLTGLTKDGVD

LMESYVDRTGDVQTASYCMLQGSPLDVLKDERVQYWIENYRNLLDAWRFWHKRAEFDIHR

SKLDPSSKPLAQVFVSCNFCGKSISYSCSAVPHQGRGFSQYGVSGSPTKSKVTSCPGCRK

PLPRCALCLINMGTPVSSCPGGTKSDEKVDLSKDKKLAQFNNWFTWCHNCRHGGHAGHML

SWFRDHAECPVSACTCKCMQLDTTGNLVPAETVQP

FIG. 17G

SEQ ID NO:5 -sp|P55735|SEC13_HUMAN Protein SEC13 homolog OS=Homo sapiens GN=SEC13 PE=1 SV=3

MVSVINTVDTSHEDMIHDAQMDYYGTRLATCSSDRSVKIFDVRNGGQILIADLRGHEGPV

WQVAWAHPMYGNILASCSYDRKVIIWREENGTWEKSHEHAGHDSSVNSVCWAPHDYGLIL

ACGSSDGAISLLTYTGEGQWEVKKINNAHTIGCNAVSWAPAVVPGSLIDHPSGQKPNYIK

RFASGGCDNLIKLWKEEEDGQWKEEQKLEAHSDWVRDVAWAPSIGLPTSTIASCSQDGRV

FIWTCDDASSNTWSPKLLHKFNDVVWHVSWSITANILAVSGGDNKVTLWKESVDGQWVCI

SDVNKGQGSVSASVTEGQQNEQ

FIG. 17H

SEQ ID NO:6 -sp|Q96S15|WDR24_HUMAN WD repeat-containing protein 24 OS=Homo sapiens GN=WDR24 PE=1 SV=1

MGKKRTTSGEGRERQRLPARRFRTTSPAALRADSVDGGSLLAPLLGLTDRAFSDCPDLAD

GAMEKMSRVTTALGGSVLTGRTMHCHLDAPANAISVCRDAAQVVVAGRSIFKIYAIEEEQ

FVEKLNLRVGRKPSLNLSCADVVWHQMDENLLATAATNGVVVTWNLGRPSRNKQDQLFTE

HKRTVNKVCFHPTEAHVLLSGSQDGFMKCFDLRRKDSVSTFSGEATEAGPREWAMAGCVP

ILPVLSCRILRLHHSFAHGPMQDAESTANDARESWGCPLYPLGLCSGPQAGQSESVRDVQ

FSIRDYFTFASTFENGNVQLWDIRRPDRCERMFTAHNGPVFCCDWHPEDRGWLATGGRDK

MVKVWDMTTHRAKEMHCVQTIASVARVKWRPECRHHLATCSMMVDHNIYVWDVRRPFVPA

AMFEEHRDVTTGIAWRHPHDPSFLLSGSKDSSLCQHLFRDASQPVERANPEGLCYGLFGD

LAFAAKESLVAAESGRKPYTGDRRHPIFFKRKLDPAEPFAGLASSALSVFETEPGGGGMR

WFVDTAERYALAGRPLAELCDHNAKVARELGRNQVAQTWTMLRIIYCSPGLVPTANLNHS

VGKGGSCGLPLMNSFNLKDMAPGLGSETRLDRSKGDARSDTVLLDSSATLITNEDNEETE

GSDVPADYLLGDVEGEEDELYLLDPEHAHPEDPECVLPQEAFPLRHEIVDTPPGPEHLQD

KADSPHVSGSEADVASLAPVDSSFSLLSVSHALYDSRLPPDFFGVLVRDMLHFYAEQGDV

QMAVSVLIVLGERVRKDIDEQTQEHWYTSYIDLLQRFRLWNVSNEVVKLSTSRAVSCLNQ

ASTTLHVNCSHCKRPMSSRGWVCDRCHRCASMCAVCHHVVKGLFVWCQGCSHGGHLQHIM

KWLEGSSHCPAGCGHLCEYS

FIG. 17I

SEQ ID NO:7 -sp|Q6PJI9|WDR59_HUMAN WD repeat-containing protein 59 OS=Homo sapiens
GN=WDR59 PE=1 SV=2

MAARWSSENVVVEFRDSQATAMSVDCLGQHAVLSGRRFLYIVNLDAPFEGHRKISRQSKW

DIGAVQWNPHDSFAHYFAASSNQRVDLYKWKDGSGEVGTTLQGHTRVISDLDWAVFEPDL

LVTSSVDTYIYIWDIKDTRKPTVALSAVAGASQVKWNKKNANCLATSHDGDVRIWDKRKP

STAVEYLAAHLSKIHGLDWHPDSEHILATSSQDNSVKFWDYRQPRKYLNILPCQVPVWKA

RYTPFSNGLVTVMVPQLRRENSLLLWNVFDLNTPVHTFVGHDDVVLEFQWRKQKEGSKDY

QLVTWSRDQTLRMWRVDSQMQRLCANDILDGVDEFIESISLLPEPEKTLHTEDTDHQHTA

SHGEEEALKEDPPRNLLEERKSDQLGLPQTLQQEFSLINVQIRNVNVEMDAADRSCTVSV

HCSNHRVKMLVKFPAQYPNNAAPSFQFINPTTITSTMKAKLLKILKDTALQKVKRGQSCL

EPCLRQLVSCLESFVNQEDSASSNPFALPNSVTPPLPTFARVTTAYGSYQDANIPFPRTS

GARFCGAGYLVYFTRPMTMHRAVSPTEPTPRSLSALSAYHTGLIAPMKIRTEAPGNLRLY

SGSPTRSEKEQVSISSFYYKERKSRRWKSKREGSDSGNRQIKAAGKVIIQDIACLLPVHK

SLGELYILNVNDIQETCQKNAASALLVGRKDLVQVWSLATVATDLCLGPKSDPDLETPWA

RHPFGRQLLESLLAHYCRLRDVQTLAMLCSVFEAQSRPQGLPNPFGPFPNRSSNLVVSHS

RYPSFTSSGSCSSMSDPGLNTGGWNIAGREAEHLSSPWGESSPEELRFGSLTYSDPRERE

RDQHDKNKRLLDPANTQQFDDFKKCYGEILYRWGLREKRAEVLKFVSCPPDPHKGIEFGV

YCSHCRSEVRGTQCAICKGFTFQCAICHVAVRGSSNFCLTCGHGGHTSHMMEWFRTQEVC

PTGCGCHCLLESTF

FIG. 17J

SEQ ID NO:8 -sp|Q96EE3|SEH1_HUMAN Nucleoporin SEH1 OS=Homo sapiens GN=SEH1L PE=1 SV=3

MFVAKSIAADHKDLIHDVSFDFHGRRMATCSSDQSVKVWDKSESGDWHCTASWKTHSGSV

WRVTWAHPEFGQVLASCSFDRTAAVWEEIVGESNDKLRGQSHWVKRTTLVDSRTSVTDVK

FAPKHMGLMLATCSADGIVRIYEAPDVMNLSQWSLQHEISCKLSCSCISWNPSSSRAHSP

MIAVGSDDSSPNAMAKVQIFEYNENTRKYAKAETLMTVTDPVHDIAFAFNLGRSFHILAI

ATKDVRIFTLKPVRKELTSSGGPTKFEIHIVAQFDNHNSQVWRVSWNITGTVLASSGDDG

CVRLWKANYMDNWKCTGILKGNGSPVNGSSQQGTSNPSLGSTIPSLQNSLNGSSAGRKHS

FIG. 17K

SEQUENCE LISTING

<160> NUMBER OF SEQ ID NOS: 31

<210> SEQ ID NO 1
<211> LENGTH: 551
<212> TYPE: PRT
<213> ORGANISM: Homo sapiens

<400> SEQUENCE: 1

```
Met Ala Glu Gly Glu Asn Glu Val Arg Trp Asp Gly Leu Cys Ser Arg
1               5                   10                  15

Asp Ser Thr Thr Arg Glu Thr Ala Leu Glu Asn Ile Arg Gln Thr Ile
            20                  25                  30

Leu Arg Lys Thr Glu Tyr Leu Arg Ser Val Lys Glu Thr Pro His Arg
        35                  40                  45

Pro Ser Asp Gly Leu Ser Asn Thr Glu Ser Ser Asp Gly Leu Asn Lys
    50                  55                  60

Leu Leu Ala His Leu Leu Met Leu Ser Lys Arg Cys Pro Phe Lys Asp
65                  70                  75                  80

Val Arg Glu Lys Ser Glu Phe Ile Leu Lys Ser Ile Gln Glu Leu Gly
                85                  90                  95

Ile Arg Ile Pro Arg Pro Leu Gly Gln Gly Pro Ser Arg Phe Ile Pro
            100                 105                 110

Glu Lys Glu Ile Leu Gln Val Gly Ser Glu Asp Ala Gln Met His Ala
        115                 120                 125

Leu Phe Ala Asp Ser Phe Ala Ala Leu Gly Arg Leu Asp Asn Ile Thr
    130                 135                 140

Leu Val Met Val Phe His Pro Gln Tyr Leu Glu Ser Phe Leu Lys Thr
145                 150                 155                 160

Gln His Tyr Leu Leu Gln Met Asp Gly Pro Leu Pro Leu His Tyr Arg
                165                 170                 175

His Tyr Ile Gly Ile Met Ala Ala Ala Arg His Gln Cys Ser Tyr Leu
            180                 185                 190

Val Asn Leu His Val Asn Asp Phe Leu His Val Gly Gly Asp Pro Lys
        195                 200                 205

Trp Leu Asn Gly Leu Glu Asn Ala Pro Gln Lys Leu Gln Asn Leu Gly
    210                 215                 220

Glu Leu Asn Lys Val Leu Ala His Arg Pro Trp Leu Ile Thr Lys Glu
225                 230                 235                 240

His Ile Glu Gly Leu Leu Lys Ala Glu Glu His Ser Trp Ser Leu Ala
                245                 250                 255

Glu Leu Val His Ala Val Val Leu Leu Thr His Tyr His Ser Leu Ala
            260                 265                 270
```

```
Ser Phe Thr Phe Gly Cys Gly Ile Ser Pro Glu Ile His Cys Asp Gly
            275                 280                 285

Gly His Thr Phe Arg Pro Pro Ser Val Ser Asn Tyr Cys Ile Cys Asp
        290                 295                 300

Ile Thr Asn Gly Asn His Ser Val Asp Glu Met Pro Val Asn Ser Ala
305                 310                 315                 320

Glu Asn Val Ser Val Ser Asp Ser Phe Phe Glu Val Glu Ala Leu Met
                325                 330                 335

Glu Lys Met Arg Gln Leu Gln Glu Cys Arg Asp Glu Glu Glu Ala Ser
            340                 345                 350

Gln Glu Glu Met Ala Ser Arg Phe Glu Ile Glu Lys Arg Glu Ser Met
        355                 360                 365

Phe Val Phe Ser Ser Asp Asp Glu Glu Val Thr Pro Ala Arg Ala Val
    370                 375                 380

Ser Arg His Phe Glu Asp Thr Ser Tyr Gly Tyr Lys Asp Phe Ser Arg
385                 390                 395                 400

His Gly Met His Val Pro Thr Phe Arg Val Gln Asp Tyr Cys Trp Glu
                405                 410                 415

Asp His Gly Tyr Ser Leu Val Asn Arg Leu Tyr Pro Val Gly Gln
            420                 425                 430

Leu Ile Asp Glu Lys Phe His Ile Ala Tyr Asn Leu Thr Tyr Asn Thr
        435                 440                 445

Met Ala Met His Lys Asp Val Asp Thr Ser Met Leu Arg Arg Ala Ile
    450                 455                 460

Trp Asn Tyr Ile His Cys Met Phe Gly Ile Arg Tyr Asp Asp Tyr Asp
465                 470                 475                 480

Tyr Gly Glu Ile Asn Gln Leu Leu Asp Arg Ser Phe Lys Val Tyr Ile
                485                 490                 495

Lys Thr Val Val Cys Thr Pro Glu Lys Val Thr Lys Arg Met Tyr Asp
            500                 505                 510

Ser Phe Trp Arg Gln Phe Lys His Ser Glu Lys Val His Val Asn Leu
        515                 520                 525

Leu Leu Ile Glu Ala Arg Met Gln Ala Glu Leu Leu Tyr Ala Leu Arg
    530                 535                 540

Ala Ile Thr Arg Tyr Met Thr
545                 550

<210> SEQ ID NO 2
<211> LENGTH: 480
<212> TYPE: PRT
<213> ORGANISM: Homo sapiens

<400> SEQUENCE: 2

Met Ile Val Ala Asp Ser Glu Cys Arg Ala Glu Leu Lys Asp Tyr Leu
1               5                   10                  15

Arg Phe Ala Pro Gly Gly Val Gly Asp Ser Gly Pro Gly Glu Glu Gln
            20                  25                  30

Arg Glu Ser Arg Ala Arg Arg Gly Pro Arg Gly Pro Ser Ala Phe Ile
        35                  40                  45

Pro Val Glu Glu Val Leu Arg Glu Gly Ala Glu Ser Leu Glu Gln His
    50                  55                  60

Leu Gly Leu Glu Ala Leu Met Ser Ser Gly Arg Val Asp Asn Leu Ala
65                  70                  75                  80

Val Val Met Gly Leu His Pro Asp Tyr Phe Thr Ser Phe Trp Arg Leu
```

```
                 85                  90                  95
His Tyr Leu Leu Leu His Thr Asp Gly Pro Leu Ala Ser Ser Trp Arg
            100                 105                 110

His Tyr Ile Ala Ile Met Ala Ala Arg His Gln Cys Ser Tyr Leu
            115                 120                 125

Val Gly Ser His Met Ala Glu Phe Leu Gln Thr Gly Asp Pro Glu
            130                 135                 140

Trp Leu Leu Gly Leu His Arg Ala Pro Glu Lys Leu Arg Lys Leu Ser
145                 150                 155                 160

Glu Ile Asn Lys Leu Leu Ala His Arg Pro Trp Leu Ile Thr Lys Glu
            165                 170                 175

His Ile Gln Ala Leu Leu Lys Thr Gly Glu His Thr Trp Ser Leu Ala
            180                 185                 190

Glu Leu Ile Gln Ala Leu Val Leu Leu Thr His Cys His Ser Leu Ser
            195                 200                 205

Ser Phe Val Phe Gly Cys Gly Ile Leu Pro Glu Gly Asp Ala Asp Gly
            210                 215                 220

Ser Pro Ala Pro Gln Ala Pro Thr Pro Pro Ser Glu Gln Ser Ser Pro
225                 230                 235                 240

Pro Ser Arg Asp Pro Leu Asn Asn Ser Gly Gly Phe Glu Ser Ala Arg
            245                 250                 255

Asp Val Glu Ala Leu Met Glu Arg Met Gln Gln Leu Gln Glu Ser Leu
            260                 265                 270

Leu Arg Asp Glu Gly Thr Ser Gln Glu Glu Met Glu Ser Arg Phe Glu
            275                 280                 285

Leu Glu Lys Ser Glu Ser Leu Leu Val Thr Pro Ser Ala Asp Ile Leu
            290                 295                 300

Glu Pro Ser Pro His Pro Asp Met Leu Cys Phe Val Glu Asp Pro Thr
305                 310                 315                 320

Phe Gly Tyr Glu Asp Phe Thr Arg Arg Gly Ala Gln Ala Pro Pro Thr
            325                 330                 335

Phe Arg Ala Gln Asp Tyr Thr Trp Glu Asp His Gly Tyr Ser Leu Ile
            340                 345                 350

Gln Arg Leu Tyr Pro Glu Gly Gly Gln Leu Leu Asp Glu Lys Phe Gln
            355                 360                 365

Ala Ala Tyr Ser Leu Thr Tyr Asn Thr Ile Ala Met His Ser Gly Val
            370                 375                 380

Asp Thr Ser Val Leu Arg Arg Ala Ile Trp Asn Tyr Ile His Cys Val
385                 390                 395                 400

Phe Gly Ile Arg Tyr Asp Asp Tyr Asp Tyr Gly Glu Val Asn Gln Leu
            405                 410                 415

Leu Glu Arg Asn Leu Lys Val Tyr Ile Lys Thr Val Ala Cys Tyr Pro
            420                 425                 430

Glu Lys Thr Thr Arg Arg Met Tyr Asn Leu Phe Trp Arg His Phe Arg
            435                 440                 445

His Ser Glu Lys Val His Val Asn Leu Leu Leu Glu Ala Arg Met
            450                 455                 460

Gln Ala Ala Leu Leu Tyr Ala Leu Arg Ala Ile Thr Arg Tyr Met Thr
465                 470                 475                 480

<210> SEQ ID NO 3
<211> LENGTH: 492
<212> TYPE: PRT
<213> ORGANISM: Homo sapiens
```

```
<400> SEQUENCE: 3

Met Asn Arg Gly Gly Ser Pro Ser Ala Ala Asn Tyr Leu Leu
1               5                   10                  15

Cys Thr Asn Cys Arg Lys Val Leu Arg Lys Asp Lys Arg Ile Arg Val
                20                  25                  30

Ser Gln Pro Leu Thr Arg Gly Pro Ser Ala Phe Ile Pro Glu Lys Glu
            35                  40                  45

Val Val Gln Ala Asn Thr Val Asp Glu Arg Thr Asn Phe Leu Val Glu
    50                  55                  60

Glu Tyr Ser Thr Ser Gly Arg Leu Asp Asn Ile Thr Gln Val Met Ser
65                  70                  75                  80

Leu His Thr Gln Tyr Leu Glu Ser Phe Leu Arg Ser Gln Phe Tyr Met
                85                  90                  95

Leu Arg Met Asp Gly Pro Leu Pro Leu Pro Tyr Arg His Tyr Ile Ala
            100                 105                 110

Ile Met Ala Ala Ala Arg His Gln Cys Ser Tyr Leu Ile Asn Met His
        115                 120                 125

Val Asp Glu Phe Leu Lys Thr Gly Gly Ile Ala Glu Trp Leu Asn Gly
    130                 135                 140

Leu Glu Tyr Val Pro Gln Arg Leu Lys Asn Leu Asn Glu Ile Asn Lys
145                 150                 155                 160

Leu Leu Ala His Arg Pro Trp Leu Ile Thr Lys Glu His Ile Gln Lys
                165                 170                 175

Leu Val Lys Thr Gly Glu Asn Asn Trp Ser Leu Pro Glu Leu Val His
            180                 185                 190

Ala Val Val Leu Leu Ala His Tyr His Ala Leu Ala Ser Phe Val Phe
    195                 200                 205

Gly Ser Gly Ile Asn Pro Glu Arg Asp Pro Glu Ile Ser Asn Gly Phe
210                 215                 220

Arg Leu Ile Ser Val Asn Asn Phe Cys Val Cys Asp Leu Ala Asn Asp
225                 230                 235                 240

Asn Asn Ile Glu Asn Ala Ser Leu Ser Gly Ser Asn Phe Gly Ile Val
                245                 250                 255

Asp Ser Leu Ser Glu Leu Glu Ala Leu Met Glu Arg Met Lys Arg Leu
            260                 265                 270

Gln Glu Glu Arg Glu Asp Glu Glu Ala Ser Gln Glu Met Ser Thr
        275                 280                 285

Arg Phe Glu Lys Glu Lys Lys Glu Ser Leu Phe Val Val Ser Gly Asp
    290                 295                 300

Thr Phe His Ser Phe Pro His Ser Asp Phe Glu Asp Asp Met Ile Ile
305                 310                 315                 320

Thr Ser Asp Val Ser Arg Tyr Ile Glu Asp Pro Gly Phe Gly Tyr Glu
                325                 330                 335

Asp Phe Ala Arg Arg Gly Glu Glu His Leu Pro Thr Phe Arg Ala Gln
            340                 345                 350

Asp Tyr Thr Trp Glu Asn His Gly Phe Ser Leu Val Asn Arg Leu Tyr
    355                 360                 365

Ser Asp Ile Gly His Leu Leu Asp Glu Lys Phe Arg Met Val Tyr Asn
370                 375                 380

Leu Thr Tyr Asn Thr Met Ala Thr His Glu Asp Val Asp Thr Met
385                 390                 395                 400

Leu Arg Arg Ala Leu Phe Asn Tyr Val His Cys Met Phe Gly Ile Arg
```

```
                405                 410                 415
Tyr Asp Asp Tyr Asp Tyr Gly Glu Val Asn Gln Leu Leu Glu Arg Ser
            420                 425                 430

Leu Lys Val Tyr Ile Lys Thr Val Thr Cys Tyr Pro Glu Arg Thr Thr
            435                 440                 445

Lys Arg Met Tyr Asp Ser Tyr Trp Arg Gln Phe Lys His Ser Glu Lys
            450                 455                 460

Val His Val Asn Leu Leu Leu Met Glu Ala Arg Met Gln Ala Glu Leu
465                 470                 475                 480

Leu Tyr Ala Leu Arg Ala Ile Thr Arg His Leu Thr
            485                 490

<210> SEQ ID NO 4
<211> LENGTH: 875
<212> TYPE: PRT
<213> ORGANISM: Homo sapiens

<400> SEQUENCE: 4

Met Ser Gly Thr Lys Pro Asp Ile Leu Trp Ala Pro His His Val Asp
1               5                   10                  15

Arg Phe Val Val Cys Asp Ser Glu Leu Ser Leu Tyr His Val Glu Ser
                20                  25                  30

Thr Val Asn Ser Glu Leu Lys Ala Gly Ser Leu Arg Leu Ser Glu Asp
            35                  40                  45

Ser Ala Ala Thr Leu Leu Ser Ile Asn Ser Asp Thr Pro Tyr Met Lys
        50                  55                  60

Cys Val Ala Trp Tyr Leu Asn Tyr Asp Pro Glu Cys Leu Leu Ala Val
65                  70                  75                  80

Gly Gln Ala Asn Gly Arg Val Val Leu Thr Ser Leu Gly Gln Asp His
                85                  90                  95

Asn Ser Lys Phe Lys Asp Leu Ile Gly Lys Glu Phe Val Pro Lys His
            100                 105                 110

Ala Arg Gln Cys Asn Thr Leu Ala Trp Asn Pro Leu Asp Ser Asn Trp
        115                 120                 125

Leu Ala Ala Gly Leu Asp Lys His Arg Ala Asp Phe Ser Val Leu Ile
130                 135                 140

Trp Asp Ile Cys Ser Lys Tyr Thr Pro Asp Ile Val Pro Met Glu Lys
145                 150                 155                 160

Val Lys Leu Ser Ala Gly Glu Thr Gly Thr Thr Leu Leu Val Thr Lys
                165                 170                 175

Pro Leu Tyr Glu Leu Gly Gln Asn Asp Ala Cys Leu Ser Leu Cys Trp
            180                 185                 190

Leu Pro Arg Asp Gln Lys Leu Leu Ala Gly Met His Arg Asn Leu
        195                 200                 205

Ala Ile Phe Asp Leu Arg Asn Thr Ser Gln Lys Met Phe Val Asn Thr
210                 215                 220

Lys Ala Val Gln Gly Val Thr Val Asp Pro Tyr Phe His Asp Arg Val
225                 230                 235                 240

Ala Ser Phe Tyr Glu Gly Gln Val Ala Ile Trp Asp Leu Arg Lys Phe
                245                 250                 255

Glu Lys Pro Val Leu Thr Leu Thr Glu Gln Pro Lys Pro Leu Thr Lys
            260                 265                 270

Val Ala Trp Cys Pro Thr Arg Thr Gly Leu Leu Ala Thr Leu Thr Arg
        275                 280                 285
```

```
Asp Ser Asn Ile Ile Arg Leu Tyr Asp Met Gln His Thr Pro Thr Pro
    290                 295                 300

Ile Gly Asp Glu Thr Glu Pro Thr Ile Ile Glu Arg Ser Val Gln Pro
305                 310                 315                 320

Cys Asp Asn Tyr Ile Ala Ser Phe Ala Trp His Pro Thr Ser Gln Asn
                325                 330                 335

Arg Met Ile Val Val Thr Pro Asn Arg Thr Met Ser Asp Phe Thr Val
            340                 345                 350

Phe Glu Arg Ile Ser Leu Ala Trp Ser Pro Ile Thr Ser Leu Met Trp
        355                 360                 365

Ala Cys Gly Arg His Leu Tyr Glu Cys Thr Glu Glu Asn Asp Asn
370                 375                 380

Ser Leu Glu Lys Asp Ile Ala Thr Lys Met Arg Leu Arg Ala Leu Ser
385                 390                 395                 400

Arg Tyr Gly Leu Asp Thr Glu Gln Val Trp Arg Asn His Ile Leu Ala
                405                 410                 415

Gly Asn Glu Asp Pro Gln Leu Lys Ser Leu Trp Tyr Thr Leu His Phe
            420                 425                 430

Met Lys Gln Tyr Thr Glu Asp Met Asp Gln Lys Ser Pro Gly Asn Lys
        435                 440                 445

Gly Ser Leu Val Tyr Ala Gly Ile Lys Ser Ile Val Lys Ser Ser Leu
450                 455                 460

Gly Met Val Glu Ser Ser Arg His Asn Trp Ser Gly Leu Asp Lys Gln
465                 470                 475                 480

Ser Asp Ile Gln Asn Leu Asn Glu Glu Arg Ile Leu Ala Leu Gln Leu
                485                 490                 495

Cys Gly Trp Ile Lys Lys Gly Thr Asp Val Asp Val Gly Pro Phe Leu
            500                 505                 510

Asn Ser Leu Val Gln Glu Gly Glu Trp Glu Arg Ala Ala Ala Val Ala
        515                 520                 525

Leu Phe Asn Leu Asp Ile Arg Arg Ala Ile Gln Ile Leu Asn Glu Gly
530                 535                 540

Ala Ser Ser Glu Lys Gly Asp Leu Asn Leu Asn Val Val Ala Met Ala
545                 550                 555                 560

Leu Ser Gly Tyr Thr Asp Glu Lys Asn Ser Leu Trp Arg Glu Met Cys
                565                 570                 575

Ser Thr Leu Arg Leu Gln Leu Asn Asn Pro Tyr Leu Cys Val Met Phe
            580                 585                 590

Ala Phe Leu Thr Ser Glu Thr Gly Ser Tyr Asp Gly Val Leu Tyr Glu
        595                 600                 605

Asn Lys Val Ala Val Arg Asp Arg Val Ala Phe Ala Cys Lys Phe Leu
610                 615                 620

Ser Asp Thr Gln Leu Asn Arg Tyr Ile Glu Lys Leu Thr Asn Glu Met
625                 630                 635                 640

Lys Glu Ala Gly Asn Leu Glu Gly Ile Leu Leu Thr Gly Leu Thr Lys
                645                 650                 655

Asp Gly Val Asp Leu Met Glu Ser Tyr Val Asp Arg Thr Gly Asp Val
            660                 665                 670

Gln Thr Ala Ser Tyr Cys Met Leu Gln Gly Ser Pro Leu Asp Val Leu
        675                 680                 685

Lys Asp Glu Arg Val Gln Tyr Trp Ile Glu Asn Tyr Arg Asn Leu Leu
690                 695                 700

Asp Ala Trp Arg Phe Trp His Lys Arg Ala Glu Phe Asp Ile His Arg
```

```
                705                 710                 715                 720

Ser Lys Leu Asp Pro Ser Ser Lys Pro Leu Ala Gln Val Phe Val Ser
                725                 730                 735

Cys Asn Phe Cys Gly Lys Ser Ile Ser Tyr Ser Cys Ser Ala Val Pro
                740                 745                 750

His Gln Gly Arg Gly Phe Ser Gln Tyr Gly Val Ser Gly Ser Pro Thr
                755                 760                 765

Lys Ser Lys Val Thr Ser Cys Pro Gly Cys Arg Lys Pro Leu Pro Arg
                770                 775                 780

Cys Ala Leu Cys Leu Ile Asn Met Gly Thr Pro Val Ser Ser Cys Pro
785                 790                 795                 800

Gly Gly Thr Lys Ser Asp Glu Lys Val Asp Leu Ser Lys Asp Lys Lys
                805                 810                 815

Leu Ala Gln Phe Asn Asn Trp Phe Thr Trp Cys His Asn Cys Arg His
                820                 825                 830

Gly Gly His Ala Gly His Met Leu Ser Trp Phe Arg Asp His Ala Glu
                835                 840                 845

Cys Pro Val Ser Ala Cys Thr Cys Lys Cys Met Gln Leu Asp Thr Thr
                850                 855                 860

Gly Asn Leu Val Pro Ala Glu Thr Val Gln Pro
865                 870                 875
```

<210> SEQ ID NO 5
<211> LENGTH: 322
<212> TYPE: PRT
<213> ORGANISM: Homo sapiens

<400> SEQUENCE: 5

```
Met Val Ser Val Ile Asn Thr Val Asp Thr Ser His Glu Asp Met Ile
1               5                   10                  15

His Asp Ala Gln Met Asp Tyr Tyr Gly Thr Arg Leu Ala Thr Cys Ser
                20                  25                  30

Ser Asp Arg Ser Val Lys Ile Phe Asp Val Arg Asn Gly Gly Gln Ile
            35                  40                  45

Leu Ile Ala Asp Leu Arg Gly His Glu Gly Pro Val Trp Gln Val Ala
        50                  55                  60

Trp Ala His Pro Met Tyr Gly Asn Ile Leu Ala Ser Cys Ser Tyr Asp
65                  70                  75                  80

Arg Lys Val Ile Ile Trp Arg Glu Glu Asn Gly Thr Trp Glu Lys Ser
                85                  90                  95

His Glu His Ala Gly His Asp Ser Ser Val Asn Ser Val Cys Trp Ala
                100                 105                 110

Pro His Asp Tyr Gly Leu Ile Leu Ala Cys Gly Ser Ser Asp Gly Ala
            115                 120                 125

Ile Ser Leu Leu Thr Tyr Thr Gly Glu Gly Gln Trp Glu Val Lys Lys
        130                 135                 140

Ile Asn Asn Ala His Thr Ile Gly Cys Asn Ala Val Ser Trp Ala Pro
145                 150                 155                 160

Ala Val Val Pro Gly Ser Leu Ile Asp His Pro Ser Gly Gln Lys Pro
                165                 170                 175

Asn Tyr Ile Lys Arg Phe Ala Ser Gly Gly Cys Asp Asn Leu Ile Lys
                180                 185                 190

Leu Trp Lys Glu Glu Glu Asp Gly Gln Trp Lys Glu Glu Gln Lys Leu
            195                 200                 205
```

Glu Ala His Ser Asp Trp Val Arg Asp Val Ala Ala Pro Ser Ile
    210                 215                 220

Gly Leu Pro Thr Ser Thr Ile Ala Ser Cys Ser Gln Asp Gly Arg Val
225                 230                 235                 240

Phe Ile Trp Thr Cys Asp Asp Ala Ser Ser Asn Thr Trp Ser Pro Lys
                245                 250                 255

Leu Leu His Lys Phe Asn Asp Val Val Trp His Val Ser Trp Ser Ile
                260                 265                 270

Thr Ala Asn Ile Leu Ala Val Ser Gly Gly Asp Asn Lys Val Thr Leu
            275                 280                 285

Trp Lys Glu Ser Val Asp Gly Gln Trp Val Cys Ile Ser Asp Val Asn
290                 295                 300

Lys Gly Gln Gly Ser Val Ser Ala Ser Val Thr Glu Gly Gln Gln Asn
305                 310                 315                 320

Glu Gln

<210> SEQ ID NO 6
<211> LENGTH: 920
<212> TYPE: PRT
<213> ORGANISM: Homo sapiens

<400> SEQUENCE: 6

Met Gly Lys Lys Arg Thr Thr Ser Gly Glu Gly Arg Glu Arg Gln Arg
1               5                   10                  15

Leu Pro Ala Arg Arg Phe Arg Thr Thr Ser Pro Ala Ala Leu Arg Ala
                20                  25                  30

Asp Ser Val Asp Gly Gly Ser Leu Leu Ala Pro Leu Leu Gly Leu Thr
            35                  40                  45

Asp Arg Ala Phe Ser Asp Cys Pro Asp Leu Ala Asp Gly Ala Met Glu
50                  55                  60

Lys Met Ser Arg Val Thr Thr Ala Leu Gly Gly Ser Val Leu Thr Gly
65                  70                  75                  80

Arg Thr Met His Cys His Leu Asp Ala Pro Ala Asn Ala Ile Ser Val
                85                  90                  95

Cys Arg Asp Ala Ala Gln Val Val Val Ala Gly Arg Ser Ile Phe Lys
                100                 105                 110

Ile Tyr Ala Ile Glu Glu Glu Gln Phe Val Glu Lys Leu Asn Leu Arg
            115                 120                 125

Val Gly Arg Lys Pro Ser Leu Asn Leu Ser Cys Ala Asp Val Val Trp
130                 135                 140

His Gln Met Asp Glu Asn Leu Leu Ala Thr Ala Ala Thr Asn Gly Val
145                 150                 155                 160

Val Val Thr Trp Asn Leu Gly Arg Pro Ser Arg Asn Lys Gln Asp Gln
                165                 170                 175

Leu Phe Thr Glu His Lys Arg Thr Val Asn Lys Val Cys Phe His Pro
            180                 185                 190

Thr Glu Ala His Val Leu Leu Ser Gly Ser Gln Asp Gly Phe Met Lys
        195                 200                 205

Cys Phe Asp Leu Arg Arg Lys Asp Ser Val Ser Thr Phe Ser Gly Glu
210                 215                 220

Ala Thr Glu Ala Gly Pro Arg Glu Trp Ala Met Ala Gly Cys Val Pro
225                 230                 235                 240

Ile Leu Pro Val Leu Ser Cys Arg Ile Leu Arg Leu His Ser Phe
                245                 250                 255

```
Ala His Gly Pro Met Gln Asp Ala Glu Ser Thr Ala Asn Asp Ala Arg
            260                 265                 270

Glu Ser Trp Gly Cys Pro Leu Tyr Pro Leu Gly Leu Cys Ser Gly Pro
            275                 280                 285

Gln Ala Gly Gln Ser Glu Ser Val Arg Asp Val Gln Phe Ser Ile Arg
            290                 295                 300

Asp Tyr Phe Thr Phe Ala Ser Thr Phe Glu Asn Gly Asn Val Gln Leu
305                 310                 315                 320

Trp Asp Ile Arg Arg Pro Asp Arg Cys Glu Arg Met Phe Thr Ala His
                325                 330                 335

Asn Gly Pro Val Phe Cys Cys Asp Trp His Pro Glu Asp Arg Gly Trp
            340                 345                 350

Leu Ala Thr Gly Gly Arg Asp Lys Met Val Lys Val Trp Asp Met Thr
            355                 360                 365

Thr His Arg Ala Lys Glu Met His Cys Val Gln Thr Ile Ala Ser Val
370                 375                 380

Ala Arg Val Lys Trp Arg Pro Glu Cys Arg His His Leu Ala Thr Cys
385                 390                 395                 400

Ser Met Met Val Asp His Asn Ile Tyr Val Trp Asp Val Arg Arg Pro
                405                 410                 415

Phe Val Pro Ala Ala Met Phe Glu Glu His Arg Asp Val Thr Thr Gly
            420                 425                 430

Ile Ala Trp Arg His Pro His Asp Pro Ser Phe Leu Leu Ser Gly Ser
            435                 440                 445

Lys Asp Ser Ser Leu Cys Gln His Leu Phe Arg Asp Ala Ser Gln Pro
450                 455                 460

Val Glu Arg Ala Asn Pro Glu Gly Leu Cys Tyr Gly Leu Phe Gly Asp
465                 470                 475                 480

Leu Ala Phe Ala Ala Lys Glu Ser Leu Val Ala Ala Glu Ser Gly Arg
                485                 490                 495

Lys Pro Tyr Thr Gly Asp Arg Arg His Pro Ile Phe Phe Lys Arg Lys
            500                 505                 510

Leu Asp Pro Ala Glu Pro Phe Ala Gly Leu Ala Ser Ser Ala Leu Ser
            515                 520                 525

Val Phe Glu Thr Glu Pro Gly Gly Gly Met Arg Trp Phe Val Asp
530                 535                 540

Thr Ala Glu Arg Tyr Ala Leu Ala Gly Arg Pro Leu Ala Glu Leu Cys
545                 550                 555                 560

Asp His Asn Ala Lys Val Ala Arg Glu Leu Gly Arg Asn Gln Val Ala
                565                 570                 575

Gln Thr Trp Thr Met Leu Arg Ile Ile Tyr Cys Ser Pro Gly Leu Val
            580                 585                 590

Pro Thr Ala Asn Leu Asn His Ser Val Gly Lys Gly Ser Cys Gly
            595                 600                 605

Leu Pro Leu Met Asn Ser Phe Asn Leu Lys Asp Met Ala Pro Gly Leu
            610                 615                 620

Gly Ser Glu Thr Arg Leu Asp Arg Ser Lys Gly Asp Ala Arg Ser Asp
625                 630                 635                 640

Thr Val Leu Leu Asp Ser Ser Ala Thr Leu Ile Thr Asn Glu Asp Asn
                645                 650                 655

Glu Glu Thr Glu Gly Ser Asp Val Pro Ala Asp Tyr Leu Leu Gly Asp
            660                 665                 670

Val Glu Gly Glu Glu Asp Glu Leu Tyr Leu Leu Asp Pro Glu His Ala
```

```
                675                 680                 685
His Pro Glu Asp Pro Glu Cys Val Leu Pro Gln Glu Ala Phe Pro Leu
    690                 695                 700
Arg His Glu Ile Val Asp Thr Pro Pro Gly Pro Glu His Leu Gln Asp
705                 710                 715                 720
Lys Ala Asp Ser Pro His Val Ser Gly Ser Glu Ala Asp Val Ala Ser
                725                 730                 735
Leu Ala Pro Val Asp Ser Ser Phe Ser Leu Leu Ser Val Ser His Ala
            740                 745                 750
Leu Tyr Asp Ser Arg Leu Pro Pro Asp Phe Phe Gly Val Leu Val Arg
        755                 760                 765
Asp Met Leu His Phe Tyr Ala Glu Gln Gly Asp Val Gln Met Ala Val
    770                 775                 780
Ser Val Leu Ile Val Leu Gly Glu Arg Val Arg Lys Asp Ile Asp Glu
785                 790                 795                 800
Gln Thr Gln Glu His Trp Tyr Thr Ser Tyr Ile Asp Leu Leu Gln Arg
                805                 810                 815
Phe Arg Leu Trp Asn Val Ser Asn Glu Val Val Lys Leu Ser Thr Ser
            820                 825                 830
Arg Ala Val Ser Cys Leu Asn Gln Ala Ser Thr Thr Leu His Val Asn
        835                 840                 845
Cys Ser His Cys Lys Arg Pro Met Ser Ser Arg Gly Trp Val Cys Asp
    850                 855                 860
Arg Cys His Arg Cys Ala Ser Met Cys Ala Val Cys His His Val Val
865                 870                 875                 880
Lys Gly Leu Phe Val Trp Cys Gln Gly Cys Ser His Gly Gly His Leu
                885                 890                 895
Gln His Ile Met Lys Trp Leu Gly Ser Ser His Cys Pro Ala Gly
            900                 905                 910
Cys Gly His Leu Cys Glu Tyr Ser
        915                 920

<210> SEQ ID NO 7
<211> LENGTH: 974
<212> TYPE: PRT
<213> ORGANISM: Homo sapiens

<400> SEQUENCE: 7

Met Ala Ala Arg Trp Ser Ser Glu Asn Val Val Glu Phe Arg Asp
1               5                   10                  15
Ser Gln Ala Thr Ala Met Ser Val Asp Cys Leu Gly Gln His Ala Val
                20                  25                  30
Leu Ser Gly Arg Arg Phe Leu Tyr Ile Val Asn Leu Asp Ala Pro Phe
            35                  40                  45
Glu Gly His Arg Lys Ile Ser Arg Gln Ser Lys Trp Asp Ile Gly Ala
        50                  55                  60
Val Gln Trp Asn Pro His Asp Ser Phe Ala His Tyr Phe Ala Ala Ser
65                  70                  75                  80
Ser Asn Gln Arg Val Asp Leu Tyr Lys Trp Lys Asp Gly Ser Gly Glu
                85                  90                  95
Val Gly Thr Thr Leu Gln Gly His Thr Arg Val Ile Ser Asp Leu Asp
            100                 105                 110
Trp Ala Val Phe Glu Pro Asp Leu Leu Val Thr Ser Ser Val Asp Thr
        115                 120                 125
```

```
Tyr Ile Tyr Ile Trp Asp Ile Lys Asp Thr Arg Lys Pro Thr Val Ala
        130                 135                 140

Leu Ser Ala Val Ala Gly Ala Ser Gln Val Lys Trp Asn Lys Lys Asn
145                 150                 155                 160

Ala Asn Cys Leu Ala Thr Ser His Asp Gly Asp Val Arg Ile Trp Asp
                165                 170                 175

Lys Arg Lys Pro Ser Thr Ala Val Glu Tyr Leu Ala Ala His Leu Ser
            180                 185                 190

Lys Ile His Gly Leu Asp Trp His Pro Asp Ser Glu His Ile Leu Ala
        195                 200                 205

Thr Ser Ser Gln Asp Asn Ser Val Lys Phe Trp Asp Tyr Arg Gln Pro
210                 215                 220

Arg Lys Tyr Leu Asn Ile Leu Pro Cys Gln Val Pro Val Trp Lys Ala
225                 230                 235                 240

Arg Tyr Thr Pro Phe Ser Asn Gly Leu Val Thr Val Met Val Pro Gln
                245                 250                 255

Leu Arg Arg Glu Asn Ser Leu Leu Leu Trp Asn Val Phe Asp Leu Asn
            260                 265                 270

Thr Pro Val His Thr Phe Val Gly His Asp Asp Val Val Leu Glu Phe
        275                 280                 285

Gln Trp Arg Lys Gln Lys Glu Gly Ser Lys Asp Tyr Gln Leu Val Thr
290                 295                 300

Trp Ser Arg Asp Gln Thr Leu Arg Met Trp Arg Val Asp Ser Gln Met
305                 310                 315                 320

Gln Arg Leu Cys Ala Asn Asp Ile Leu Asp Gly Val Asp Glu Phe Ile
                325                 330                 335

Glu Ser Ile Ser Leu Leu Pro Glu Pro Glu Lys Thr Leu His Thr Glu
            340                 345                 350

Asp Thr Asp His Gln His Thr Ala Ser His Gly Glu Glu Ala Leu
        355                 360                 365

Lys Glu Asp Pro Pro Arg Asn Leu Leu Glu Glu Arg Lys Ser Asp Gln
370                 375                 380

Leu Gly Leu Pro Gln Thr Leu Gln Gln Glu Phe Ser Leu Ile Asn Val
385                 390                 395                 400

Gln Ile Arg Asn Val Asn Val Glu Met Asp Ala Ala Asp Arg Ser Cys
                405                 410                 415

Thr Val Ser Val His Cys Ser Asn His Arg Val Lys Met Leu Val Lys
            420                 425                 430

Phe Pro Ala Gln Tyr Pro Asn Asn Ala Ala Pro Ser Phe Gln Phe Ile
        435                 440                 445

Asn Pro Thr Thr Ile Thr Ser Thr Met Lys Ala Lys Leu Leu Lys Ile
450                 455                 460

Leu Lys Asp Thr Ala Leu Gln Lys Val Lys Arg Gly Gln Ser Cys Leu
465                 470                 475                 480

Glu Pro Cys Leu Arg Gln Leu Val Ser Cys Leu Glu Ser Phe Val Asn
                485                 490                 495

Gln Glu Asp Ser Ala Ser Ser Asn Pro Phe Ala Leu Pro Asn Ser Val
            500                 505                 510

Thr Pro Pro Leu Pro Thr Phe Ala Arg Val Thr Thr Ala Tyr Gly Ser
        515                 520                 525

Tyr Gln Asp Ala Asn Ile Pro Phe Pro Arg Thr Ser Gly Ala Arg Phe
530                 535                 540

Cys Gly Ala Gly Tyr Leu Val Tyr Phe Thr Arg Pro Met Thr Met His
```

```
      545                 550                 555                 560
Arg Ala Val Ser Pro Thr Glu Pro Thr Pro Arg Ser Leu Ser Ala Leu
                  565                 570                 575

Ser Ala Tyr His Thr Gly Leu Ile Ala Pro Met Lys Ile Arg Thr Glu
                  580                 585                 590

Ala Pro Gly Asn Leu Arg Leu Tyr Ser Gly Ser Pro Thr Arg Ser Glu
                  595                 600                 605

Lys Glu Gln Val Ser Ile Ser Ser Phe Tyr Tyr Lys Glu Arg Lys Ser
                  610                 615                 620

Arg Arg Trp Lys Ser Lys Arg Glu Gly Ser Asp Ser Gly Asn Arg Gln
625                 630                 635                 640

Ile Lys Ala Ala Gly Lys Val Ile Ile Gln Asp Ile Ala Cys Leu Leu
                  645                 650                 655

Pro Val His Lys Ser Leu Gly Glu Leu Tyr Ile Leu Asn Val Asn Asp
                  660                 665                 670

Ile Gln Glu Thr Cys Gln Lys Asn Ala Ala Ser Ala Leu Leu Val Gly
                  675                 680                 685

Arg Lys Asp Leu Val Gln Val Trp Ser Leu Ala Thr Val Ala Thr Asp
690                 695                 700

Leu Cys Leu Gly Pro Lys Ser Asp Pro Asp Leu Glu Thr Pro Trp Ala
705                 710                 715                 720

Arg His Pro Phe Gly Arg Gln Leu Leu Glu Ser Leu Leu Ala His Tyr
                  725                 730                 735

Cys Arg Leu Arg Asp Val Gln Thr Leu Ala Met Leu Cys Ser Val Phe
                  740                 745                 750

Glu Ala Gln Ser Arg Pro Gln Gly Leu Pro Asn Pro Phe Gly Pro Phe
                  755                 760                 765

Pro Asn Arg Ser Ser Asn Leu Val Val Ser His Ser Arg Tyr Pro Ser
                  770                 775                 780

Phe Thr Ser Ser Gly Ser Cys Ser Ser Met Ser Asp Pro Gly Leu Asn
785                 790                 795                 800

Thr Gly Gly Trp Asn Ile Ala Gly Arg Glu Ala Glu His Leu Ser Ser
                  805                 810                 815

Pro Trp Gly Glu Ser Ser Pro Glu Glu Leu Arg Phe Gly Ser Leu Thr
                  820                 825                 830

Tyr Ser Asp Pro Arg Glu Arg Glu Arg Asp Gln His Asp Lys Asn Lys
                  835                 840                 845

Arg Leu Leu Asp Pro Ala Asn Thr Gln Gln Phe Asp Asp Phe Lys Lys
850                 855                 860

Cys Tyr Gly Glu Ile Leu Tyr Arg Trp Gly Leu Arg Glu Lys Arg Ala
865                 870                 875                 880

Glu Val Leu Lys Phe Val Ser Cys Pro Pro Asp Pro His Lys Gly Ile
                  885                 890                 895

Glu Phe Gly Val Tyr Cys Ser His Cys Arg Ser Glu Val Arg Gly Thr
                  900                 905                 910

Gln Cys Ala Ile Cys Lys Gly Phe Thr Phe Gln Cys Ala Ile Cys His
                  915                 920                 925

Val Ala Val Arg Gly Ser Ser Asn Phe Cys Leu Thr Cys Gly His Gly
                  930                 935                 940

Gly His Thr Ser His Met Met Glu Trp Phe Arg Thr Gln Glu Val Cys
945                 950                 955                 960

Pro Thr Gly Cys Gly Cys His Cys Leu Leu Glu Ser Thr Phe
                  965                 970
```

```
<210> SEQ ID NO 8
<211> LENGTH: 360
<212> TYPE: PRT
<213> ORGANISM: Homo sapiens

<400> SEQUENCE: 8

Met Phe Val Ala Arg Ser Ile Ala Ala Asp His Lys Asp Leu Ile His
1               5                   10                  15

Asp Val Ser Phe Asp Phe His Gly Arg Arg Met Ala Thr Cys Ser Ser
                20                  25                  30

Asp Gln Ser Val Lys Val Trp Asp Lys Ser Glu Ser Gly Asp Trp His
            35                  40                  45

Cys Thr Ala Ser Trp Lys Thr His Ser Gly Ser Val Trp Arg Val Thr
    50                  55                  60

Trp Ala His Pro Glu Phe Gly Gln Val Leu Ala Ser Cys Ser Phe Asp
65                  70                  75                  80

Arg Thr Ala Ala Val Trp Glu Glu Ile Val Gly Glu Ser Asn Asp Lys
                85                  90                  95

Leu Arg Gly Gln Ser His Trp Val Lys Arg Thr Thr Leu Val Asp Ser
            100                 105                 110

Arg Thr Ser Val Thr Asp Val Lys Phe Ala Pro Lys His Met Gly Leu
        115                 120                 125

Met Leu Ala Thr Cys Ser Ala Asp Gly Ile Val Arg Ile Tyr Glu Ala
130                 135                 140

Pro Asp Val Met Asn Leu Ser Gln Trp Ser Leu Gln His Glu Ile Ser
145                 150                 155                 160

Cys Lys Leu Ser Cys Ser Cys Ile Ser Trp Asn Pro Ser Ser Ser Arg
                165                 170                 175

Ala His Ser Pro Met Ile Ala Val Gly Ser Asp Asp Ser Ser Pro Asn
            180                 185                 190

Ala Met Ala Lys Val Gln Ile Phe Glu Tyr Asn Glu Asn Thr Arg Lys
        195                 200                 205

Tyr Ala Lys Ala Glu Thr Leu Met Thr Val Thr Asp Pro Val His Asp
    210                 215                 220

Ile Ala Phe Ala Pro Asn Leu Gly Arg Ser Phe His Ile Leu Ala Ile
225                 230                 235                 240

Ala Thr Lys Asp Val Arg Ile Phe Thr Leu Lys Pro Val Arg Lys Glu
                245                 250                 255

Leu Thr Ser Ser Gly Gly Pro Thr Lys Phe Glu Ile His Ile Val Ala
            260                 265                 270

Gln Phe Asp Asn His Asn Ser Gln Val Trp Arg Val Ser Trp Asn Ile
        275                 280                 285

Thr Gly Thr Val Leu Ala Ser Ser Gly Asp Asp Gly Cys Val Arg Leu
    290                 295                 300

Trp Lys Ala Asn Tyr Met Asp Asn Trp Lys Cys Thr Gly Ile Leu Lys
305                 310                 315                 320

Gly Asn Gly Ser Pro Val Asn Gly Ser Ser Gln Gln Gly Thr Ser Asn
                325                 330                 335

Pro Ser Leu Gly Ser Thr Ile Pro Ser Leu Gln Asn Ser Leu Asn Gly
            340                 345                 350

Ser Ser Ala Gly Arg Lys His Ser
        355                 360
```

<210> SEQ ID NO 9
<211> LENGTH: 492
<212> TYPE: PRT
<213> ORGANISM: Homo sapiens

<400> SEQUENCE: 9

```
Met Arg Leu Ala Ala Ala Asn Glu Ala Tyr Thr Ala Pro Leu Ala
1               5                   10                  15

Val Ser Gly Leu Leu Gly Cys Lys Gln Cys Gly Gly Arg Asp Gln
                20                  25                  30

Asp Glu Glu Leu Gly Ile Arg Ile Pro Arg Pro Leu Gly Gln Gly Pro
            35                  40                  45

Ser Arg Phe Ile Pro Glu Lys Glu Ile Leu Gln Val Gly Ser Glu Asp
    50                  55                  60

Ala Gln Met His Ala Leu Phe Ala Asp Ser Phe Ala Ala Leu Gly Arg
65                  70                  75                  80

Leu Asp Asn Ile Thr Leu Val Met Val Phe His Pro Gln Tyr Leu Glu
                85                  90                  95

Ser Phe Leu Lys Thr Gln His Tyr Leu Leu Gln Met Asp Gly Pro Leu
                100                 105                 110

Pro Leu His Tyr Arg His Tyr Ile Gly Ile Met Ala Ala Ala Arg His
            115                 120                 125

Gln Cys Ser Tyr Leu Val Asn Leu His Val Asn Asp Phe Leu His Val
130                 135                 140

Gly Gly Asp Pro Lys Trp Leu Asn Gly Leu Glu Asn Ala Pro Gln Lys
145                 150                 155                 160

Leu Gln Asn Leu Gly Glu Leu Asn Lys Val Leu Ala His Arg Pro Trp
                165                 170                 175

Leu Ile Thr Lys Glu His Ile Glu Gly Leu Leu Lys Ala Glu Glu His
            180                 185                 190

Ser Trp Ser Leu Ala Glu Leu Val His Ala Val Val Leu Leu Thr His
    195                 200                 205

Tyr His Ser Leu Ala Ser Phe Thr Phe Gly Cys Gly Ile Ser Pro Glu
210                 215                 220

Ile His Cys Asp Gly Gly His Thr Phe Arg Pro Pro Ser Val Ser Asn
225                 230                 235                 240

Tyr Cys Ile Cys Asp Ile Thr Asn Gly Asn His Ser Val Asp Glu Met
                245                 250                 255

Pro Val Asn Ser Ala Glu Asn Val Ser Val Ser Asp Ser Phe Phe Glu
            260                 265                 270

Val Glu Ala Leu Met Glu Lys Met Arg Gln Leu Gln Glu Cys Arg Asp
    275                 280                 285

Glu Glu Glu Ala Ser Gln Glu Glu Met Ala Ser Arg Phe Glu Ile Glu
290                 295                 300

Lys Arg Glu Ser Met Phe Val Phe Ser Ser Asp Asp Glu Glu Val Thr
305                 310                 315                 320

Pro Ala Arg Ala Val Ser Arg His Phe Glu Asp Thr Ser Tyr Gly Tyr
                325                 330                 335

Lys Asp Phe Ser Arg His Gly Met His Val Pro Thr Phe Arg Val Gln
            340                 345                 350

Asp Tyr Cys Trp Glu Asp His Gly Tyr Ser Leu Val Asn Arg Leu Tyr
    355                 360                 365

Pro Asp Val Gly Gln Leu Ile Asp Glu Lys Phe His Ile Ala Tyr Asn
370                 375                 380
```

```
Leu Thr Tyr Asn Thr Met Ala Met His Lys Asp Val Asp Thr Ser Met
385                 390                 395                 400

Leu Arg Arg Ala Ile Trp Asn Tyr Ile His Cys Met Phe Gly Ile Arg
            405                 410                 415

Tyr Asp Asp Tyr Asp Tyr Gly Glu Ile Asn Gln Leu Leu Asp Arg Ser
        420                 425                 430

Phe Lys Val Tyr Ile Lys Thr Val Val Cys Thr Pro Glu Lys Val Thr
    435                 440                 445

Lys Arg Met Tyr Asp Ser Phe Trp Arg Gln Phe Lys His Ser Glu Lys
450                 455                 460

Val His Val Asn Leu Leu Leu Ile Glu Ala Arg Met Gln Ala Glu Leu
465                 470                 475                 480

Leu Tyr Ala Leu Arg Ala Ile Thr Arg Tyr Met Thr
                485                 490

<210> SEQ ID NO 10
<211> LENGTH: 426
<212> TYPE: PRT
<213> ORGANISM: Homo sapiens

<400> SEQUENCE: 10

Met His Ala Leu Phe Ala Asp Ser Phe Ala Ala Leu Gly Arg Leu Asp
1               5                   10                  15

Asn Ile Thr Leu Val Met Val Phe His Pro Gln Tyr Leu Glu Ser Phe
            20                  25                  30

Leu Lys Thr Gln His Tyr Leu Leu Gln Met Asp Gly Pro Leu Pro Leu
        35                  40                  45

His Tyr Arg His Tyr Ile Gly Ile Met Ala Ala Arg His Gln Cys
    50                  55                  60

Ser Tyr Leu Val Asn Leu His Val Asn Asp Phe Leu His Val Gly Gly
65                  70                  75                  80

Asp Pro Lys Trp Leu Asn Gly Leu Glu Asn Ala Pro Gln Lys Leu Gln
                85                  90                  95

Asn Leu Gly Glu Leu Asn Lys Val Leu Ala His Arg Pro Trp Leu Ile
            100                 105                 110

Thr Lys Glu His Ile Glu Gly Leu Leu Lys Ala Glu His Ser Trp
        115                 120                 125

Ser Leu Ala Glu Leu Val His Ala Val Leu Leu Thr His Tyr His
    130                 135                 140

Ser Leu Ala Ser Phe Thr Phe Gly Cys Gly Ile Ser Pro Glu Ile His
145                 150                 155                 160

Cys Asp Gly Gly His Thr Phe Arg Pro Pro Ser Val Ser Asn Tyr Cys
                165                 170                 175

Ile Cys Asp Ile Thr Asn Gly Asn His Ser Val Asp Glu Met Pro Val
            180                 185                 190

Asn Ser Ala Glu Asn Val Ser Val Ser Asp Ser Phe Phe Glu Val Glu
        195                 200                 205

Ala Leu Met Glu Lys Met Arg Gln Leu Gln Glu Cys Arg Asp Glu Glu
    210                 215                 220

Glu Ala Ser Gln Glu Glu Met Ala Ser Arg Phe Glu Ile Glu Lys Arg
225                 230                 235                 240

Glu Ser Met Phe Val Phe Ser Ser Asp Glu Glu Val Thr Pro Ala
                245                 250                 255

Arg Ala Val Ser Arg His Phe Glu Asp Thr Ser Tyr Gly Tyr Lys Asp
            260                 265                 270
```

```
Phe Ser Arg His Gly Met His Val Pro Thr Phe Arg Val Gln Asp Tyr
            275                 280                 285

Cys Trp Glu Asp His Gly Tyr Ser Leu Val Asn Arg Leu Tyr Pro Asp
290                 295                 300

Val Gly Gln Leu Ile Asp Glu Lys Phe His Ile Ala Tyr Asn Leu Thr
305                 310                 315                 320

Tyr Asn Thr Met Ala Met His Lys Asp Val Asp Thr Ser Met Leu Arg
            325                 330                 335

Arg Ala Ile Trp Asn Tyr Ile His Cys Met Phe Gly Ile Arg Tyr Asp
            340                 345                 350

Asp Tyr Asp Tyr Gly Glu Ile Asn Gln Leu Leu Asp Arg Ser Phe Lys
            355                 360                 365

Val Tyr Ile Lys Thr Val Val Cys Thr Pro Glu Lys Val Thr Lys Arg
            370                 375                 380

Met Tyr Asp Ser Phe Trp Arg Gln Phe Lys His Ser Glu Lys Val His
385                 390                 395                 400

Val Asn Leu Leu Leu Ile Glu Ala Arg Met Gln Ala Glu Leu Leu Tyr
                405                 410                 415

Ala Leu Arg Ala Ile Thr Arg Tyr Met Thr
            420                 425

<210> SEQ ID NO 11
<211> LENGTH: 353
<212> TYPE: PRT
<213> ORGANISM: Homo sapiens

<400> SEQUENCE: 11

Met Ser Leu His Thr Gln Tyr Leu Glu Ser Phe Leu Arg Ser Gln Phe
1               5                   10                  15

Tyr Met Leu Arg Met Asp Gly Pro Leu Pro Leu Pro Tyr Arg His Tyr
                20                  25                  30

Ile Ala Ile Met Lys Leu Val Lys Thr Gly Glu Asn Asn Trp Ser Leu
            35                  40                  45

Pro Glu Leu Val His Ala Val Leu Leu Ala His Tyr His Ala Leu
50                  55                  60

Ala Ser Phe Val Phe Gly Ser Gly Ile Asn Pro Glu Arg Asp Pro Glu
65                  70                  75                  80

Ile Ser Asn Gly Phe Arg Leu Ile Ser Val Asn Asn Phe Cys Val Cys
                85                  90                  95

Asp Leu Ala Asn Asp Asn Asn Ile Glu Asn Ala Ser Leu Ser Gly Ser
            100                 105                 110

Asn Phe Gly Ile Val Asp Ser Leu Ser Glu Leu Glu Ala Leu Met Glu
            115                 120                 125

Arg Met Lys Arg Leu Gln Glu Glu Arg Glu Asp Glu Glu Ala Ser Gln
130                 135                 140

Glu Glu Met Ser Thr Arg Phe Glu Lys Gly Lys Lys Glu Ser Leu Phe
145                 150                 155                 160

Val Val Ser Gly Asp Thr Phe His Ser Phe Pro His Ser Asp Phe Glu
                165                 170                 175

Asp Asp Met Ile Ile Thr Ser Asp Val Ser Arg Tyr Ile Glu Asp Pro
            180                 185                 190

Gly Phe Gly Tyr Glu Asp Phe Ala Arg Arg Gly Glu Glu His Leu Pro
            195                 200                 205

Thr Phe Arg Ala Gln Asp Tyr Thr Trp Glu Asn His Gly Phe Ser Leu
```

```
          210                 215                 220
Val Asn Arg Leu Tyr Ser Asp Ile Gly His Leu Leu Asp Glu Lys Phe
225                 230                 235                 240

Arg Met Val Tyr Asn Leu Thr Tyr Asn Thr Met Ala Thr His Glu Asp
                245                 250                 255

Val Asp Thr Thr Met Leu Arg Arg Ala Leu Phe Asn Tyr Val His Cys
            260                 265                 270

Met Phe Gly Ile Arg Tyr Asp Asp Tyr Asp Tyr Gly Glu Val Asn Gln
        275                 280                 285

Leu Leu Glu Arg Ser Leu Lys Val Tyr Ile Lys Thr Val Thr Cys Tyr
    290                 295                 300

Pro Glu Arg Thr Thr Lys Arg Met Tyr Asp Ser Tyr Trp Arg Gln Phe
305                 310                 315                 320

Lys His Ser Glu Lys Val His Val Asn Leu Leu Met Glu Ala Arg
                325                 330                 335

Met Gln Ala Glu Leu Leu Tyr Ala Leu Arg Ala Ile Thr Arg His Leu
            340                 345                 350

Thr
```

```
<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
caccgatcac atcagtaaac atgag                                          25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aaacctcatg tttactgatg tgatc                                          25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
caccgaccca gggctgtggt cacac                                          25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aaacgtgtga ccacagccct gggtc                                          25
```

```
<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
caccgcgggg gagatggcgg cgcga                                               25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aaactcgcgc cgccatctcc cccgc                                               25

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
caccgtgaac cgcatcgagc tgaa                                                24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aaacttcagc tcgatgcggt tcac                                                24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
caccggcttt caggctccgt tcga                                                24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aaactcgaac ggagcctgaa agcc                                                24
```

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tggcaatgca caaagatgtt g                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gctacgatcc aatagctggt t                                              21

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgcgtttgtg atcttgctaa tg                                             22

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cgcctcttca tcttcccttt c                                              21

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
caccgagagc ctcgagcagc acctg                                          25

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aaaccaggtg ctgctcgagg ctctc                                          25

```
<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
caccggacta cctgcggttc gccc                                              24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aaacgggcga accgcaggta gtcc                                              24

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
caccgccaca gccaaacacg aagg                                              24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
aaaccctccg tgtttggctg tggc                                              24
```

METHODS OF IDENTIFYING MODULATORS OF SESTRIN-GATOR-2 INTERACTION FOR MODULATING MTORC1 ACTIVITY

RELATED APPLICATIONS

This application is a national stage filing under 35 U.S.C. 371 of International Application No.: PCT/US2015/049727, filed Sep. 11, 2015, which claims the benefit of United States Provisional Application Nos. 62/049,922, filed Sep. 12, 2014, and 62/155,795, filed May 1, 2015, the entire teachings of which are incorporated herein by reference. International Application No.: PCT/US2015/049727 was published under PCT Article 21(2) in English.

GOVERNMENT SUPPORT

This invention was made with government support under RO1 CA103866 and AI47389 awarded by the National Institutes of Health, and W81XWH-07-0448 awarded by the Department of Defense. The government has certain rights in the invention.

BACKGROUND OF THE INVENTION

The mechanistic target of rapamycin complex 1 (mTORC1) protein kinase is a master growth regulator that senses diverse environmental cues, such as growth factors, cellular stresses, and nutrient and energy levels. When activated, mTORC1 phosphorylates substrates that potentiate anabolic processes, such as mRNA translation and lipid synthesis, and limits catabolic ones, such as autophagy. mTORC1 dysregulation occurs in a broad spectrum of diseases, including diabetes, epilepsy, neurodegeneration, immune response, suppressed skeletal muscle growth, and cancer among others (Howell et al., 2013; Kim et al., 2013; Laplante and Sabatini, 2012).

Many upstream inputs, including growth factors and energy levels, signal to mTORC1 through the TSC complex, which regulates Rheb, a small GTPase that is an essential activator of mTORC1 (Brugarolas et at, 2004; Garami et al., 2003; Inoki et al., 2003; Long et al., 2005; Sancak et al., 2008; Saucedo et al., 2003; Stocker et al., 2003; Tee et al., 2002). Amino acids do not appear to signal to mTORC1 through the TSC-Rheb axis and instead act through the heterodimeric Rag GTPases, which consist of RagA or RagB bound to RagC or RagD, respectively (Hirose et al., 1998; Kim et al., 2008; Nobukuni et al., 2005; Roccio et al., 2005; Sancak et al., 2008; Schumann et al., 1995; Sekiguchi et al., 2001; Smith et al., 2005). The Rag GTPases control the subcellular localization of mTORC1 and amino acids promote its recruitment to the lysosomal surface, where the Rheb GTPase also resides (Buerger et al., 2006; Dibble et al., 2012; Saito et al., 2005; Sancak et al., 2008). Several positive components of the pathway upstream of the Rag GTPases have been identified. The Ragulator complex localizes the Rag GTPases to the lysosomal surface and, along with the vacuolar-ATPase, promotes the exchange of GDP for GTP on RagA/B (Bar-Peled et al., 2012; Sancak et al., 2010b; Zoncu et al., 2011). The distinct FLCN-FNIP complex acts on RagC/D and stimulates its hydrolysis of GTP into GDP (Tsun et al., 2013). When RagA/B is loaded with GTP and RagC/D with GDP, the heterodimers bind and recruit mTORC1 to the lysosomal surface, where it can come in contact with its activator Rheb GTPase.

Recent work has identified the GATOR1 multi-protein complex as a major negative regulator of the amino acid sensing pathway and its loss causes mTORC1 signaling to be completely insensitive to amino acid starvation (Bar-Peled et al., 2013; Panchaud et al., 2013). GATOR1 consists of DEPDCS, Npr12, and Npr13, and is a GTPase activating protein (GAP) for RagA/B. The GATOR2 multi-protein complex, which has five known subunits (WDR24, WDR59, Mios, Sec13, and Seh1L), is a positive component of the pathway and upstream of or parallel to GATOR1, but its molecular function is unknown (Bar-Peled et al., 2013).

The Sestrins are three related proteins (Sestrin1, -2 and -3) of poorly characterized molecular functions (Buckbinder et al., 1994; Budanov et al., 2002; Peeters et al., 2003). Sestrin2 inhibits mTORC1 signaling and has been proposed to activate AMPK upstream of TSC as well as interact with TSC (Budanov and Karin, 2008), but its mechanism of action remains undefined.

There is still a great need to better understand how amino acids modulate mTORC1 activity and to identify the crucial components mediating this modulation. Such components are potential therapeutic targets for selectively modulating mTORC1 activity indirectly.

SUMMARY OF THE INVENTION

The present invention provides additional information about the mTORC1 pathway by identifying the binding of GATOR2 with one or more of the Sestrins and the resulting GATOR2-Sestrin complex regulating the subcellular localization and activity of mTORC1. In particular, the presence of GATOR2-Sestrin complexes inhibits the mTORC1 pathway and decreases mTORC1 activity by preventing translocation of mTORC1 to the lysosomal membrane. The present inventors have also discovered that the interaction of GATOR2 with the Sestrins, and in particular Sestrin1 and Sestrin2, is antagonized by amino acids, particularly leucine and, to a lesser extent, isoleucine, methionine and valine. In the presence of leucine, GATOR2 does not interact with Sestrin1 or Sestrin2 and mTORC1 is able to migrate to the lysosomal membrane where it is active. The inventors have also discovered that Sestrin1 and Sestrin2 directly bind leucine and to a lesser extent, isoleucine and methionine. The binding of leucine by Sestrin1 or -2 is required for disruption of its interaction with GATOR2 and subsequent activation of mTORC1.

In some embodiments, the invention provides a method of identifying a test compound as an activator of mTORC1 by determining if the test compound can reduce or antagonize the interaction of GATOR2 with a Sestrin. In one aspect of these embodiments, the method comprises the steps of:
a) providing a mixture comprising:
   (i) a first polypeptide comprising the amino acid sequence of: a GATOR2 binding fragment of Sestrin1 (SEQ ID NO:1), Sestrin2 (SEQ ID NO:2), Sestrin3 (SEQ ID NO:3), or a polypeptide having at least 80% homology to any one of SEQ ID NOS:1-3 that retains the ability to bind GATOR2; and
   (ii) a second polypeptide or protein complex comprising the amino acid sequence of: a Sestrin-binding fragment of a GATOR2 complex (SEQ ID NOS:4-8), or a polypeptide or protein complex having at least 80% homology to SEQ ID NOs:4-8 that retains the ability to bind to at least one of Sestrin1, Sestrin2 or Sestrin3,
under conditions that allow the first polypeptide to associate with the second polypeptide or protein complex;

b) incubating the mixture of a) with the test compound; and
c) determining whether the amount of the first polypeptide associated with the second polypeptide or protein complex is altered in the presence of the test compound as compared to either the absence of the test compound or the presence of a negative control, wherein if the amount of association is decreased the test compound is identified as an activator of mTORC1 activity.

In some embodiments, the invention provides a method of identifying a test compound as an inhibitor of mTORC1 activity by determining if the test compound can induce or increase the interaction of GATOR2 with a Sestrin. In one aspect of these embodiments, the method comprises the steps of:
  a) providing a mixture comprising:
    (i) a first polypeptide comprising the amino acid sequence of: a GATOR2 binding fragment of Sestrin1 (SEQ ID NO:1), Sestrin2 (SEQ ID NO:2), Sestrin3 (SEQ ID NO:3), or a polypeptide having at least 80% homology to any one of SEQ ID NOS:1-3 that retains the ability to bind GATOR2; and
    (ii) a second polypeptide or protein complex comprising the amino acid sequence of: a Sestrin-binding fragment of a GATOR2 (SEQ ID NOS:4-8), or a polypeptide or protein complex having at least 80% homology to SEQ ID NOs:4-8 that retains the ability to bind to at least one of Sestrin1, Sestrin2 or Sestrin3,
under conditions that prevent the first polypeptide from associating with the second polypeptide or protein complex;
  b) incubating the mixture of a) with the test compound; and
determining whether the amount of the first polypeptide associated with the second polypeptide or protein complex is altered in the presence of the test compound as compared to either the absence of the test compound or the presence of a negative control, wherein if the amount of association is increased and/or stabilized the test compound is identified as an inhibitor of mTORC1 activity.

In some embodiments, the invention provides a method of identifying a test compound as a modulator of mTORC1 by determining if the test compound can induce or increase the affinity of Sestrin1 or Sestrin2 for leucine. In one aspect of these embodiments, the method comprises the steps of:
  a) providing a mixture comprising:
    (i) a polypeptide comprising the amino acid sequence of: a leucine binding fragment of Sestrin1 (SEQ ID NO:1) or Sestrin2 (SEQ ID NO:2), or a polypeptide having at least 80% homology to any one of SEQ ID NOS:1-2 that retains the ability to bind leucine; and
    (ii) leucine,
under conditions that allow leucine to bind to the polypeptide;
  b) incubating the mixture of a) with the test compound; and
  c) determining whether the amount of leucine bound to the polypeptide is altered in the presence of the test compound as compared to either the absence of the test compound or the presence of a negative control, wherein if the amount of binding is decreased in the presence of test compound, the test compound is identified as an inhibitor of mTORC1 activity; and if the amount of binding is increased in the presence of the test compound, the test compound is identified as an activator of mTORC1 activity.

In some embodiments, the invention provides a method of identifying a test compound as a modulator of mTORC1 by determining if the test compound can induce or increase the affinity of Sestrin1 or Sestrin2 for leucine. In one aspect of these embodiments, the method comprises the steps of:
  a) providing a mixture comprising:
    (i) a polypeptide comprising the amino acid sequence of: a leucine binding fragment of Sestrin1 (SEQ ID NO:1) or Sestrin2 (SEQ ID NO:2), or a polypeptide having at least 80% homology to any one of SEQ ID NOS:1-2 that retains the ability to bind leucine; and
    (ii) the test compound;
  b) incubating the mixture of a) with leucine under conditions that allow leucine to bind to the polypeptide; and
  c) determining whether the amount of leucine bound to the polypeptide associated is altered in the presence of the test compound as compared to either the absence of the test compound or the presence of a negative control, wherein if the amount of binding is decreased in the presence of test compound, the test compound is identified as an inhibitor of mTORC1 activity; and if the amount of binding is increased in the presence of the test compound, the test compound is identified as an activator of mTORC1 activity.

In other embodiments, the invention provides a method of increasing mTORC1 activity in a cell comprising the step of contacting the cell with an agent that decreases the interaction of a Sestrin with GATOR2.

In still other embodiments, the invention provides a method of treating a disease, condition, or disorder in a subject who would benefit from increased mTORC1 activity comprising the step of administering to the subject an agent that reduces or antagonizes the interaction of a Sestrin with GATOR2.

In other embodiments, the invention provides a method of decreasing mTORC1 activity in a cell comprising the step of contacting the cell with an agent that induces or increases the interaction of a Sestrin with GATOR2 or that reduces the dissociation of a Sestrin with GATOR2 in the presence of leucine.

In still other embodiments, the invention provides a method of treating a disease, condition or disorder in a subject who would benefit from decreased mTORC1 activity comprising the step of administering to the subject an agent that induces or increases the interaction of a Sestrin with GATOR2 or that reduces the dissociation of a Sestrin with GATOR2 in the presence of leucine.

In other embodiments, the invention provides a method of increasing mTORC1 activity in a cell comprising the step of contacting the cell with an agent that increases the binding of leucine to Sestrin1 or Sestrin2.

In still other embodiments, the invention provides a method of treating a disease, condition, or disorder in a subject who would benefit from increased mTORC1 activity comprising the step of administering to the subject an agent that increases the binding of leucine to Sestrin1 or Sestrin2.

In other embodiments, the invention provides a method of decreasing mTORC1 activity in a cell comprising the step of contacting the cell with an agent that decreases the binding of leucine to Sestrin1 or Sestrin2.

In still other embodiments, the invention provides a method of treating a disease, condition or disorder in a subject who would benefit from decreased mTORC1 activity comprising the step of administering to the subject an agent that decreases the binding of leucine to Sestrin1 or Sestrin2.

More specific aspects of these embodiments and additional embodiments are set forth in the Detailed Description of the Invention.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A depicts mass spectrometric analyses identifying Sestrin-derived peptides in immunoprecipitates from HEK-293T cells stably expressing FLAG-tagged GATOR2 components. FIG. 1B depicts an immunoblot for the indicated proteins of anti-FLAG immunoprecipitates collected from HEK-293T cells and cell lysates expressing the indicated cDNAs in expression vectors. FIG. 1C depicts an immunoblot for the indicated proteins of anti-FLAG immunoprecipitates collected from HEK-293T cells and cell lysates stably expressing the indicated FLAG-tagged proteins. FIG. 1D depicts an immunoblot for the indicated proteins of anti-FLAG immunoprecipitates collected from HEK-293T cells and cell lysates stably expressing the indicated FLAG-tagged proteins after the cells were starved of amino acids for 50 minutes, or starved and stimulated with amino acids for 10 minutes. FIG. 1E depicts an immunoblot for the indicated proteins of anti-FLAG immunoprecipitates collected from HEK-293T cells and cell lysates stably expressing the indicated FLAG-tagged proteins after the cells were starved of amino acids for 50 minutes, or starved and stimulated with amino acids for 10 minutes. FIG. 1F depicts an immunoblot for the indicated proteins of anti-FLAG immunoprecipitates collected from HEK-293T cells and cell lysates stably expressing the indicated FLAG-tagged proteins after the cells were starved of either amino acids, glucose, or growth factors for 50 minutes, or starved and restimulated with amino acids, glucose, or insulin, respectively, for 10 minutes.

FIG. 2A, depicts an immunoblot of cell lysates from HEK-293T cells stably expressing the indicated proteins that were starved of amino acids for 50 minutes, or starved and restimulated with amino acids for 10 minutes. FIG. 2B depicts the distribution of cell sizes of HEK-293T cells stably expressing the indicated proteins versus wild-type HEK-293 T cells. FIG. 2C depicts an immunoblot of cell lysates from HEK-293T cells genetically modified with the indicated guide RNAs and the CRISPR/Cas9 system and subsequently treated with the indicated shRNAs, then starved of amino acids for 50 minutes, or starved and restimulated with amino acids for 10 minutes. FIG. 2D depicts the results of quantitative polymerase chain reactions (Q-PCR) on HEK-293T cells genetically modified with the indicated guide RNAs and the CRISPR/Cas9 system and subsequently treated with the indicated shRNAs, then starved of amino acids for 50 minutes, or starved and restimulated with amino acids for 10 minutes.

FIG. 3A depicts an immunoblot of anti-FLAG immunoprecipitates from HEK-293T cells co-transfected with the indicated cDNAs and DNA encoding either Rag GTPase heterodimers containing constitutively active $RagB^{99L}$-$RagC^{75N}$ or the dominant negative $RagB^{54N}$-$RagC^{121L}$. FIG. 3B depicts an immunoblot of lysates from HEK-293E cells stably over expressing the indicated FLAG-tagged proteins with either normal expression of or lacking the indicated GATOR1 component generated via the CRISPR/Cas9 system.

FIG. 4A depicts the immunofluorescence of HEK-293T cells stably expressing the indicated recombinant proteins that were starved or starved and restimulated with amino acids for the indicated times prior to processing for immunofluorescence. FIG. 4B depicts the immunofluorescence of HEK-293T cells stably expressing the indicated shRNA constructs that were starved or starved and restimulated with amino acids for the indicated times prior to processing for immunofluorescence. FIG. 4C depicts the putative pathway for and components associated with mTORC1 modulation and translocation to the lysosome.

FIG. 5A depicts an immunoblot of the indicated proteins of anti-FLAG immunoprecipitates collected from HEK-293T cells and cell lysates stably expressing the indicated FLAG-tagged proteins. FIG. 5B depicts an immunoblot of the indicated proteins of anti-FLAG immunoprecipitates collected from HEK-293T cells and cell lysates expressing the indicated cDNAs in expression vectors. FIG. 5C depicts an immunoblot for the indicated proteins of anti-FLAG immunoprecipitates collected from HEK-293T cells and cell lysates stably expressing the indicated FLAG-tagged proteins after the cells were starved of amino acids for 50 minutes, or starved and stimulated with amino acids for 10 minutes and concurrently treated with either DMSO, the mTORC1 inhibitors 250 nM rapamycin, or 250 nM Torin1 for 60 minutes. FIG. 5D depicts an immunoblot for levels of the indicated endogenous protein in cell lysates from HEK-293T cells genetically modified with the indicated guide RNAs using the CRISPR-Cas9 system. FIG. 5E depicts an immunoblot of the indicated endogenous proteins from anti-FLAG immunoprecipitates from HEK-293T cells expressing the indicated cDNAs.

FIG. 6A depicts an immunoblot for the indicated proteins of cell lysate from HEK-293T cells transiently overexpressing Sestrin1 or Sestrin2 after the cells were starved of amino acids for 50 minutes, or starved and stimulated with amino acids for 10 minutes. FIG. 6B depicts an immunoblot for the indicated proteins from Sestrin2-null HEK-293T cells, or HEK-293T cells that were treated with a guide RNA targeting Green fluorescent protein (GFP) and that were starved of amino acids for 50 minutes, or starved and stimulated with amino acids for 10 minutes. FIGS. 6C-6F depict immunoblots for the indicated proteins from cell lysates from HEK-293T cells that were treated with the indicated shRNAs and starved of amino acids for 50 minutes, or starved and stimulated with amino acids for 10 minutes.

FIG. 7A depicts the immunofluorescence of HEK-293T cells stably overexpressing the indicated recombinant proteins that were starved or starved and restimulated with amino acids for the indicated times prior to processing for immunofluorescence. FIG. 7B depicts the immunofluorescence of Sestrin2 null cells generated by the CRISPR/Cas9 system that had shRNA-mediated knockdown of the indicated gene and were starved or starved and restimulated with amino acids for the indicated times prior to processing for immunofluorescence.

FIG. 8A depicts an immunoblot of HEK-293T cells stably expressing the indicated FLAG-tagged proteins and that were starved of either all amino acids (ALL); only leucine, arginine, and lysine (LRK); only leucine (L); only arginine (R); or only lysine (K) for 50 minutes, or starved for 50 minutes and restimulated for 10 minutes with the indicated amino acids and immunoprecipitated with anti-FLAG resin. The asterisk indicates a non-specific band. FIG. 8B depicts an immunoblot of HEK-293T cells stably expressing the indicated FLAG-tagged proteins and that were starved of all amino acids for 50 minutes. The indicated amino acids were added pre-lysis to the cell culture media or post-lysis to cell lysates prior to FLAG immunoprecipitation. FIG. 8C depicts an immunoblot of HEK-293T cells stably expressing the indicated FLAG-tagged proteins and starved of all amino acids for 50 minutes. FLAG immunoprecipitates were subjected to washes containing the indicated amounts of leucine or arginine in the presence of 0.5 M NaCl.

FIGS. 9A, 9B, 9C, 9D and 9E. FIG. 9A depicts an immunoblot of HEK-293T cells stably expressing the GATOR2 polypeptide FLAG-WDR24 or the control protein FLAG-metap2 that were starved for leucine, arginine, or all amino acids for 50 minutes. Where indicated, cells were re-stimulated with leucine, arginine, or the presence of all 20 amino acids that are found in proteins (hereinafter referred to as "all amino acids") for 10 minutes and FLAG immunoprecipitates prepared from cell lysates. FIG. 9B depicts an immunoblot of cell lysates or culture media from HEK-293T cells stably expressing FLAG-metap2 or FLAG-WDR24 that were starved for 50 minutes for all amino acids. Leucine or arginine was then added to the lysates or medium for 10 minutes and then FLAG immunoprecipitates were prepared from each. FIG. 9C depicts an immunoblot of HEK-293T cells stably expressing FLAG-metap2 or FLAG-WDR24 and starved for 50 minutes for all amino acids. Indicated amino acids (300 µM) were added directly to the FLAG immunoprecipitates. FIG. 9D depicts an immunoblot of HEK-293T cells stably expressing FLAG-metap2 or FLAG-WDR24 and starved for 50 minutes for all amino acids. Varying amounts of leucine were added directly to the FLAG immunoprecipitates as indicated. FIG. 9E depicts an immunoblot of HEK-293T cells stably expressing FLAG-metap2 or FLAG-WDR24 and starved for 50 minutes for all amino acids. Indicated amounts of isoleucine, methionine, leucine or arginine were added directly to the FLAG immunoprecipitates.

FIG. 10A depicts the binding of $^3$H-leucine to various FLAG-tagged and immunoprecipitated proteins and protein complexes produced in HEK-293T cells in the presence or absence of unlabeled leucine. Values are Mean±SD for 3 technical replicates from one representative experiment. FIG. 10B depicts the binding of $^3$H-leucine to various FLAG-tagged and immunoprecipitated Sestrins produced in HEK-293T cells in the presence or absence of unlabeled leucine. FIGS. 10C, 10D, and 10E depict the binding of $^3$H-leucine to FLAG-tagged and immunoprecipitated Sestrin2 produced in HEK-293T cells in the presence of increasing concentrations of leucine (FIG. 10C), methionine (FIG. 10D) or isoleucine (FIG. 10E) and the calculated $K_d$ (FIG. 10C) or $K_i$ (FIGS. 10D and 10E). 10 µM $^3$H-leucine was used in each experiment and each point in the graphs represents the normalized mean±SD from three separate experiments. FIG. 10F depicts the binding of $^3$H-leucine to bacterially produced His-MBP-Sestrin2 or the His-RagA/RagC heterodimer, each of which has been separately bound to a Ni-NTA resin. FIG. 10G depicts thermal shift plots for the binding of bacterially produced His-MBP-Sestrin2 in the presence or absence of various amounts of leucine or arginine.

FIG. 11B depicts an immunoblot of HEK-293T cells stably expressing the indicated FLAG-tagged proteins, which were starved of leucine for 50 minutes and restimulated with leucine at the indicated concentrations for 10 minutes. FIG. 11C depicts an immunoblot of HEK-293T cells transiently expressing FLAG-tagged wild-type Sestrin2 or FLAG-tagged Sestrin2 mutant S190A, which were immunopurified and treated with the indicated concentrations of leucine before immunoblotting. FIG. 11D depicts the binding of $^3$H-leucine to FLAG-tagged and immunoprecipitated wild-type Sestrin2, Sestrin2 mutant S190A or the negative control Rap2A produced in HEK-293T cells in the presence or absence of unlabeled leucine. FIG. 11E depicts an immunoblot of HEK-293T cells transiently expressing FLAG-tagged wild-type Sestrin2, Sestrin2 mutant S190A, or metap2, starved for amino acids for 50 minutes, and where indicated restimulated with amino acids for 10 minutes. Anti-FLAG immunoprecipitates and cell lysates were analyzed. FIG. 11F depicts an anti-FLAG and anti-WDR24 immunoblot of HEK-293T cells transiently expressing untagged WDR24, FLAG-tagged wild-type Sestrin2, FLAG-tagged Sestrin2 mutant S190W, or FLAG-tagged metap2 (as a negative control) which were immunopurified with anti-Flag resin. FIG. 11G depicts the binding of $^3$H-leucine in the presence or absence of unlabeled leucine to FLAG-tagged and immunoprecipitated wild-type Sestrin2, Sestrin2 mutant S190W or the negative control Rap2A produced in HEK-293T cells. FIG. 11H depicts an immunoblot of wild-type or Sestrin1-3 null HEK-293T cells transiently expressing FLAG-tagged wild-type Sestrin2, Sestrin2 mutant S190W, or metap2, starved for leucine for 50 minutes, and where indicated restimulated with leucine for 10 minutes. Cell lysates were analyzed for the indicated proteins and phosphorylation states.

FIG. 12A depicts the binding of $^3$H-leucine to FLAG-tagged and immunoprecipitated Rap2A, Sestrin2, the Sestrin2 mutants L261A and Sestrin2 E451A produced in HEK-293T cells in the presence or absence of unlabeled leucine. FIG. 12B depicts an immunoblot of HEK-293T cells transiently expressing the indicated FLAG-tagged proteins. The immunoprecipitates were treated with the indicated concentrations of leucine prior to immunoblotting. FIG. 12C depicts an immunoblot of lysates from wild-type and Sestrin1-3 null HEK-293T cells transiently expressing the indicated FLAG-tagged proteins after being starved for leucine for 50 minutes and, where indicated, restimulated with leucine for 10 minutes. FIG. 12D-G depict immunofluorescence localization of RagC and/or mTOR in wild-type and Sestrin1-3 null HEK-293T cells transiently expressing the indicated FLAG-tagged proteins after being starved for leucine for 50 minutes and, where indicated, restimulated with leucine for 10 minutes, Immunofluorescence of LAMP2 is used as a control for lysosomal localization.

FIG. 14A depicts western blot detecting FLAG-tagged proteins from HEK-293T cells expressing FLAG-tagged WDR24 starved of amino acids for 60 minutes, lysed, immunoprecipitated with anti-FLAG resin and then incubated with water for the indicated time. FIG. 14B depicts the time course of dissociation of Sestrin2 from the GATOR2 polypeptide WDR24 in the presence of water (negative control) derived from FIG. 14A. FIG. 14C depicts the time course of dissociation of Sestrin2 from GATOR2 in the presence of one of the compounds determined to be a leucine antagonist in FIG. 13.

FIG. 15A depicts a immunoblot of the mTORC1 substrate phosphorylated-S6K (Thr389) and actin from HEK-293T cells starved of leucine for 30 minutes, incubated for 30 minutes with one of the compounds determined to be a leucine antagonist or water (negative control), and then, for some samples, stimulated with leucine. FIG. 15B depicts the actin-normalized pS6K levels for each of the sample groups analyzed in FIG. 15A. An asterisk indicates that the results have a statistical significance of p<0.05 as determined by the student t-test.

FIG. 16A depicts the AlphaLISA® signal from varying amounts of lysate (measured as total protein content) from HEK293T cells stably expressing FLAG-WDR24 and transiently expressing N-terminal tagged HA-Sestrin2, that have been treated with water (negative control) or leucine (positive control) and incubated with FLAG-donor beads and HA-acceptor beads. FIG. 16A (inset) depicts the AlphaLISA® signal from varying amounts of lysate from HEK293T cells stably expressing FLAG-WDR24 and transformed with varying amounts of empty vector. FIG. 16B depicts the AlphaLISA® signal from 6 ng of lysate from HEK293T cells stably expressing FLAG-WDR24 that were transformed with varying amounts of a vector encoding N-terminal tagged HA-Sestrin2 prior to treatment with water or leucine and subsequent incubation with FLAG-donor beads and HA-acceptor beads. FIG. 16C depicts the AlphaLISA® signal from varying amounts of lysate (measured as total protein content) from HEK293T cells stably expressing FLAG-WDR24 and transiently expressing N-terminal tagged HA-Sestrin2, that have been treated with water (negative control) or leucine (positive control), incubated with biotinylated anti-HA antibody and then incubated with FLAG-donor and streptavidin-acceptor beads. FIG. 16D depicts the AlphaLISA® signal from varying amounts of lysate (measured as total protein content) from HEK293T cells stably expressing FLAG-WDR24 and transiently expressing N-terminal tagged HA-Sestrin2, that have been treated with water or water plus a biotinylated HA peptide. Following this treatment, samples are incubated with biotinylated anti-HA antibody, and then incubated with FLAG-donor and streptavidin-acceptor beads.

FIGS. 17A-17K depict exemplary polypeptide sequences of the present invention. FIGS. 17A, 17B, 17C, 17D, 17E and 17F depict exemplary Sestrin polypeptide sequences. FIGS. 17G, 17H, 17I, 17J and 17K depict exemplary polypeptides of the GATOR2 protein complex.

DETAILED DESCRIPTION OF THE INVENTION

Figures 1A, 1B, 1C, 1D, 1E, 1F:
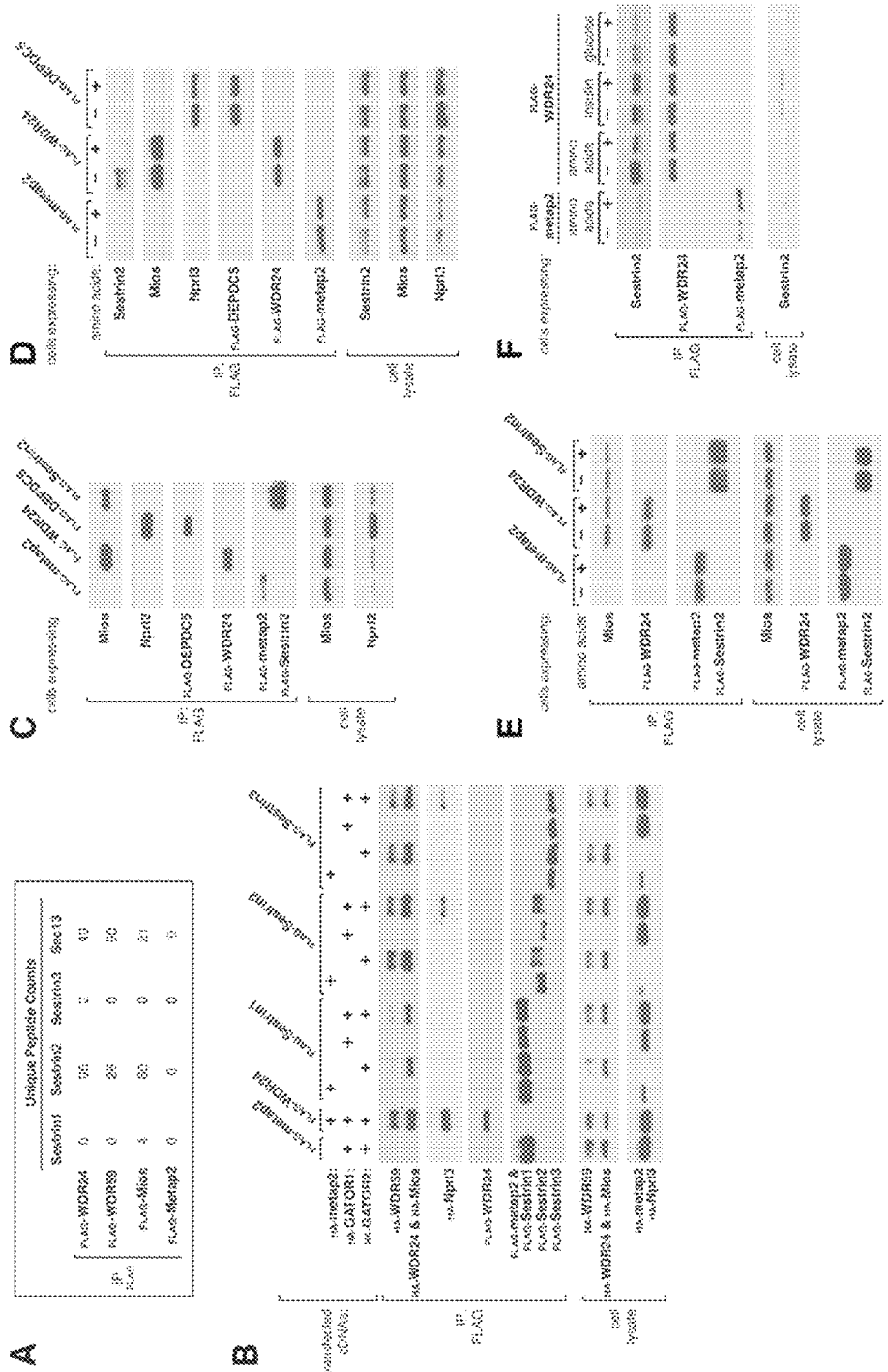
FIGS. 1A, 1B, 1C, 1D, 1E and 1F.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science, and Current Protocols in Cell Biology*, all John Wiley & Sons, N.Y., edition as of December 2008; Sambrook, Russell, and Sambrook, *Molecular Cloning: A Laboratory Manual*, 3$^{rd}$ ed., Cold Spring Harbor Laboratory Press, Cold Spring arbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10$^{th}$ ed. (2006) or 11th edition (July 2009). Non-limiting information regarding genes and genetic disorders is found in McKusick, V.A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

In some embodiments, the invention provides a method of identifying a test compound as an activator of mTORC1 comprising the steps of:

a) providing a mixture comprising:
   (i) a first polypeptide comprising the amino acid sequence of: a GATOR2-binding fragment of Sestrin1 (SEQ ID NO:1), a GATOR2-binding fragment Sestrin2 (SEQ ID NO:2), a GATOR2-binding fragment Sestrin3 (SEQ ID NO:3), or a polypeptide having at least 80% homology to any one of SEQ ID NOS:1-3 that retains the ability to bind GATOR2; and
   (ii) a second polypeptide or protein complex comprising the amino acid sequence of: a Sestrin-binding fragment of a GATOR2 complex (SEQ ID NOS:4-8), or a polypeptide or protein complex having at least 80% homology to SEQ ID NOs:4-8 that retains the ability to bind to at least one of Sestrin1, Sestrin2 or Sestrin3, under conditions that allow the first polypeptide to associate with the second polypeptide or protein complex;

b) incubating the mixture of a) with the test compound; determining whether the amount of the first polypeptide associated with the second polypeptide or protein complex is altered in the presence of the test compound as compared to either the absence of the test compound or the presence of a negative control, wherein if the amount of association is decreased the test compound is identified as an activator of mTORC1 activity.

The term "GATOR2" refers to a protein complex of five different polypeptides: Seh1L (SEQ ID NO:8), WDR59 (SEQ ID NO:7), WDR24 (SEQ ID NO:6), Sec13 (SEQ ID NO:5) and Mios (SEQ ID NO:4).

The term "Sestrin" when used without a further numerical descriptor refers to a polypeptide selected from Sestrin1

("Sestrin1": SEQ ID NO:1), Sestrin2 ("Sestrin2": SEQ ID NO:2), Sestrin3 ("Sestrin3": SEQ ID NO:3), as well as other isoforms of Sestrin1 (SEQ ID NOS:9 and 10) and an isoform of Sestrin3 (SEQ ID NO:11).

The term "GATOR2-binding fragment" refers to the minimal portion of a Sestrin or a polypeptide that is at least 80% homologous to a Sestrin that specifically associates with one or more polypeptides of GATOR2. In some embodiments, a GATOR2-binding fragment is the minimal portion of a Sestrin or a polypeptide that is at least 80% homologous to a Sestrin that primarily associates with WDR24. In some embodiments, a GATOR2-binding fragment is the minimal portion of a Sestrin or a polypeptide that is at least 80% homologous to a Sestrin that primarily associates with Seh1L.

The term "Sestrin binding fragment" refers to the minimal portion of GATOR2 or a polypeptide or protein complex that is at least 80% homologous to GATOR2 that specifically associates with a Sestrin. In some embodiments, a GATOR2-binding fragment is the minimal portion of WDR24 that specifically associates with a Sestrin. In still other embodiments, a GATOR2-binding fragment is the minimal portion of GATOR2 or a polypeptide or protein complex that is at least 80% homologous to GATOR2 that specifically associates with Sestrin2. In yet other embodiments, a GATOR2-binding fragment is the minimal portion of WDR24 that specifically associates with Sestrin2. In still other embodiments, a GATOR2-binding fragment is the minimal portion of GATOR2 or a polypeptide or protein complex that is at least 80% homologous to GATOR2 that specifically associates with Sestrin1.

The term "at least 80% homologous" as used herein with respect to two polypeptide or proteins (the "query" sequence as compared to the "reference" sequence), means at least 80%, 85%, 86%, 87%, 88%, 89%, 90%, 91%, 92%, 93%, 94%, 95%, 96%, 97%, 98%, or 99% identity at an amino acid level as determined conventionally using known sequence alignment computer programs, such as the Bestfit program. When using Bestfit or other sequence alignment programs to determine whether a particular sequence is at least 80% identical to a reference sequence according to the present invention, the parameters are set such that the percentage of identity is calculated over the full length of the portion of the reference amino acid sequence that is homologous to the query sequence. For example, a query polypeptide sequence is at least 80%, 85%, 86%, 87%, 88%, 89%, 90%, 91%, 92%, 93%, 94%, 95%, 96%, 97%, 98%, or 99% identical at the amino acid level to a reference polypeptide sequence over at least 20%, 30%, 40%, 50%, 60%, 70%, 80%, 90%, 95%, 96%, 97%, 98%, 99%, or 100% of the reference polypeptide sequence.

"Conditions that allow the first polypeptide to associate with the second polypeptide or protein complex" generally include a buffered solution at physiological pH and salt concentrations characterized by the absence of compounds known to inhibit the Sestrin-GATOR2 interaction. Exemplary conditions are those that are substantially free of leucine and/or isoleucine and/or analogs of leucine or isoleucine. In certain embodiments, such conditions are less than 1 nM of leucine and/or isoleucine and/or analogs of leucine or isoleucine. In certain embodiments, such conditions are 100% free of leucine and/or isoleucine and/or analogs of leucine or isoleucine. "Analogs" include modified versions of leucine or isoleucine, such as norleucine, threo-L-beta-hydroxyleucine, H-alpha-methyl-D/L-leucine, S-(−)-2-amino-4-pentenoic acid, 3-amino-4-methylpentanoic acid, and leucine-amide hydrochloride (H-Leu-NH$_2$HCl); as well as compounds identified by the assays of the invention as inhibitors of Sestrin-GATOR2 interaction. The term "substantially free" as used herein with respect to leucine and/or analogs of leucine means a concentration of less than 100 nM. The term "substantially free" as used herein with respect to isoleucine and/or analogs of isoleucine means a concentration of less than 1 µM.

The term "test compound" refers to any of a small molecule, nucleic acid, amino acid, polypeptide, antibody and antibody-like molecules, aptamers, macrocycles, or other molecules. In certain embodiments, a test compound is a small organic molecule. In one aspect of these embodiments, the small organic molecule has a molecular weight of less than about 5,000 daltons. In certain embodiments, the test compound is other than an amino acid. In other embodiments, the small molecule is other than leucine, isoleucine or analogs of either of the foregoing.

In some embodiments, the first polypeptide used in the method comprises the amino acid sequence of a GATOR2-binding fragment of any of Sestrin1 (SEQ ID NO:1), Sestrin2 (SEQ ID NO:2), Sestrin3 (SEQ ID NO:3), or isoforms thereof (SEQ ID NOS:9-11). In a more specific aspect of these embodiments, the first polypeptide comprises the amino acid sequence of a GATOR2-binding fragment of Sestrin2 (SEQ ID NO:2). In another more specific aspect of these embodiments, the first polypeptide comprises the amino acid sequence of a GATOR2-binding fragment of Sestrin1 (SEQ ID NO:1).

In certain embodiments, the first polypeptide comprises an amino acid sequence that is at least 80%, 85%, 86%, 87%, 88%, 89%, 90%, 91%, 92%, 93%, 94%, 95%, 96%, 97%, 98%, or 99% identical to a GATOR2-binding fragment of Sestrin1 (SEQ ID NO: 1) over at least 20%, 30%, 40%, 50%, 60%, 70%, 80%, 90%, 95%, 96%, 97%, 98%, 99%, or 100% of the GATOR2-binding fragment of Sestrin1 (SEQ ID NO: 1) and retains the ability to bind GATOR2.

In certain embodiments, the first polypeptide comprises an amino acid sequence that is at least 80%, 85%, 86%, 87%, 88%, 89%, 90%, 91%, 92%, 93%, 94%, 95%, 96%, 97%, 98%, or 99% identical to a GATOR2-binding fragment of Sestrin2 (SEQ ID NO: 2) over at least 20%, 30%, 40%, 50%, 60%, 70%, 80%, 90%, 95%, 96%, 97%, 98%, 99%, or 100% of the GATOR2-binding fragment of Sestrin2 (SEQ ID NO: 2) and retains the ability to bind GATOR2.

In certain embodiments, the first polypeptide comprises an amino acid sequence that is at least 80%, 85%, 86%, 87%, 88%, 89%, 90%, 91%, 92%, 93%, 94%, 95%, 96%, 97%, 98%, or 99% identical to a GATOR2-binding fragment of Sestrin3 (SEQ ID NO: 3) over at least 20%, 30%, 40%, 50%, 60%, 70%, 80%, 90%, 95%, 96%, 97%, 98%, 99%, or 100% of the GATOR2-binding fragment of Sestrin3 (SEQ ID NO: 3) and retains the ability to bind GATOR2.

In certain embodiments, the second polypeptide or protein complex comprises an amino acid sequence that is at least 80%, 85%, 86%, 87%, 88%, 89%, 90%, 91%, 92%, 93%, 94%, 95%, 96%, 97%, 98%, or 99% to a Sestrin-binding fragment of a GATOR2 complex (SEQ ID NOs: 4-8) over at least 20%, 30%, 40%, 50%, 60%, 70%, 80%, 90%, 95%, 96%, 97%, 98%, 99%, or 100% of the Sestrin-binding fragment of the GATOR2 complex (SEQ ID NOs: 4-8) and retains the ability to bind to at least one of Sestrin1, Sestrin2 and/or Sestrin3.

In other embodiments, the second polypeptide or protein complex comprises the amino acid sequence of a Sestrin-binding fragment of a GATOR2 complex (SEQ ID NOS:4-8). In a more specific aspect of these embodiments, the second polypeptide or protein complex comprises the amino acid sequence of a Sestrin-binding fragment of WDR24 (SEQ ID NO:4). In a more specific aspect of these embodiments, the second polypeptide or protein complex comprises the amino acid sequence of a Sestrin-binding fragment of Seh1L (SEQ ID NO:8).

In still other embodiments, the first polypeptide comprises an amino acid sequence selected from any one of SEQ ID NO:1, SEQ ID NO:2, SEQ ID NO:3, SEQ ID NO:9, SEQ ID NO:10, or SEQ ID NO:11; and the second polypeptide comprises an amino acid sequence selected from any one of SEQ ID NO:4, SEQ ID NO:5, SEQ ID NO:6, SEQ ID NO:7 or SEQ ID NO:8. In a more specific aspect of these embodiments, the first polypeptide comprises the amino acid sequence of Sestrin2 (SEQ ID NO:2). In another more specific aspect of these embodiments, the second polypeptide comprises the amino acid sequence of WDR24 (SEQ ID NO:4). In an even more specific aspect of these embodiments, the first polypeptide comprises the amino acid sequence of Sestrin2 (SEQ ID NO:2) and the second polypeptide comprises the amino acid sequence of WDR24 (SEQ ID NO:4). In another even more specific aspect of these embodiments, the first polypeptide comprises the amino acid sequence of Sestrin2 (SEQ ID NO:2) and the second polypeptide comprises the amino acid sequence of Seh1L (SEQ ID NO:8).

The determination of whether the amount of the first polypeptide associated with the second polypeptide or protein complex is altered in the presence of the test compound is typically achieved by distinguishing between the first polypeptides associated with the second polypeptides or protein complexes and the first polypeptides that are not associated with the second polypeptides or protein complexes. One way of achieving such differentiation is by binding a tag to at least one of the first or second polypeptide or protein complex and then detecting at least one of the bound tags or a product of the first and second tags. Other ways of achieving such differentiation includes, but is not limited to, separation techniques, such as gel filtration (size exclusion chromatography; non-denaturing gel electrophoresis) and differential centrifugation; and size determination, such as mass spectrometry.

The term "tag" as used herein includes, but is not limited to, detectable labels, such as fluorophores, radioisotopes, colorimetric substrates, or enzymes; heterologous epitopes for which specific antibodies are commercially available, e.g., FLAG-tag; heterologous amino acid sequences that are ligands for commercially available binding proteins, e.g., Strep-tag, biotin; fluorescence quenchers typically used in conjunction with a fluorescent tag on the other polypeptide; and complementary bioluminescent or fluorescent polypeptide fragments. A tag that is a detectable label or a complementary bioluminescent or fluorescent polypeptide fragment may be measured directly (e.g., by measuring fluorescence or radioactivity of, or incubating with an appropriate substrate or enzyme to produce a spectrophotometrically detectable color change for the associated polypeptides as compared to the unassociated polypeptides). A tag that is a heterologous epitope or ligand is typically detected with a second component that binds thereto, e.g., an antibody or binding protein, wherein the second component is associated with a detectable label. A tag, e.g., a heterologous epitope, may also be used to affix or immobilize the polypeptide to which it is bound to a solid support.

As used herein, the term "immobilize" in the context of an immobilized polypeptide or protein complex, refers to a substance that is affixed (e.g., tethered) to a substrate or support (e.g., a solid support), and not free in solution.

The term "solid support" is defined as a solid material of any size, shape, composition or construction that is suitable as an attachment material for any polypeptide or protein complex utilized in the present invention.

Thus, in certain embodiments of the methods described above: the first polypeptide is optionally bound to a first tag; the second polypeptide or protein complex is optionally bound to a second tag; at least one of the first polypeptide or the second polypeptide or protein complex is bound to its corresponding tag; and determining the amount of the first polypeptide associated with the second polypeptide or protein complex: (a) comprises detecting at least one of the first or second tag or a product of the first and second tag; and (b) distinguishes between the first polypeptide associated with the second polypeptide or protein complex and the first polypeptide not associated with the second polypeptide or protein complex.

In certain aspects of the embodiment in which at least one of the first polypeptide or the second polypeptide or protein complex is bound to its corresponding tag: the first tag is present and comprises a first epitope not naturally present in any of Sestrin1 (SEQ ID NO:1), Sestrin2 (SEQ ID NO:2), or Sestrin3 (SEQ ID NO:3); the second tag is present and comprises a second epitope not naturally present in any GATOR2 complex (SEQ ID NOS:4-8); detecting the first tag comprises binding a first antibody specific for the first epitope; and detecting the second tag comprises binding a second antibody specific for the second epitope. For the sake of clarity in these aspects, although both the first and the second tags are present, it is not required that both tags be detected, nor that both the first and second antibody be used for detection. Some of the assays that fall under these aspects use only one antibody and detect only one tag. The other tag may be used to affix or immobilize the polypeptide to which it is bound to a solid support.

In other aspects of the embodiment in which at least one of the first polypeptide or the second polypeptide or protein complex is bound to its corresponding tag one of the first polypeptide or second polypeptide or protein complex is immobilized on a solid support. In a more specific aspect, the immobilization on the solid support is mediated through the corresponding tag. In one example, the solid support is a bead or plate coated with an antibody that recognizes the tag, resulting in the tethering of the tagged polypeptide or protein complex to the bead or plate.

In still another aspect of the embodiment in which at least one of the first polypeptide or the second polypeptide or protein complex is bound to its corresponding tag, only one of the first antibody or the second antibody is used for detection of the first or second tag, and the antibody used for detection is conjugated to a detectable label.

In yet another aspect, both the first and second tags are present and are each members of a proximity fluorescence reagent pair. The term "proximity fluorescence reagent pair" refers to two reagents that react with one another to produce detectable fluorescence or phosphorescence when they are in close proximity, e.g., when the two polypeptides to which they are attached are associated with one another. Examples of proximity fluorescence reagent pair that may be utilized in this aspect are donor-acceptor FRET pairs that are well-known in the art and commercially available (e.g., cyan fluorescent protein/yellow fluorescent protein; luciferase/yellow fluorescent protein; blue fluorescent protein/green fluorescent protein 2; dansyl/FITC; Cy3/Cy5; and carboxyfluorescein succinimidyl ester/Texas Red); and bimolecular fluorescence complementation (BiFC) pairs.

In a related aspect, both the first and the second tags are present; the first and second antibodies are both utilized to detect the association of the first polypeptide and the second polypeptide or protein complex; and the first and second antibodies are each conjugated to a different member of a proximity fluorescence reagent pair.

In still another aspect, only one of the first tag or second tag is present; the tag present is a fluorescent moiety bound to the N- or C-terminus of the first polypeptide or the second polypeptide; and detecting the association of the first polypeptide with the second polypeptide or protein complex comprises solution phase fluorescence polarization. In a more specific aspect the tag is 5-carboxyfluorescein attached to the N- or C-terminus of the first or second polypeptide.

In yet another aspect, one of the first polypeptide or second polypeptide or protein complex is immobilized on a solid support; and detecting the association of the first polypeptide with the second polypeptide or protein complex comprises surface plasmon resonance (SPR). The immobilization can occur through direct amine coupling of the protein or through the addition of an avidity-tag such as biotin and tethering the tagged protein to a streptavidin coated matrix.

In other embodiments, the invention provides a method of identifying a test compound as an inhibitor of mTORC1 activity comprising the steps of:
  a) providing a mixture comprising:
    (i) a first polypeptide comprising the amino acid sequence of: a GATOR2-binding fragment of Sestrin1 (SEQ ID NO:1), a GATOR2-binding fragment of Sestrin2 (SEQ ID NO:2), a GATOR2-binding fragment of Sestrin3 (SEQ ID NO:3), or a polypeptide having at least 80% homology to any one of SEQ ID NOS:1-3 that retains the ability to bind GATOR2; and
    (ii) a second polypeptide or protein complex comprising the amino acid sequence of: a Sestrin-binding fragment of a GATOR2 complex (SEQ ID NOS:4-8), or a polypeptide or protein complex having at least 80% homology to SEQ ID NOs:4-8 that retains the ability to bind to at least one of Sestrin1, Sestrin2 or Sestrin3,
  under conditions that prevent the first polypeptide from associating with the second polypeptide or protein complex;
  b) incubating the mixture of a) with the test compound;
  c) determining whether the amount of the first polypeptide associated with the second polypeptide or protein complex is altered in the presence of the test compound as compared to either the absence of the test compound or the presence of a negative control, wherein if the amount of association is increased the test compound is identified as an inhibitor of mTORC1 activity.

"Conditions that prevent the first polypeptide from associating with the second polypeptide or protein complex" typically mean the presence of leucine, methionine, valine and/or isoleucine, but also include the presence of other agents known to prevent such association. These other agents may be identified in the assays described above. In one aspect, the assays for identifying inhibitors of association are done in the presence of leucine.

Each of the specific embodiments and aspects set forth above for the method of identifying a test compound as an activator of mTORC1 are also applicable to the method of identifying a test compound as an inhibitor of mTORC1.

In other embodiments, the invention provides a method of identifying a test compound as a modulator of mTORC1 by determining if the test compound can modulate the affinity of Sestrin1 or Sestrin2 for leucine. In one aspect of these embodiments, the method comprises the steps of:
  a) providing a mixture comprising:
    (i) a polypeptide comprising the amino acid sequence of: a leucine binding fragment of Sestrin1 (SEQ ID NO:1) or Sestrin2 (SEQ ID NO:2), or a polypeptide having at least 80% homology to any one of SEQ ID NOS:1-2 that retains the ability to bind leucine; and
    (ii) leucine,
  under conditions that allow leucine to bind to the polypeptide;
  b) incubating the mixture of a) with the test compound; and
  c) determining whether the amount of leucine bound to the polypeptide associated is altered in the presence of the test compound as compared to either the absence of the test compound or the presence of a negative control, wherein if the amount of binding is decreased in the presence of test compound, the test compound is identified as an inhibitor of mTORC1 activity; and if the amount of binding is increased in the presence of the test compound, the test compound is identified as an activator of mTORC1 activity.

In another related aspect of these embodiments, the method comprises the steps of:
  a) providing a mixture comprising:
    (i) a polypeptide comprising the amino acid sequence of: a leucine binding fragment of Sestrin1 (SEQ ID NO:1) or Sestrin2 (SEQ ID NO:2), or a polypeptide having at least 80% homology to any one of SEQ ID NOS:1-2 that retains the ability to bind leucine; and
    (ii) the test compound;
  b) incubating the mixture of a) with leucine under conditions that allow leucine to bind to the polypeptide; and
  c) determining whether the amount of leucine bound to the polypeptide associated is altered in the presence of the test compound as compared to either the absence of the test compound or the presence of a negative control, wherein if the amount of binding is decreased in the presence of test compound, the test compound is identified as an inhibitor of mTORC1 activity; and if the amount of binding is increased in the presence of the test compound, the test compound is identified as an activator of mTORC1 activity.

In certain aspects of the above embodiments, the leucine utilized for determining if the test compound can modulate the affinity of Sestrin1 or Sestrin2 for leucine is tagged with a detectable label. In one aspect of these embodiments, the leucine is tagged with a radiolabel, such as $^3$H. In another aspect of these embodiments, the method additionally comprises the step of separating polypeptide-bound tagged leucine from free tagged leucine prior to determining the amount of leucine bound to the polypeptide. This may be achieved by method well known in the art, including the immobilization of any polypeptide-leucine complexes to a solid support via an immobilized antibody specific to the polypeptide. Once the separation of bound and free leucine has been achieved, radioactivity of the bound portion can be measured and compared to polypeptide-bound leucine in the absence of test compound or the presence of a negative control compound.

In still other embodiments, the invention provides a method of increasing mTORC1 activity in a cell by contacting the cell with an agent that inhibits or reduces the interaction of a Sestrin (e.g., Sestrin1, Sestrin2 or Sestrin3) with the GATOR2 complex.

In still other embodiments, the invention provides a method of increasing mTORC1 activity in a cell by contacting the cell with an agent that increases the binding of leucine by Sestrin1 or Sestrin2.

In other embodiments, the invention provides a method of treating a disease, condition or disorder in a subject which would benefit by activating mTORC1 activity in a subject comprising the step of administering to the subject an agent that reduces or antagonizes the interaction of a Sestrin with the GATOR2 complex. In related embodiments, the invention provides a method of treating a disease, condition or disorder in a subject which would benefit by activating mTORC1 activity in a subject comprising the step of administering to the subject an agent that increases the binding of leucine by Sestrin1 or Sestrin2. In one aspect of either of these embodiments, the disease, condition or disorder is selected from those resulting in skeletal muscle atrophy (such as sarcopenia, muscle denervation, prolonged immobilization and muscular dystrophy), decreased satiety (e.g., cachexia and anorexia), ribosomopathies (e.g. Diamond-Blackfan anemia, 5q-syndrome, Shwachman-Diamond syndrome, X-linked dyskeratosis, cartilage hair hypoplasia, and Treacher Collins syndrome) and cohesinopathies (e.g. Roberts syndrome and Cornelia de Lange syndrome).

Agents that are useful in the above-described methods of increasing mTORC1 activation include test compounds identified by the mTORC1 activator identification assays set forth herein. In some embodiments, the agent is other than leucine. In some embodiments, the agent is other than a naturally occurring amino acid. In some embodiments, the agent is other than an amino acid.

In still other embodiments, the invention provides a method of inhibiting or decreasing mTORC1 activity in a cell by contacting the cell with an agent that induces or increases the interaction of a Sestrin (e.g., Sestrin1, Sestrin2 or Sestrin3) with the GATOR2 complex, or that prevents the dissociation of a Sestrin with GATOR2 in the presence of leucine.

In still other embodiments, the invention provides a method of inhibiting or decreasing mTORC1 activity in a cell by contacting the cell with an agent that decreases the binding of leucine by Sestrin1 or Sestrin2.

In other embodiments, the invention provides a method of treating a disease, condition or disorder in a subject which would benefit by inhibiting or decreasing mTORC1 activity in a subject comprising the step of administering to the subject an agent that induces or increases the interaction of a Sestrin with the GATOR2 complex, or that prevents the dissociation of a Sestrin with GATOR2 in the presence of leucine. In other related embodiments, the invention provides a method of treating a disease, condition or disorder in a subject which would benefit by inhibiting or decreasing mTORC1 activity in a subject comprising the step of administering to the subject an agent that decreases the binding of leucine by Sestrin1 or Sestrin2. In one aspect of either of these embodiments, the disease, condition or disorder is selected from a metabolic disease (e.g., type 2 diabetes, obesity, non-alcoholic steatohepatitis (NASH), and hyperlipidemia), a neurodegenerative disease (e.g., Alzheimer's disease, Parkinson's Disease, Huntington's Disease, and amyotrophic lateral sclerosis), an autoimmune disease (e.g., psoriasis, rheumatoid arthritis, multiple sclerosis, systemic lupus erythematosus, gout, allergic rhinitis, Crohn's Disease, and ulcerative colitis), rare and mitochondrial disease (e.g., Leigh's Syndrome, Friedreich's Ataxia Cardiomyopathy, Leber's Hereditary Optic Neuropathy, lymphangioleiomyomatosis, tuberous sclerosis, Pompe Disease (Glycogen storage disease II), and lysosomal storage diseases), cardiovascular disease (e.g., cardiomyopathy, heart failure, ischemic heart disease (atherosclerotic disease), ischemic stroke, and pulmonary arterial hypertension), renal disease (e.g., diabetic nephropathy, polycystic kidney disease, and acute kidney injury), neuropsychiatric disease (e.g., epilepsy, autism spectrum disorder, and depressive disorder), ontological disease (e.g., renal cell carcinoma, solid tumors, hematological cancers), and improving immune response to vaccines and other medically important uses in cases of a suppressed immune system such as age-related immunosenescence and cancer immunotherapy.

Agents that are useful in the above-described methods of decreasing or inhibiting mTORC1 activity include test compounds identified by the mTORC1 inhibitor identification assays set forth herein. Other agents that are useful in the above-described methods of decreasing mTORC1 activation include agents that mimic amino acid starvation and/or glucose starvation. Such agents may be confirmed as increasing Sestrin-GATOR2 interaction through testing in the mTORC1 inhibitor identification assays of the invention.

EXAMPLES

Example 1

Transfection and Lysis of Recombinant HEK-293 Cells

HEK-293T and HEK-293E cells were cultured in DMEM with 10% IFS supplemented with 2 mM glutamine. All cell lines were maintained at 37° C. and 5% $CO_2$.

Two million HEK-293T cells were plated in 10 cm culture dishes and grown. Twenty-four hours later, cells were transfected via the polyethylenimine method (Boussif et al., 1995) with one or more of the pRK5-based cDNA expression plasmids in the following amounts: 300 ng FLAG-Metap2, 100 ng FLAG-WDR24, 50 ng FLAG-Sestrin1, 25 ng FLAG-Sestrin2, 200 ng FLAG-Sestrin3, 2 ng of FLAG-S6K1, or 200 ng each of HA-Mios, HA-WDR59, HA-WDR24, HA-Sec13, HA-Seh1L, HA-Depdc5, HA-Npr13, or HA-Npr12. The total amount of plasmid DNA in each transfection was normalized to 5 μg with empty pRK5.

Thirty-six hours after transfection, cells were rinsed once with ice-cold PBS and lysed immediately with Triton lysis buffer (1% Triton, 10 mM β-glycerol phosphate, 10 mM pyrophosphate, 40 mM Hepes pH 7.4, 2.5 mM $MgCl_2$ and 1 tablet of EDTA-free protease inhibitor (Roche) (per 25 ml buffer). The cell lysates were clarified by centrifugation at 13,000 rpm at 4° C. in a microcentrifuge for 10 minutes. For anti-FLAG-immunoprecipitations, FLAG-M2 affinity gel (Sigma-Aldrich) was washed with lysis buffer 3 times. Then 30 μl of a 50% slurry of the affinity gel was added to cleared cell lysates and incubated with rotation for 2 hours at 4° C. The beads were washed 3 times with lysis buffer containing 500 mM NaCl. In the case of transient cotransfection assays to explore the interaction of the Sestrins with GATOR2, beads were incubated in the final salt wash for 30 minutes to reduce non-specific binding.

Immunoprecipitated proteins were denatured by the addition of 50 μl of sample buffer and boiling for 5 minutes as described (Kim et al., 2002), resolved by 8%-16% SDS-PAGE, and analyzed by immunoblotting using the appropriate antibody (antibodies to phospho-T389 S6K1, S6K1, Sestrin2, mTOR, Mios and FLAG all obtained from Cell Signaling Technology; antibodies to WDR24 and WDR59 were generously provided by Jianxin Xie at Cell Signaling Technology).

For mass spectrometry, immunoprecipitates from HEK-293T cells stably expressing FLAG-Metap2, FLAG-Mios, FLAG-WDR24 or FLAG-WDR59 were prepared using Triton or Chaps lysis buffer without crosslinking. Proteins were eluted from the FLAG-M2 affinity gel using the FLAG peptide, resolved on 4-12% NuPage gels (Invitrogen), and stained with simply blue stain (Invitrogen). Each gel lane was sliced into 10-12 pieces and the proteins in each gel slice digested overnight with trypsin. The resulting digests were analyzed by mass spectrometry as described (Sancak et al., 2008).

In mass spectrometric analyses of anti-FLAG immunoprecipitates prepared from HEK-293T cells stably expressing FLAG-tagged GATOR2 components (WDR24, Mios, or WDR59), we consistently detected peptides derived from Sestrin2, at levels comparable to those from the bona fide GATOR2 component Sec13 (FIG. 1A). Sestrin1 and Sestrin3 were also present, albeit at lower amounts than Sestrin2 (FIG. 1A).

Figures 5A, 5B, 5C, 5D, 5E:
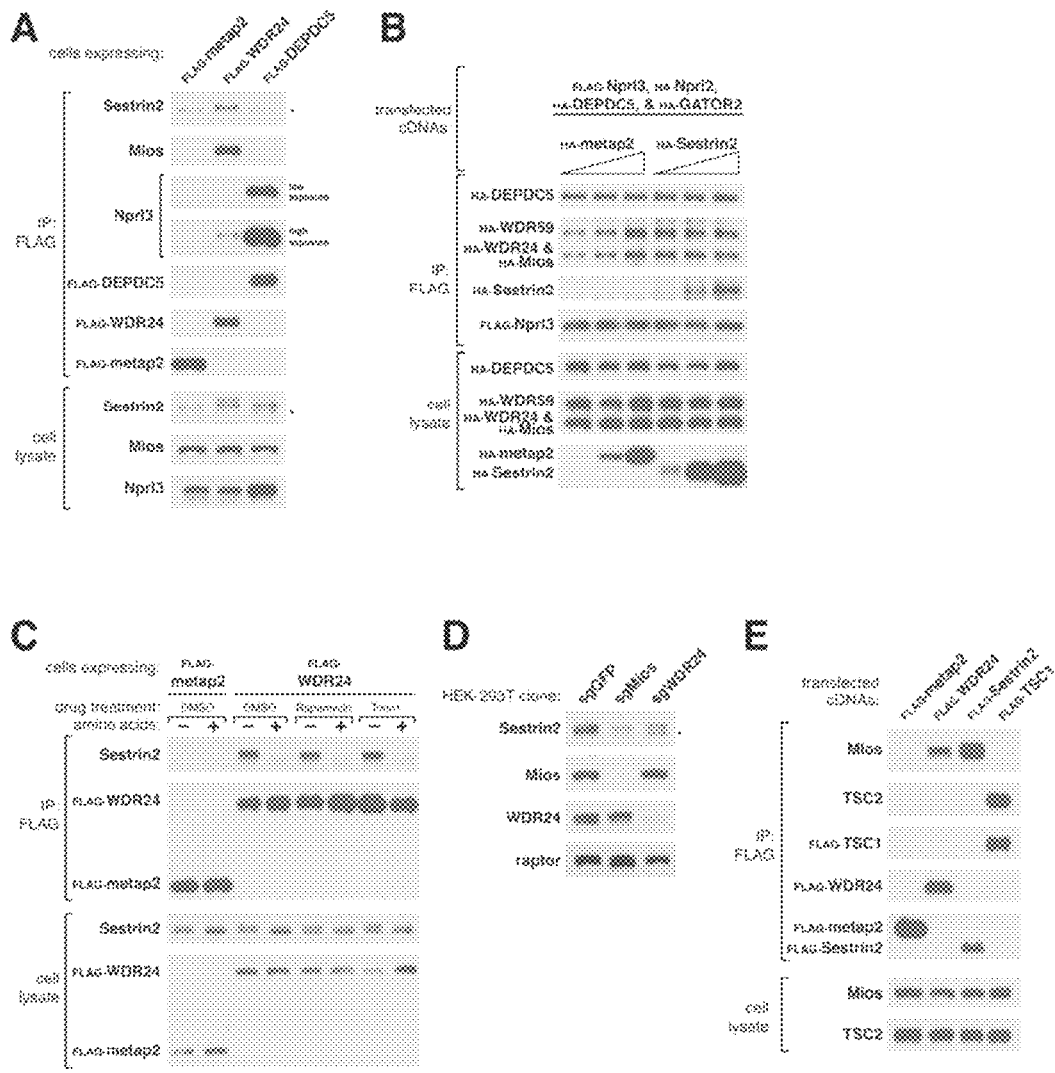
FIGS. 5A, 5B, 5C, 5D and 5E.

Consistent with the Sestrins being GATOR2-interacting proteins, when transiently co-expressed in HEK-293T cells recombinant, FLAG-tagged Sestrin1, Sestrin2, or Sestrin3 co-immunoprecipitated GATOR2, but not GATOR1 or the metap2 control protein (FIG. 1B). When stably expressed in HEK-293T cells, FLAG-Sestrin2 co-immunoprecipitated endogenous GATOR2 as detected through its Mios components (FIG. 1C). The converse was also true because stably expressed FLAG-WDR24 co-immunoprecipitated abundant amounts of endogenous Sestrin2 alongside the established components of GATOR2 (FIG. 5A). In contrast, FLAG-DEPDC5, a GATOR1 component, did not co-immunoprecipitate endogenous Sestrin2, suggesting that GATOR1 and Sestrin2 do not make a readily detectable interaction (FIG. 5A). Given that GATOR1 is known to interact with GATOR2 (Bar-Peled et al., 2013), we tested the effect of expressing increasing amounts of FLAG-Sestrin2 on this interaction and found that Sestrin2 did not perturb the ability of GATOR1 to co-immunoprecipitate GATOR2 (FIG. 5B).

Example 2

Effect of Amino Acids on GATOR2-Sestrin Interaction

In order to determine the effect of amino acids on the GATOR2-Sestrin interaction, transfected cells were incubated in amino acid free RPMI for 50 minutes and then stimulated with amino acids for 10 minutes. For glucose starvation, cells were incubated in RPMI media lacking glucose but containing amino acids and dialyzed serum for 50 minutes, followed by a 10 minute restimulation with 5 mM D-Glucose. For insulin deprivation, cells were incubated in RPMI without serum for 50 minutes and restimulated with 1 µg/ml insulin for 10 minutes. Finally, when Torin1 or Rapamycin was used, cells were incubated with 250 nM of each throughout the starvation and restimulation period.

Amino acids regulate the interaction between multiple critical components of the amino acid pathway (Bar-Peled et al., 2012; Sancak et al., 2010b; Sancak et al., 2008; Tsun et al., 2013; Zoncu et al., 2011). Likewise, amino acid deprivation strongly increased the GATOR2-Sestrin2 interaction, whether monitored by immunoprecipitating GATOR2 or Sestrin2 and probing for endogenous Sestrin2 or GATOR2, respectively (FIGS. 1D and 1E). Pretreatment of cells with rapamycin, an allosteric mTORC1 inhibitor, or Torin1, an ATP-competitive mTOR inhibitor, did not prevent the amino acid-induced decrease in the GATOR2-Sestrin2 interaction, indicating that mTORC1 activity does not control the interaction (FIG. 5C). Consistent with the notion that the pathways upstream of mTORC1 that sense amino acids and growth factors are largely independent, insulin treatment of cells did not regulate the Sestrin2-GATOR2 interaction (FIG. 1E). Interestingly, however, glucose deprivation led to a modest increase in the amount of Sestrin2 bound to GATOR2, albeit to a much lesser extent than that caused by amino acid starvation (FIG. 1E). Glucose levels have been previously described as upstream to the Ragulator-v-ATPase input to Rag GTPases (Efeyan et al., 2012a), and these results are consistent with glucose also affecting the GATOR2 input to the Rag GTPases.

Example 3

Effect of GATOR2 Expression Level on Sestrin Expression

Given the robust interaction between Sestrin2 and GATOR2, we reasoned that within cells the levels of GATOR2 might affect those of Sestrin2, in an analogous fashion to the components of other complexes, like Ragulator or GATOR1 (Bar-Peled et al., 2013; Sancak et al., 2008). In order to explore this question, we used CRISPR/Cas9-mediated genome editing to reduce expression of either the Mios or WDR24 components of GATOR2.

To generate HEK-293T cells with loss of GATOR2 components or Sestrin2, the following sense (S) and antisense (AS) oligonucleotides encoding the guide RNAs were cloned into the pX330 vector (Petit et al., 2013).

```
                             (SEQ ID NO: 12)
sgMios_1S:    caccgATCACATCAGTAAACATGAG (SEQ ID NO: 13)
sgMios_1AS:   aaacCTCATGTTTACTGATGTGATc (SEQ ID NO: 14)
sgWDR24_1S:   caccgACCCAGGGCTGTGGTCACAC (SEQ ID NO: 15)
sgWDR24_1AS:  aaacGTGTGACCACAGCCCTGGGTc (SEQ ID NO: 16)
sgWDR59_1S:   caccgCGGGGGAGATGGCGGCGCGA (SEQ ID NO: 17)
sgWDR59_1AS:  aaacTCGCGCCGCCATCTCCCCCGc (SEQ ID NO: 18)
sgGFP_1S:     caccgTGAACCGCATCGAGCTGAA (SEQ ID NO: 19)
sgGFP_1AS:    aaacTTCAGCTCGATGCGGTTCAc (SEQ ID NO: 20)
sgNpr13_1S:   caccGGCTTTCAGGCTCCGTTCGA (SEQ ID NO: 21)
sgNpr13_1AS:  aaacTCGAACGGAGCCTGAAAGCC
```

On day one, 200,000 HEK-293T cells were seeded into 6 wells of a 6-well plate. Twenty-four hours post seeding, each well was transfected with 250 ng shGFP pLKO (RNAi Consortium; Broad Institute), 1 µg of the pX330 guide construct, and 0.5 µg of empty pRK5 using XtremeGene9 (Roche). The following day, cells were trypsinized, pooled in a 10 cm dish, and selected with puromycin to eliminate untransfected cells. Forty-eight hours after selection, the media was aspirated and replenished with fresh media lacking puromycin. The following day, cells were single cell sorted with a flow cytometer into the wells of a 96-well plate containing 150 ul of DMEM (SAFC Biosciences) supplemented with 30% IFS (Invitrogen). Cells were grown for two weeks and the resultant colonies were trypsinized and expanded. Clones were validated for loss of the relevant protein via immunoblotting.

We found that endogenous Sestrin2 expression was severely depressed in cells that strongly suppressed either the Mios or WDR24 components of GATOR2 via CRISPR/Cas9-mediated genome editing (FIG. 5D). These results identify the Sestrins as GATOR2 interacting proteins, and establish that Sestrin2 and GATOR2 interact in an amino acid-sensitive fashion, suggesting a regulatory role for the Sestrins in signaling amino acid sufficiency to mTORC1.

Example 4

Effect of Sestrins on the Amino Acid Sensing Pathway of mTORC1

Figures 2A, 2B, 2C, 2D:
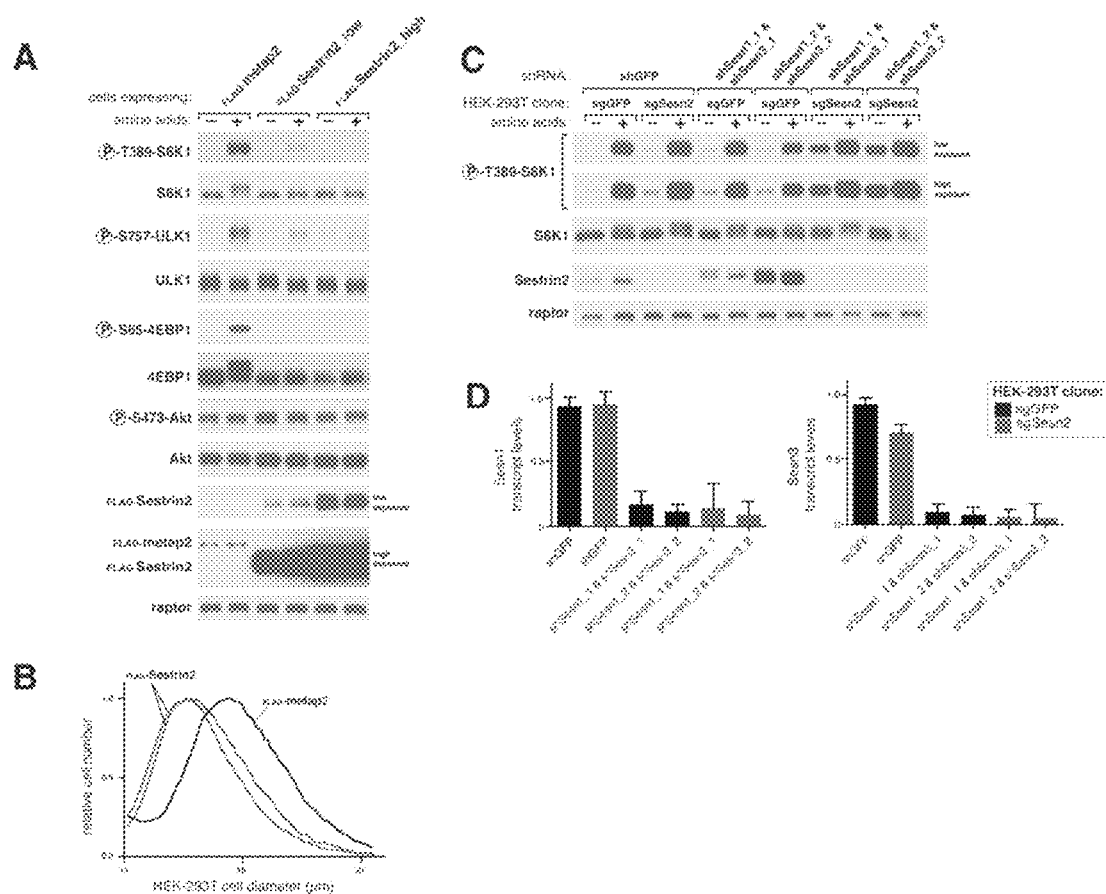
FIGS. 2A, 2B, 2C and 2D.
Figures 6A, 6B, 6C, 6D, 6E, 6F:
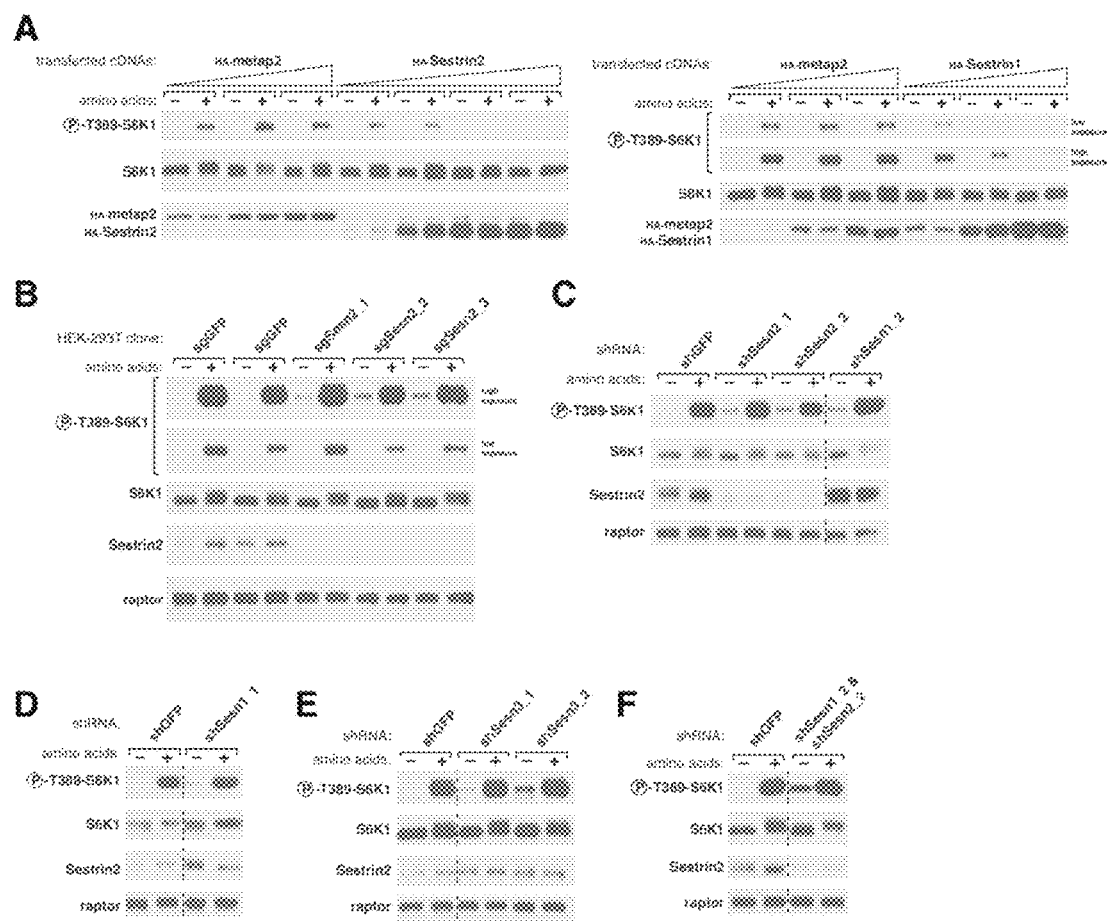
FIGS. 6A, 6B, 6C, 6D, 6E and 6F.

The Sestrins have previously been reported to be negative regulators of mTORC1 signaling and to function by activating AMPK, which in turn stimulates TSC to inhibit Rheb and by binding TSC (Budanov and Karin, 2008). In our experimental system, under conditions where GATOR2 and Sestrin2 interact, we were unable to detect an interaction between recombinant TSC1 and endogenous Sestrin2 (FIG. 5E). Given the strong interaction of Sestrin2 with GATOR2, we reasoned that Sestrin2 might regulate the capacity of the mTORC1 pathway to sense amino acids. Indeed, stable over-expression of Sestrin2 dose-dependently inhibited mTORC1 activation by amino acids, as determined by the phosphorylation of S6K1, confirming its role as a negative regulator (FIGS. 2A and 6A). In addition, consistent with previous reports (Budanov and Karin, 2008), stable over-expression of FLAG-Sestrin2 caused a dramatic reduction in cell size (FIG. 2B), a well-known consequence of mTORC1 inhibition (Fingar et al., 2002).

We further explored the effect of Sestrins by creating shRNA-mediated knockdowns or CRISPR/Cas9-mediated knockouts for Sestrin1 or Sestrin2. ShRNA-mediated knockdowns were created by seeding 750,000 HEK-293T cells in a 6 well plate in DMEM supplemented with 20% inactivated fetal bovine serum (IFS). Twenty-four hours later, the cells were transfected with the shRNA-encoding plasmids indicated below alongside the Delta VPR envelope and CMV VSV-G packaging plasmids using the XtremeGene9 transfection reagent.

Lentiviral shRNAs targeting Sestrin1, Sestrin2, and Sestrin3 were obtained from the TRC (RNAi Consortium; Broad Institute). The TRC number for each shRNA is as follows:

Human Sestrin1 shRNA_1: TRCN0000143187
Human Sestrin1 shRNA_2: TRCN0000435014
Human Sestrin2 shRNA_1: TRCN0000143630
Human Sestrin2 shRNA_2: TRCN0000122802
Human Sestrin3 shRNA_1: TRCN0000412760
Human Sestrin3 shRNA_2: TRCN0000088252

Twelve hours post-transfection, the old media was aspirated and replaced with 2 ml fresh media. Virus-containing supernatants were collected 36 hours after replacing media and passed through a 0.45 micron filter to eliminate cells. Four million cells in the presence of 8 μg/ml polybrene (Millipore) were infected with 1 ml of virus for each construct in the case of single knockdown or with 500 ul of virus in the case of double or triple knockdown in 2 ml total volume of media and then spun at 2,200 rpm for 45 minutes at 37° C. Forty-eight hours after selection, cells were trypsinized and selected with puromycin and seeded on the $3^{rd}$ day for signaling experiments, as described.

To validate knockdown of Sestrin1 and Sestrin3, the following primer pairs were used in an RT-PCR reaction due to the lack of antibodies to these proteins. The data were analyzed via the delta-delta Ct method (Schmittgen and Livak, 2008).

|  |  |
|---|---|
| Sestrin1 Forward: | (SEQ ID NO: 22)<br>TGGCAATGCACAAAGATGTTG |
| Sestrin1 Reverse: | (SEQ ID NO: 23)<br>GCTACGATCCAATAGCTGGTT |
| Sestrin3 Forward: | (SEQ ID NO: 24)<br>TGCGTTTGTGATCTTGCTAATG |
| Sestrin3 Reverse: | (SEQ ID NO: 25)<br>CGCCTCTTCATCTTCCCTTTC |

CRISPR/Cas9-mediated knockouts were created as described for the GATOR2 knockouts in Example 3, using the following sense and anti-sense guide RNAs:

|  |  |
|---|---|
| sgSestrin2_1S: | (SEQ ID NO: 26)<br>caccgAGAGCCTCGAGCAGCACCTG |
| sgSestrin2_1AS: | (SEQ ID NO: 27)<br>aaacCAGGTGCTGCTCGAGGCTCTc |
| sgSestrin2_2S: | (SEQ ID NO: 28)<br>caccGGACTACCTGCGGTTCGCCC |
| sgSestrin2_2AS: | (SEQ ID NO: 29)<br>aaacGGGCGAACCGCAGGTAGTCC |
| sgSestrin2_3S: | (SEQ ID NO: 30)<br>caccGCCACAGCCAAACACGAAGG |
| sgSestrin2_3AS: | (SEQ ID NO: 31)<br>aaacCCTTCGTGTTTGGCTGTGGC |

In HEK-293T cells, inhibition of just Sestrin1 or Sestrin2, caused by either short-hairpin RNA (shRNA)-mediated knockdown or CRISPR/Cas9-mediated knockout, caused only a slight defect in mTORC1 inhibition upon amino acid withdrawal (FIG. 2C, and FIGS. 6 B-E). The double knockdown of Sestrin1 and Sestrin3 had a similarly weak effect (FIG. 2C) while that of Sestrin1 and Sestrin2 more robustly rescued mTORC1 signaling in the absence of amino acids (FIG. 2E). Finally, when we inhibited all three Sestrins by expressing shRNAs targeting Sestrin1 and Sestrin3 in Sestrin2-null cells created with the CRISPR/Cas9 system, we obtained a strong but still partial rescue of mTORC1 signaling upon amino acid deprivation (FIG. 2C). In addition, triple knockdown of all three Sestrins using shRNAs in HEK-293E cells rendered the cells insensitive to glucose deprivation (FIG. 6F). These data indicate that the Sestrins play redundant roles within the mTORC1 pathway and collectively are necessary for the full inhibition of mTORC1 signaling that occurs in the absence of amino acids or glucose.

Example 5

The Sestrins Relationship to GATOR1 and the Rae GTPases

To further understand how the Sestrins play a regulatory role in the amino acid sensing pathway, we investigated whether they require other components of the pathway to inhibit mTORC1 signaling. The nucleotide loading state of the Rag GTPase heterodimer is critical for the proper sensing of amino acids by mTORC1 (Sancak et al., 2008).

Amino acids promote GTP loading of RagA/B GTPase and GDP loading of RagC/D GTPase, enabling them to recruit mTORC1 to the lysosomal surface (Sancak et al., 2008). The GAP activity of GATOR1 leads to GTP hydrolysis of RagA/B GTPase and inhibition of the pathway (Bar-Peled et al., 2013).

Figures 3A, 3B:
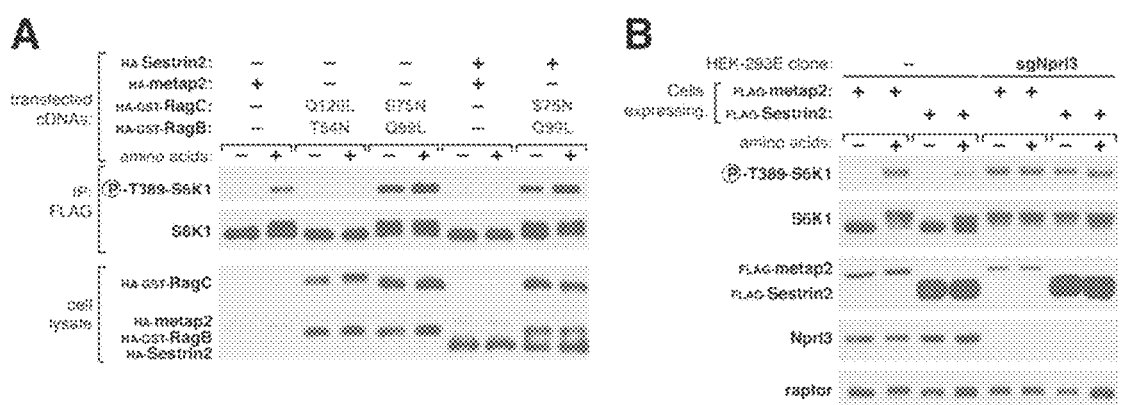
FIGS. 3A and 3B.

Several lines of evidence support the notion that the Sestrins depend on the Rag GTPases and GATOR1 to function as negative regulators of mTORC1. First, concomitant overexpression of recombinant Sestrin2 and the dominant active RagBQ99L-RagCS75N GTPase pair prevented Sestrin2-mediated inhibition of the pathway, thus placing the Sestrins upstream of the Rag GTPases (FIG. 3A). Second, while Sestrin2 overexpression strongly abrogated signaling in cells expressing GATOR1, in Nprl3-null HEK-293E cells produced via the CRISPR/Cas9-system (see guide RNAs in Example 3), Sestrin2 failed to inhibit the constitutive mTORC1 signaling observed in the absence of GATOR1. Thus, GATOR1 is epistatic to Sestrin2 (FIG. 3B).

Given that Sestrin2 functions upstream of GATOR1, we tested the possibility that it might inhibit the pathway by enhancing the GAP activity of GATOR1. GAP assays were performed essentially as previously described (Bar-Peled et al., 2013). In brief, the indicated GTPases were bound to FLAG-M2 affinity gel and loaded with XDP and [$\alpha$-$^{32}$P] GTP at room temperature followed by an incubation with $MgCl_2$ to stabilize the nucleotide. The GTPases were subsequently washed to remove unbound nucleotide and eluted from the affinity gel with competing FLAG peptide. Protein concentrations were determined prior to use. The results of this assay showed that GATOR1 GAP activity is unaltered when isolated from cells overexpressing Sestrin2.

Previous work has shown that lysosome-associated machinery, which includes the v-ATPase, is necessary for the amino acid induced activation of mTORC1 (Zoncu et al., 2011). Interestingly, inhibition of the v-ATPase with concanamycin A (ConA), which decreased mTORC1 signaling, also reduced the interaction between Sestrin2 and GATOR2 in the absence of amino acids.

Taken together, these results demonstrate that Sestrin2 requires GATOR1 and the Rag GTPase regulation in order to inhibit mTORC1 signaling and are consistent with it having a modulatory role in the amino acid sensing pathway upstream of mTORC1.

Example 6

The Effect of Sestrins on Amino Acid-Regulated Subcellular Localization of mTORC1

Given that Sestrin2 is upstream of GATOR1 and the Rag GTPases, we reasoned that the Sestrins might inhibit the pathway by controlling the subcellular localization of mTORC1, analogous to previously characterized regulators of the amino acid sensing pathway (Bar-Peled et al., 2013; Petit et al., 2013; Sancak et al., 2010b; Sancak et al., 2008; Tsun et al., 2013; Zoncu et al., 2011). We employed immunofluorescence assays to determine mTORC1 subcellular localization as previously described (Sancak et al., 2010a). Briefly, 300,000 HEK-293T cells were plated on fibronectin-coated glass coverslips in 6-well tissue culture plates. Twenty-four hours later, the slides were rinsed with PBS once and fixed for 15 min with 4% paraformaldehyde in PBS at room temperature. The slides were rinsed three times with PBS and cells were permeabilized with 0.05% Triton X-100 in PBS for 5 min. After rinsing three times with PBS, the slides were blocked for 1 hour in Odyssey blocking buffer (LI-COR Biosciences), and then incubated with primary antibody in Odyssey blocking buffer for 1 hr at room temperature. These slides were then rinsed three times with PBS, incubated with secondary antibodies produced in donkey (diluted 1:1000 in Odyssey blocking buffer) for 45 minutes at room temperature in the dark, and washed three times with PBS. Slides were mounted on glass coverslips using Vectashield (Vector Laboratories) and imaged on a spinning disk confocal system (Perkin Elmer).

Figure 4A:
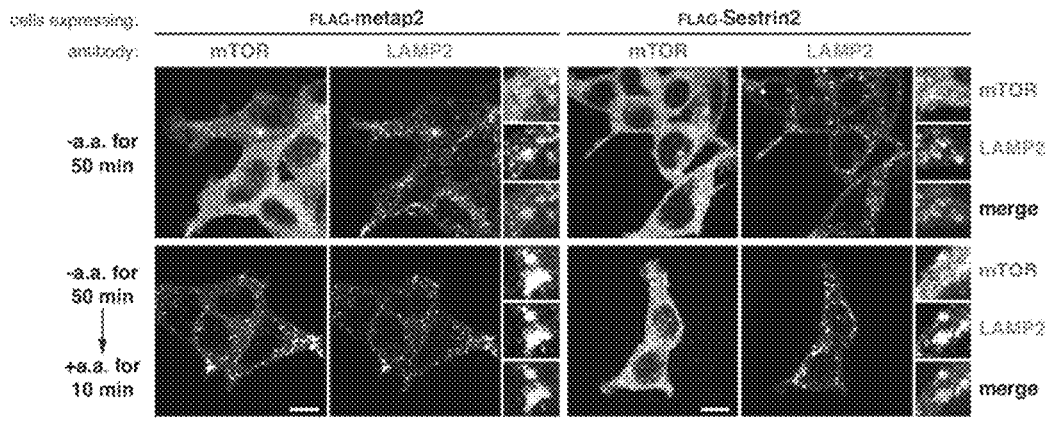
FIGS. 4A, 4B and 4C.
Figure 4B:
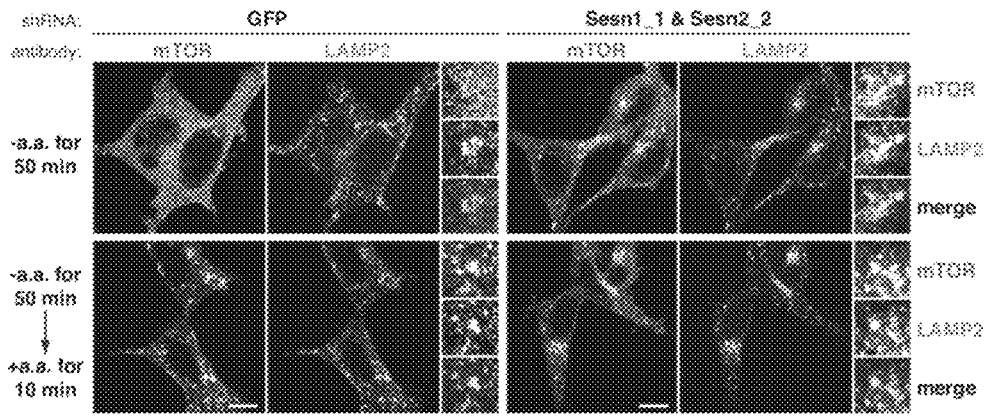
Figure 4C:
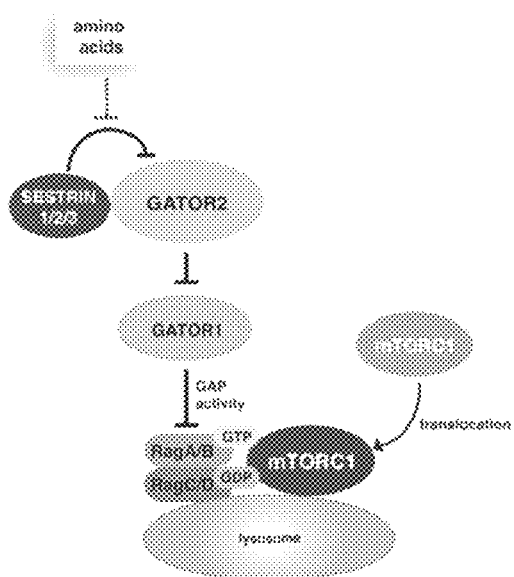
Figures 7A, 7B:
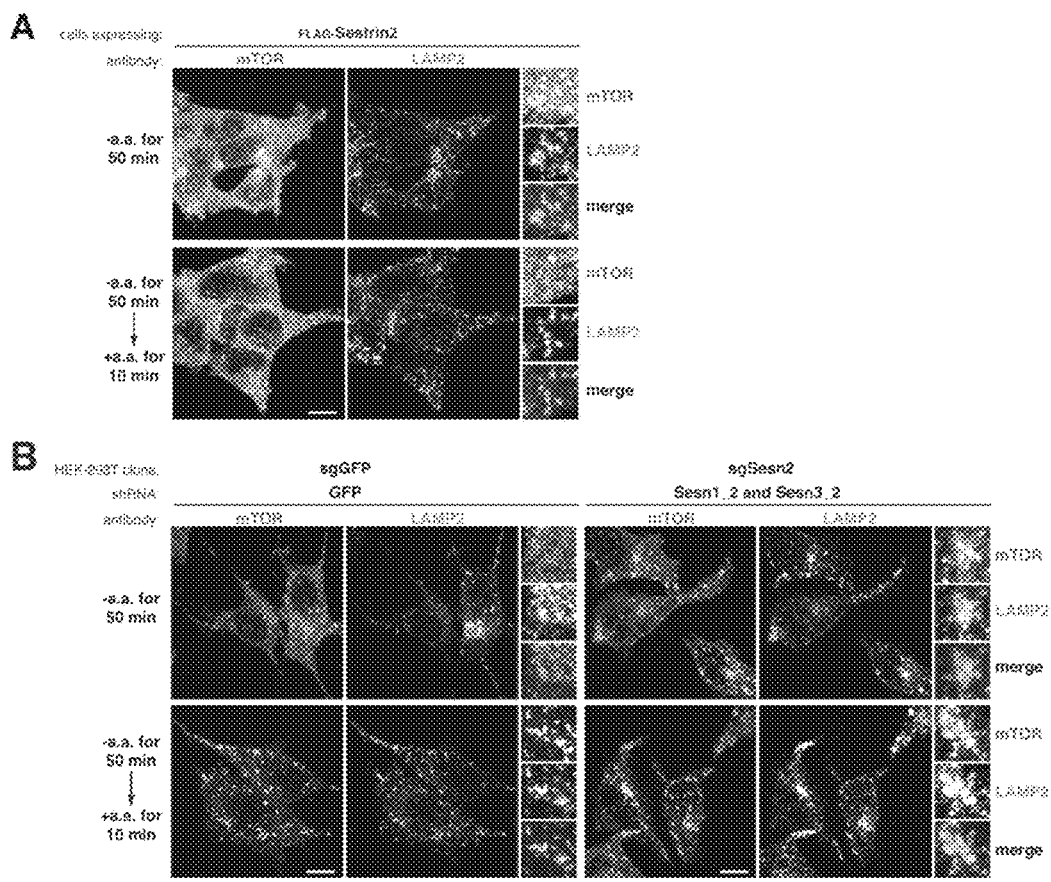
FIGS. 7A and 7B.

In HEK-293T cells stably overexpressing FLAG-Sestrin2, mTORC1 failed to translocate to LAMP2-positive lysosomes despite the presence of amino acids (FIG. 4A and FIG. 7A). Conversely, shRNA-mediated knockdown of Sestrin1 and Sestrin2 led to increased levels of lysosome-associated mTORC1 even in the absence of amino acids (FIG. 4B). Similarly, the shRNA-mediated knockdown of Sestrin1 and Sestrin3 in Sestrin2-null cells also increased the localization of mTORC1 to lysosomes under amino acid deprivation conditions (FIG. 7B). In combination, these results indicate that the Sestrins are negative regulators of mTORC1 signaling that are necessary for the amino acid-dependent localization of mTORC1 to the lysosomal surface (FIG. 4C).

Example 7

The Effect of Specific Amino Acids on the Sestrin-GATOR2 Interaction

Figures 8A, 8B, 8C:
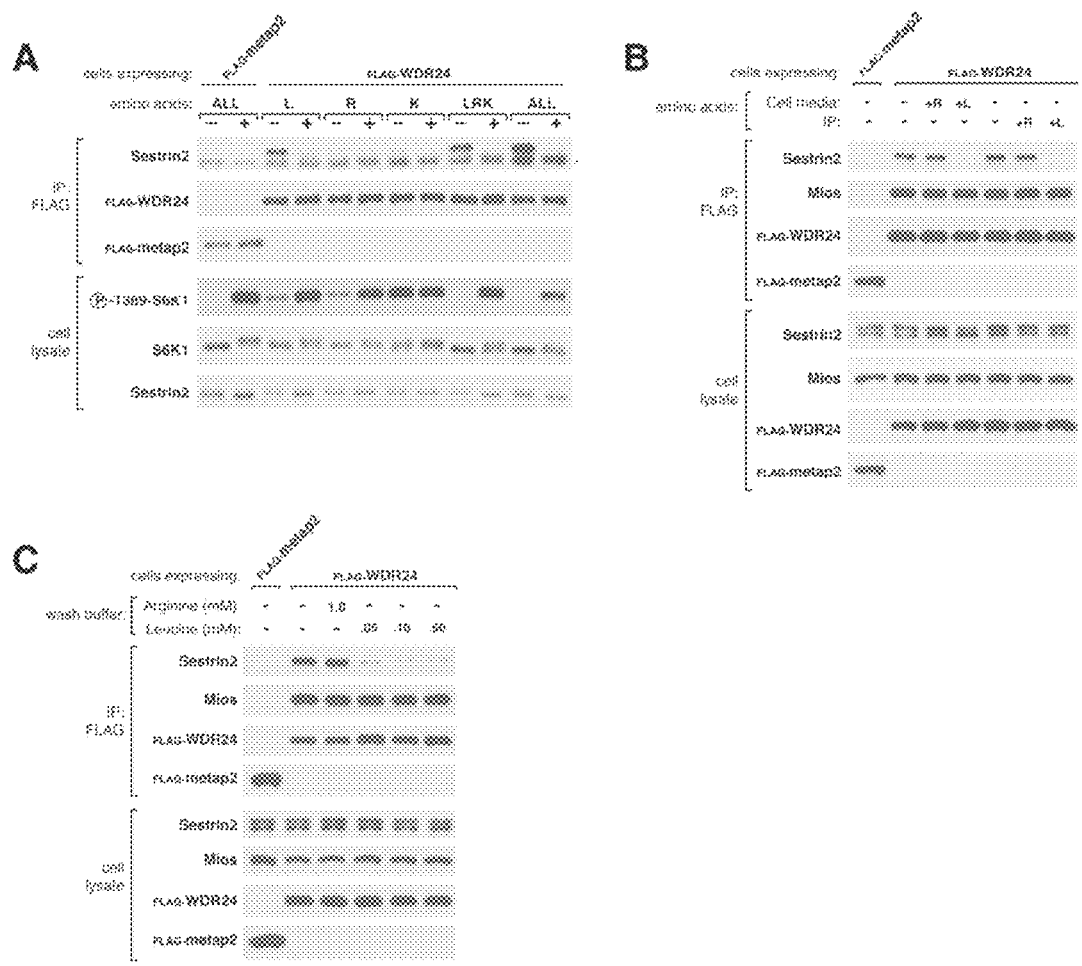
FIGS. 8A, 8B and 8C.

In order to further explore if specific amino acid levels affected the Sestrin-GATOR2 interaction, HEK-293T cells stably expressing the FLAG-tagged GATOR2 component WDR24 (and FLAG-tagged metap2 as a control) were starved of either all amino acids (ALL); only leucine, arginine, and lysine (LRK); only leucine (L); only arginine (R); or only lysine (K) for 50 minutes, or starved for 50 minutes and restimulated for 10 minutes with the indicated amino acids. Immunoprecipitates were analyzed along with cell lysates by immunoblotting for the indicated proteins as shown in FIG. 8A.

HEK-293T cells stably expressing the FLAG-tagged GATOR2 component WDR24 were starved of all amino acids for 50 minutes. Individual amino acids were added pre-lysis to the cell culture media or post-lysis to cell lysates prior to FLAG immunoprecipitation. Immunoprecipitates were analyzed along with cell lysates by immunoblotting for the indicated proteins as shown in FIG. 8B.

Finally, HEK-293T cells stably expressing the FLAG-tagged GATOR2 component WDR24 were starved of all amino acids for 50 minutes. Immunoprecipitates were subjected to washes containing the indicated amounts of leucine or arginine and analyzed along with cell lysates by immunoblotting for the indicated proteins as shown in FIG. 8C.

The results of these studies demonstrate that leucine, but not arginine or lysine, disrupts the Sestrin-GATOR2 interaction.

Example 8

Leucine Directly Regulates the Sestrin2-GATOR2 Interaction

Figures 9A, 9B, 9C:
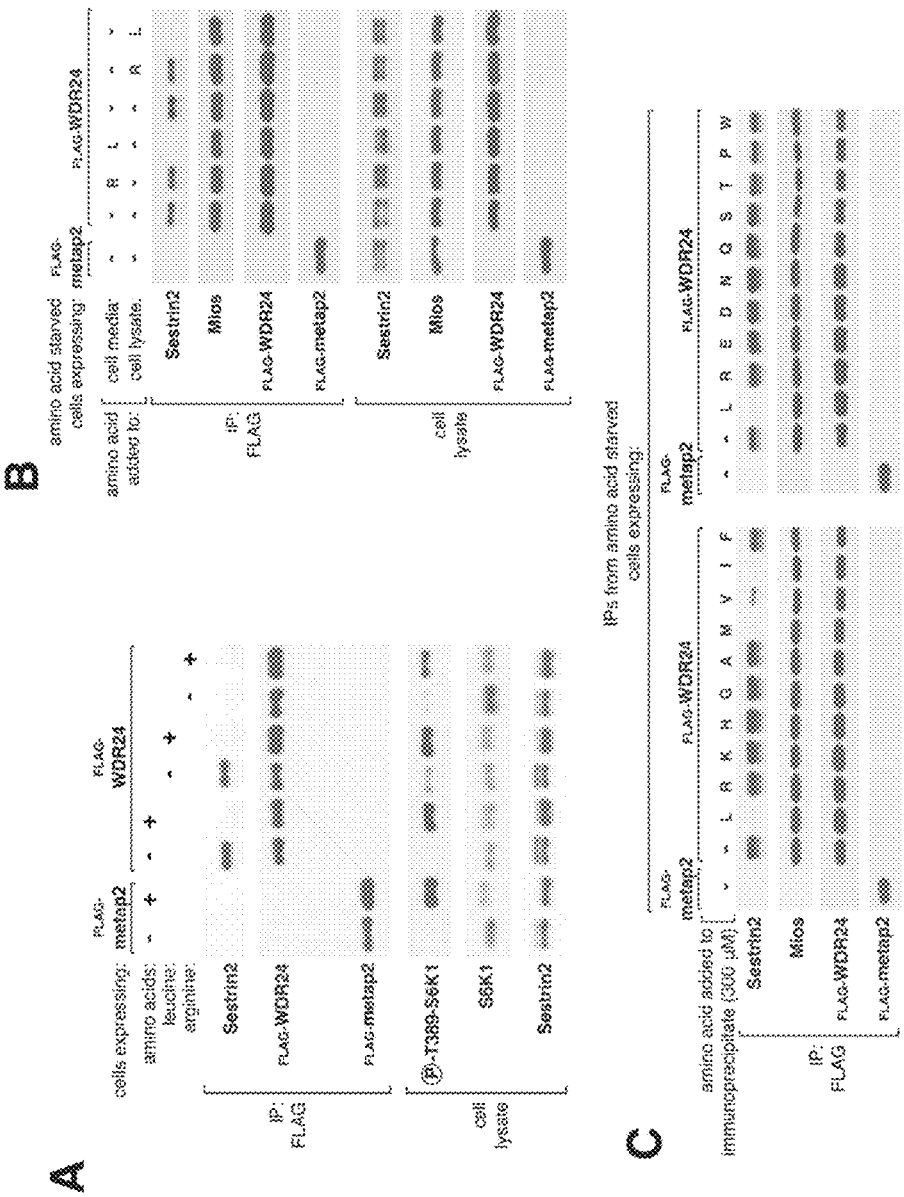

HEK-293T cells stably expressing FLAG-WDR24 or the control protein FLAG-metap2 (as described in Example 1) were starved for leucine, arginine, or all amino acids for 50 minutes. In some samples, cells were re-stimulated with leucine, arginine, or all amino acids for 10 minutes and then FLAG immunoprecipitates prepared from cell lysates. Immunoprecipitates and lysates were analyzed by immunoblotting for indicated proteins. Removal of either leucine or arginine from the cell media inhibited mTORC1 signaling, as indicated by S6K1 phosphorylation, to similar extents. Strikingly, however, only leucine starvation caused Sestrin2 to bind to GATOR2 inducing the interaction as effectively as complete amino acid starvation (FIG. 9A). Leucine re-addition rapidly reversed the binding and amino acids did not affect the interaction between WDR24 and Mios, two core components of GATOR2 (FIG. 9A). Leucine starvation and stimulation also strongly regulated the interaction of endogenous Sestrin1, but not endogenous Sestrin3, with GATOR2 (Figure not shown).

Figures 9D, 9E:
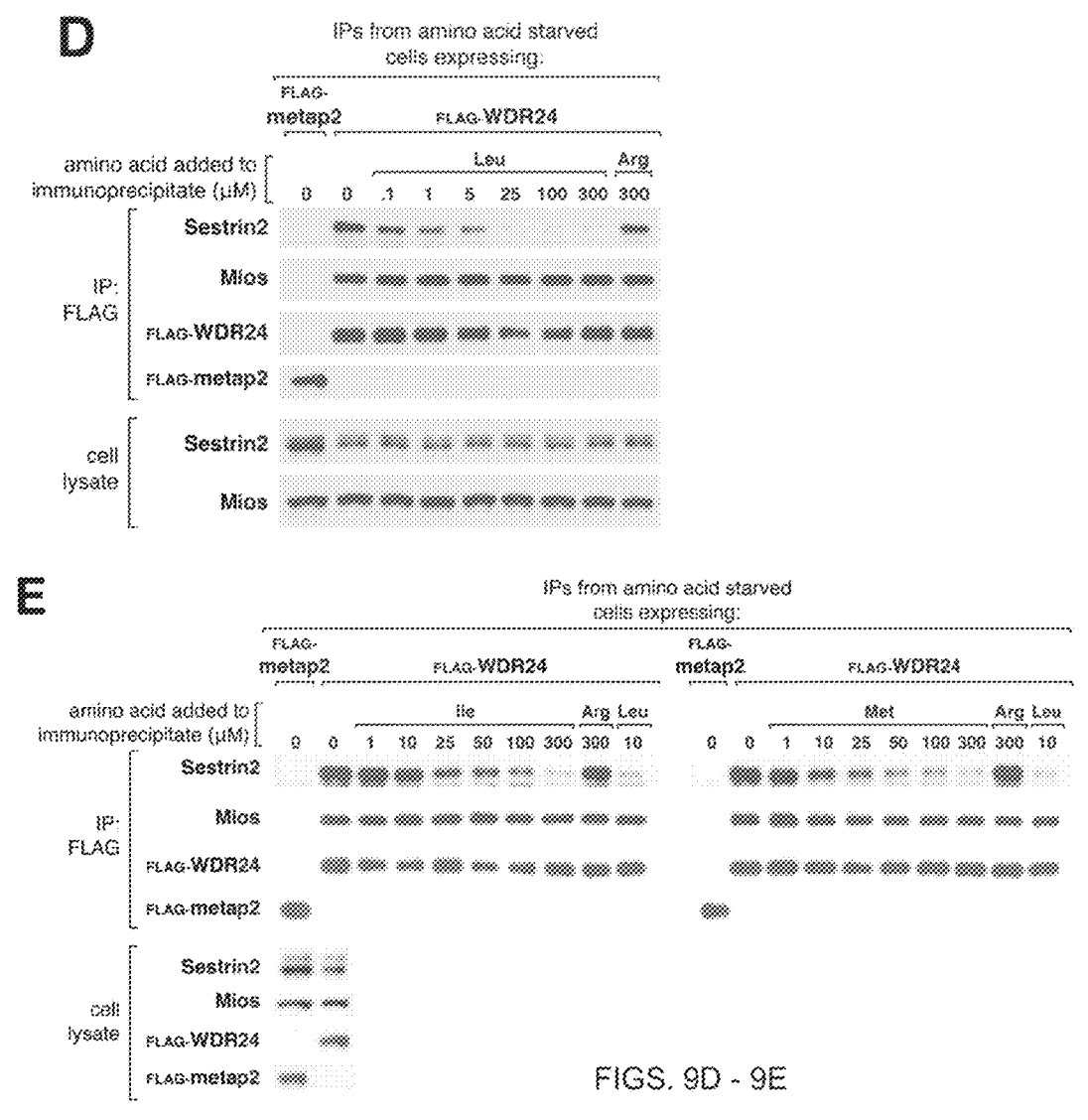

We next tested if leucine acts directly on the Sestrin2-GATOR2 complex. The addition of leucine, but not arginine, to ice-cold detergent lysates of HEK-293T cells starved for all amino acids abrogated the interaction to the same extent as leucine-stimulation of live cells (FIG. 9B). Leucine disrupted the interaction when added directly to immunopurified Sestrin2-GATOR2 complexes isolated from amino acid-starved cells. Of the 18 amino acids tested at 300 µM each, only those most similar to leucine—methionine, isoleucine, and valine—had any effect on the Sestrin2-GATOR2 interaction, in vitro (FIG. 9C). When added to the purified complexes, leucine dose-dependently disrupted the Sestrin2-GATOR2 complex with the half maximal effect at about 1 µM (FIG. 9D). Methionine and isoleucine were considerably less potent, acting at concentrations, approximately 10- and 25-fold greater than leucine, respectively (FIG. 9E). These values reflect only the relative potencies of these amino acids as equilibrium conditions were not attained because the large assay volume precluded Sestrin2 from rebinding to GATOR2 once dissociated.

Example 9

Leucine Binds to Sestrin1 and Sestrin2

Four million HEK-293T cells were plated in a 15 cm plate four days prior to the experiment. Each plate yielded the protein for one sample. Forty-eight hours after plating, the cells were transfected via the polyethylenimine method (O. Boussif et al., PNAS (USA), 92:7297-7301 (1995)) with the pRK5-based cDNA expression plasmids indicated in the figures in the following amounts: 5 µgFLAG-Sestrin2; 12 µg of the negative control Rap2A; 5 µg WDR24; 2 µg WDR24 with 4 µg each of HA-Seh1L, HA-Sec13, HA-Mios, and HA-WDR59; 12 ng FLAG-dSestrin (CG11299-PD); 12 µgFLAG-Sestrin1.1; 12 µg FLAG-Sestrin1.2; 12 µg FLAG-Sestrin3; 12 µg FLAG-Sestrin2 mutants (L261A, E451A, S190A) and up to 20 µg total DNA with empty-PRK5. Forty-eight hours after transfection cells were lysed as described in Example 1. If multiple samples of the same type were represented in the experiment, the cell lysates were combined, mixed, and evenly distributed amongst the relevant tubes, to ensure equal protein amounts across samples of the same type.

Anti-FLAG immunoprecipitates were prepared as previously described, with the exception that, prior to incubation with lysates, the beads were blocked by rotating in 1 µg/µl bovine serum albumin (BSA) for 20 minutes at 4° C. and subsequently washed twice in lysis buffer. Thirty µl of the 50/50 slurry of beads in lysis buffer was added to each of the clarified cell lysates and incubated as previously described in Example 1.

For the binding assays, two tubes at a time were washed as previously indicated for immunoprecipitations. All the liquid was subsequently aspirated and a 15 µl aliquot of proteins bound to the beads was incubated for one hour on ice in cytosolic buffer (0.1% Triton, 40 mM HEPES pH 7.4, 10 mM NaCl, 150 mM KCl, 2.5 mM MgCl2) with the appropriate amount of [$^3$H]-labeled amino acids and unlabeled amino acids. Tubes were flicked every five minutes. At the end of one hour, the beads were briefly spun down, aspirated dry, and rapidly washed three times with binding wash buffer (0.1% Triton, 40 mM HEPES pH 7.4, 150 mM NaCl). The beads were aspirated dry again and resuspended in 85 µl of binding wash buffer. With a cut tip, each sample was mixed well and three 10 µl aliquots were separately quantified using a TriCarb® scintillation counter (PerkinElmer). This process was repeated in pairs for each sample, to ensure similar incubation and wash times for all samples analyzed across different experiments.

For each sample, an immunoprecipitation was performed in parallel. After washing four times as previously described and once with CHAPS buffer (0.3% CHAPS, 40 mM HEPES pH 7.4), the protein was eluted in 250 µl of CHAPS buffer with 300 mM NaCl and 1 mg/ml FLAG peptide for 1 hour at 4° C. The eluent was subsequently concentrated, quantified for protein amount using Bradford reagent, and resuspended in sample buffer. The proteins were resolved by 4-12% SDS-PAGE, and stained with SimplyBlue™ SafeStain.

Figures 10A, 10B:
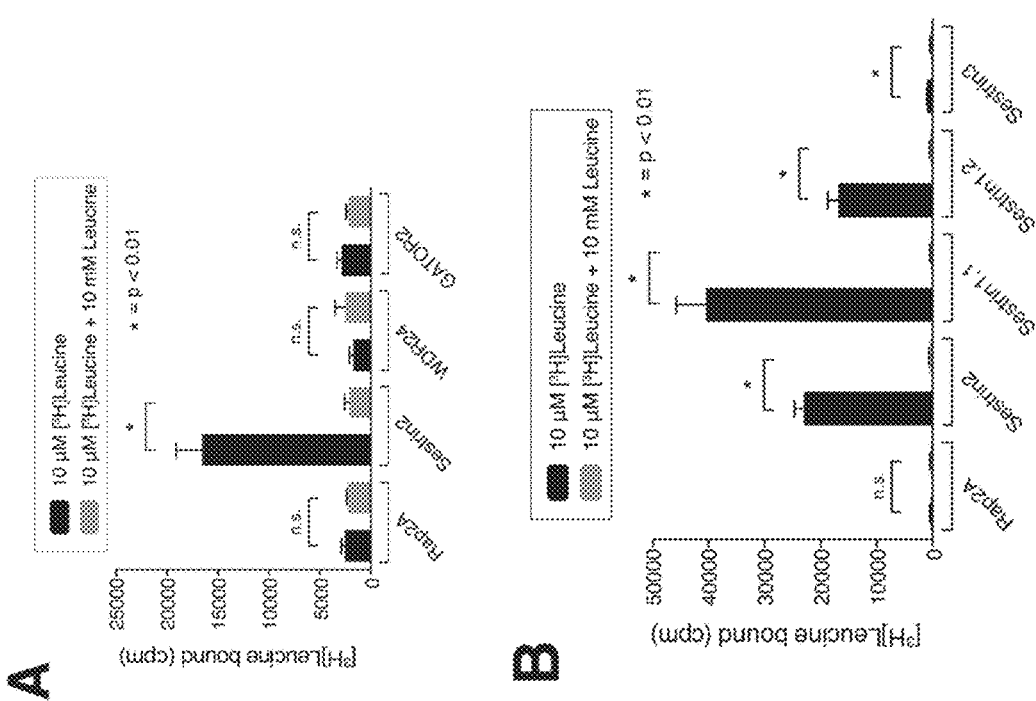
FIGS. 10A, 10B, 10C, 10D, 10E, 10F, and 10G.

We found that radiolabeled leucine bound to Sestrin2, but not WDR24, the GATOR2 complex, or the control protein Rap2A, in a manner that was fully competed by excess unlabeled leucine (FIG. 10A). In contrast, arginine did not bind to either Sestrin2 or Rap2 (figure not shown). Consistent with the differential sensitivities of the Sestrin1- and Sestrin3-GATOR2 complexes to leucine, Sestrin1 bound leucine to a similar extent as Sestrin2, while Sestrin3 bound leucine only slightly above background (FIG. 10B).

Figure 10C:
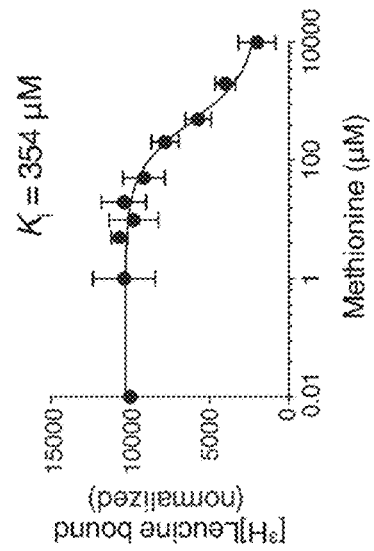
Figure 10D:
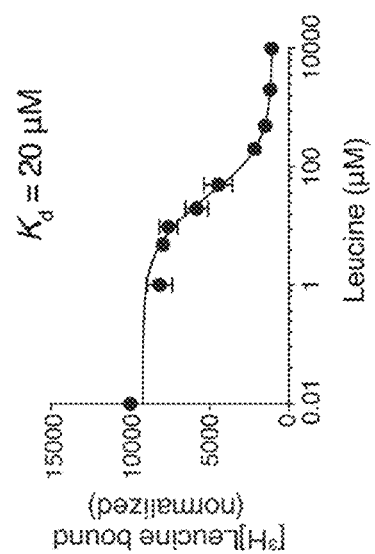
Figure 10E:
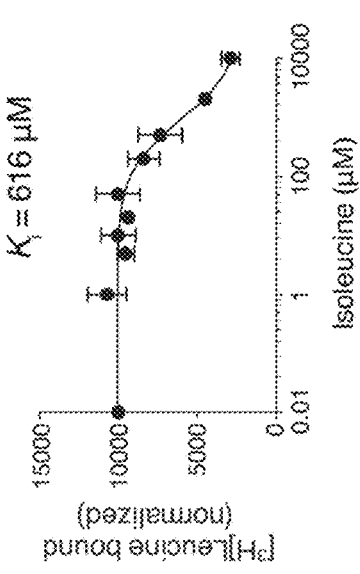

Amino acid affinities to Sestrin2 were determined by first normalizing the bound [$^3$H]-labeled amino acid concentrations across three separate binding assays performed with varying amounts of unlabeled amino acid competition. These values were plotted and fit to a hyperbolic equation (Cheng-Prusoff equation) to estimate the $IC_{50}$ value. $K_d$ or $K_i$ values were derived from the $IC_{50}$ value using the equation: $K_d$ or $K_i=IC_{50}/(1+([[^3H]Leucine])/K_d)$. In competition experiments with increasing amounts of unlabeled leucine, we determined that leucine has a $K_d$ for Sestrin2 of 20±5 µM (FIG. 10C). In comparison, methionine and isoleucine competed leucine binding with inhibitory constants ($K_i$) of 354±118 µM and 616±273 µM, respectively (FIG. 10D, 10E). These values are approximately 18 and 30 times lower than the affinity of leucine for Sestrin2, and correlate well with the relative potencies of leucine, methionine, and isoleucine in disrupting the Sestrin2-GATOR2 interaction in vitro (FIG. 9D, 9E).

As all of these proteins were expressed in and purified from human HEK-293T cells, it remained formally possible that an unidentified protein that co-purifies with Sestrin2 (and Sestrin1) is the actual receptor for leucine. To address this possibility, we prepared human Sestrin2 in bacteria, a heterologous system that does not encode a Sestrin homologue or even a TOR pathway.

Recombinant Sestrin2 was expressed in *Escherichia coli* (strain BL21 DE3 star) from the His-MBP-TEV-Sestrin2 in pMAL6H-CSXT plasmid. The bacterial cultures were grown at 30° C. to an optical density of 0.4 at which point the temperature was lowered to 18° C. After 30 minutes at 18° C., the cultures were induced overnight at 18° C. with 0.5 mM IPTG. The cells were subsequently resuspended in lysis buffer with TCEP (50 mM Tris pH 7.4, 200 mM NaCl, 5 mM MgCl$_2$, 0.1% CHAPS, 1 mM TCEP, 200 µM leucine, and protease inhibitor tablets), which was then supplemented with lysozyme and crude DNAse. The cells underwent mechanical homogenization and the lysates were cleared by centrifugation and then loaded onto the Ni-NTA resin. After incubation, the resin was washed once with lysis buffer with TCEP, once with lysis buffer with TCEP+300 mM NaCl, and once with lysis buffer with TCEP+25 mM imidazole. The proteins were eluted with lysis buffer with TCEP+300 mM imidazole. The eluted proteins were concentrated and purified using size exclusion chromatography on a HiLoad® 16/60 Superdex® 200 column (GE Healthcare), which was equilibrated with the following buffer: 50 mM Tris pH 7.4, 150 mM NaCl, 5 mM $MgCl_2$, 1 mM DTT, and 200 µM leucine. The collected protein was concentrated and immediately used in binding assays or frozen at −80° C. Before use in any binding assays, the protein was diluted sufficiently to significantly decrease the leucine that may have remained bound through the purification steps. The control His-RagA/RagC heterodimer was purified through a similar protocol, using the Ni-NTA resin and subsequent size exclusion chromatography.

For binding assays performed with bacterially-produced proteins, 23.6 µg His-RagA/RagC, 23.6 µg His-MBP-TEV-Sestrin2, or 73.6 µg His-MBP-TEV-Sestrin2 were diluted into 500 µl lysis buffer (50 mM Tris pH 7.4, 200 mM NaCl, 5 mM $MgCl_2$, 0.1% CHAPS) and incubated with 15 µl compact Ni-NTA resin as previously described. For the binding assays, two tubes were washed at a time. The Ni-NTA resin with proteins bound to it was washed one time with lysis buffer and three times with lysis buffer supplemented with 300 mM NaCl. After washing, the liquid was aspirated and the protein bound to the resin was incubated for one hour on ice with the appropriate amount of [$^3$H]-labelled amino acids and, where indicated, cold amino acids. The tubes were flicked every five minutes. The samples were subsequently washed three times after binding with wash buffer (lysis buffer with 300 mM additional NaCl). The resin was aspirated dry and resuspended in 85 µl of wash buffer. The samples were then well mixed with a cut tip and 10 µl of each was loaded into scintillation fluid in triplicate and quantified with a TriCarb® Scintillation Counter. Samples performed in parallel were eluted with lysis buffer+300 mM imidazole and analyzed by SDS-PAGE as described above.

Figures 10F, 10G:
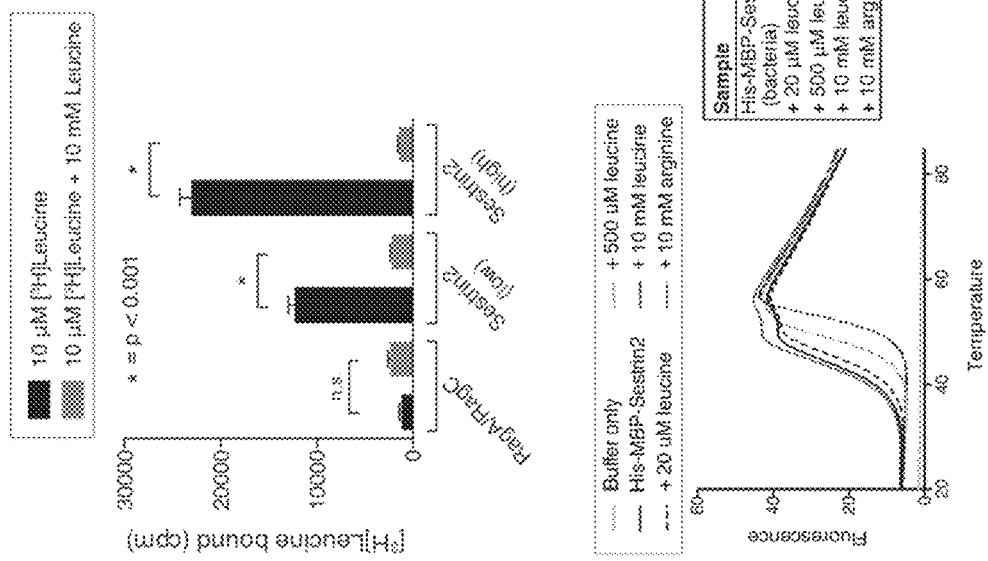

Consistent with the results obtained with Sestrin2 prepared in human cells, radiolabelled leucine bound to bacterially-produced Sestrin2, but not the RagA-RagC heterodimer, which was used as a control (FIG. 10F). Specific binding of leucine to the bacterially produced Sestrin2 was further confirmed by thermal shift assays. The thermal shift (protein melting) assays were performed according to the LightCycler® 480 instruction manual. Briefly, for Sestrin2, 5× Sypro® orange dye and Sestrin2 at 4 µM were combined with or without leucine or arginine (at the indicated concentrations) in thermal shift buffer (100 mM Tris pH 7.4, 100 mM NaCl, and 1 mM DTT) in a volume of up to 10 µl in one well of a LightCycler® Multiwell 384-well plate. 20× Sypro® orange dye was used for the two control proteins, human choline acetyltransferase (ChAT) (at 4 µM) or *Physconitrella patens* hydroxycinnamoyl transferase (PpHCT) (at 2.5 µM). Each condition was tested in triplicate. The plate was subjected to a protocol in which the temperature increased from 20° to 85° C. at 0.06° C./second. Fluorescence was recorded and plotted over time, and melting temperatures were calculated as described in the LightCycler® 480 instruction manual. Briefly, the negative first derivative of the curve shown (change in fluorescence/change in temperature) was plotted against the temperature. The peak (i.e., lowest point on this curve) reflects the melting temperature. Each reported melting temperature is the mean±SD for three replicates from one experiment.

The thermal shift assays demonstrated that leucine, but not arginine, shifted the melting temperature by up to 8.5° C. of bacterially-produced Sestrin2 (FIG. 10G). Collectively, these data demonstrate that leucine binds directly to Sestrin2.

Example 10

Sestrin Regulates mTORC1 Through GATOR2

HEK-293T cells stably expressing FLAG-WDR24 were starved for all amino acids for 50 minutes, lysed and subjected to anti-FLAG immunoprecipitation as described previously. The GATOR2-Sestrin2 complexes immobilized on the agarose beads were washed twice in lysis buffer with 500 mM NaCl, as previously described, and then incubated for 10 minutes in 1 mL of cytosolic buffer with the indicated concentrations of individual amino acids. The amount of GATOR2 and Sestrin2 that remained bound was assayed by SDS-PAGE and immunoblotting as described previously.

Figures 11A, 11B, 11C:
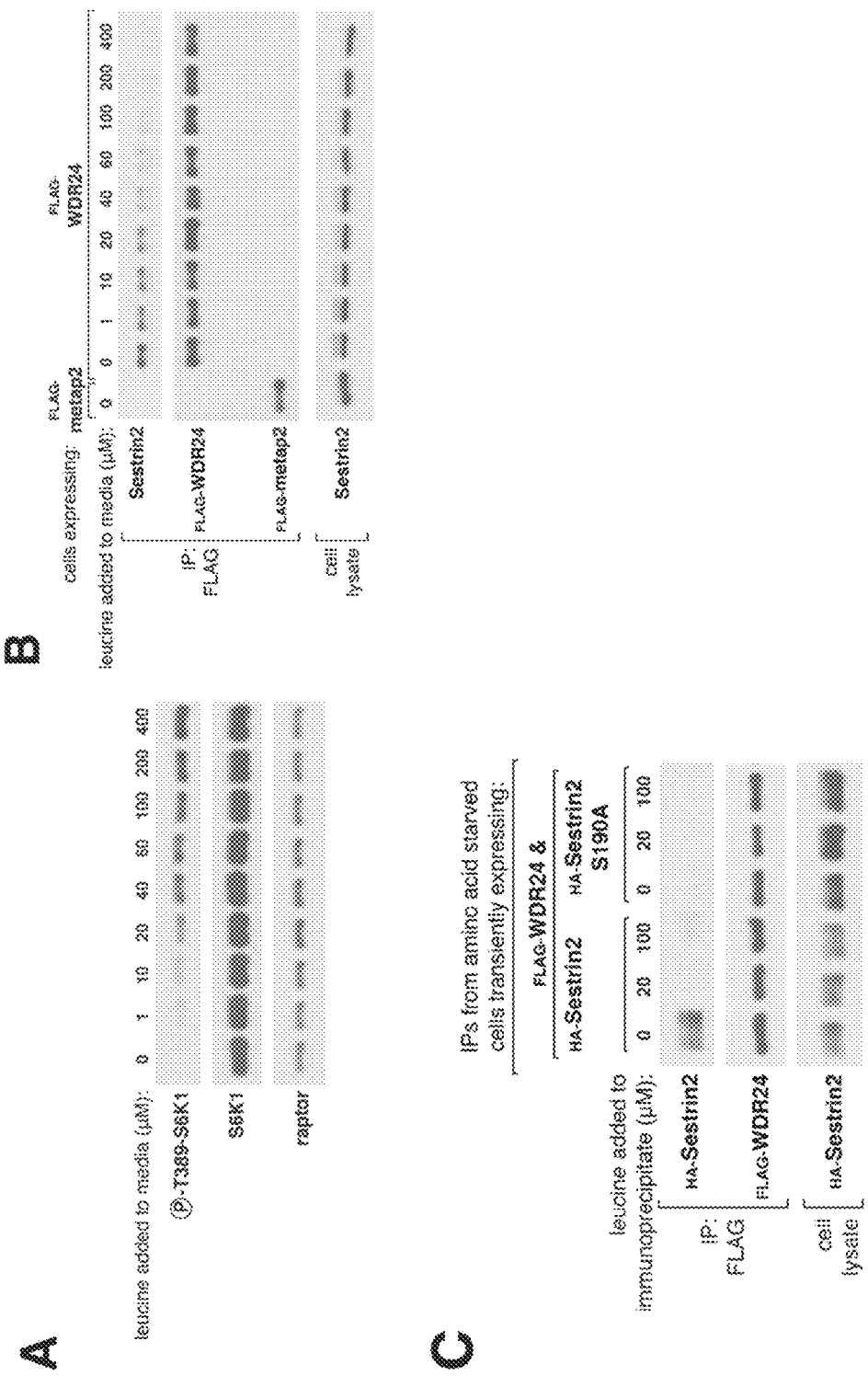
FIGS. 11A, 11B, 11C, 11D, 11E, 11F, 11G and 11H, FIG. 11A depicts an immunoblot of HEK-293T cells starved of leucine for 50 minutes and restimulated with leucine at the indicated concentrations for 10 minutes. Cell lysates were analyzed for the indicated proteins and phosphorylation states.

Consistent with leucine regulating mTORC1 by modulating the binding of Sestrin2 to GATOR2, we found that 20-40 µM leucine had half-maximal effects on both the Sestrin2-GATOR2 interaction and mTORC1 activity in HEK-293T cells (FIGS. 11A and 11B). This concentration range encompasses the Kd of leucine for Sestrin2, suggesting that the affinity of Sestrin2 for leucine is physiologically relevant.

Figures 11D, 11E:
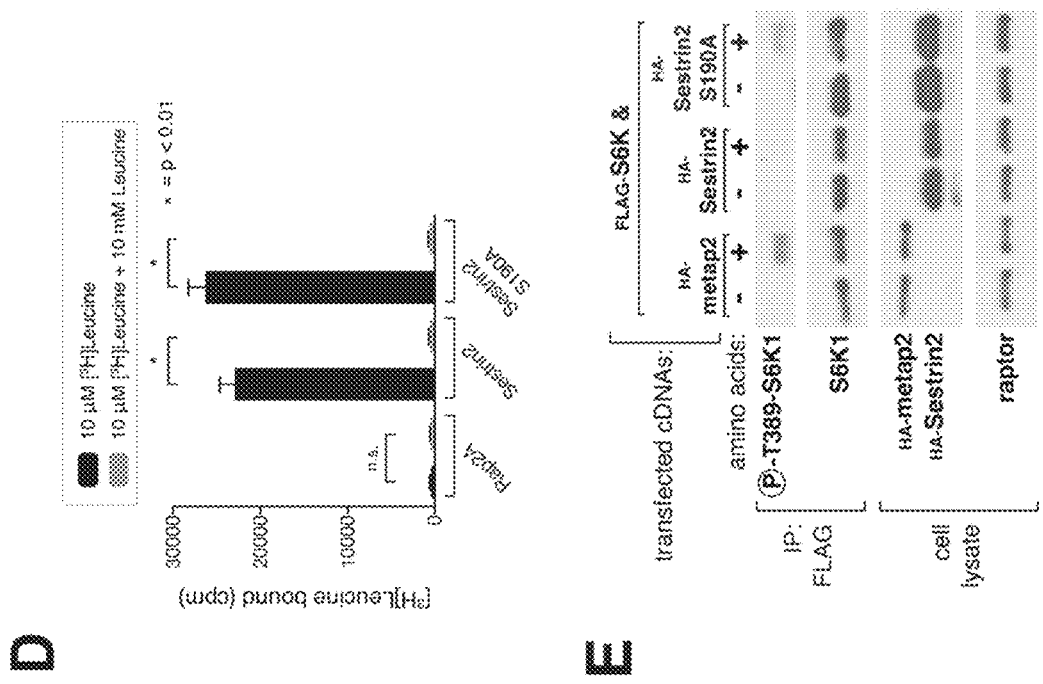

To formally test that Sestrin2 regulates mTORC1 by interacting with GATOR2, we used alanine-scanning mutagenesis to isolate a Sestrin2 mutant (S190A) that still binds leucine. FLAG immunoprecipitates were prepared from cells transiently expressing the Sestrin2 mutant (S190A) or wild-type Sestrin2 as described in Example 1. The immunopurified complexes were treated with various concentrations of leucine and then analyzed by immunoblotting. The Sestrin2 S190A mutant still binds leucine (FIG. 11D), but has severely decreased GATOR2-binding capacity (FIG. 11C).

We next starved HEK-293T cells transiently expressing Sestrin2 S190A or wild-type Sestrin2 for all amino acids for 50 minutes. Some cultures were then stimulated with all amino acids for 10 minutes before preparing anti-FLAG immunoprecipitates and cell lysates, which were analyzed by immunoblotting. When overexpressed in HEK-293T cells, the S190A mutant was less effective than wild-type Sestrin2 at inhibiting mTORC1 signaling (FIG. 11E), indicating that Sestrin2 must be able to interact with GATOR2 to impinge on mTORC1 activity.

Figures 11F, 11G, 11H:
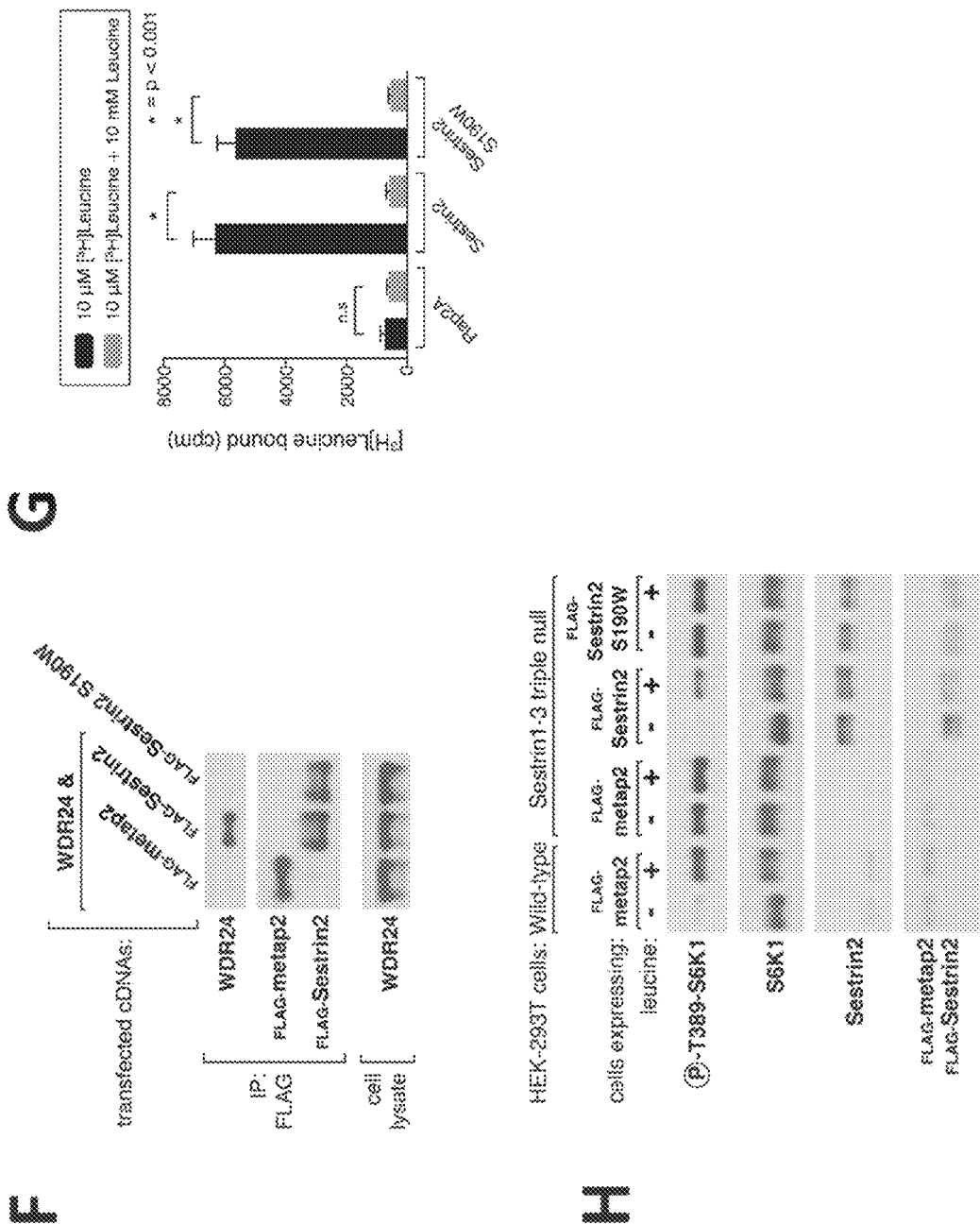

To formally test whether Sestrin2 regulates mTORC1 by interacting with GATOR2, we identified another Sestrin2 mutant (S190W) that still binds leucine but has a severely decreased capacity to bind GATOR2 (FIGS. 11F and 11G). In Sestrin1-3 triple null HEK-293T cells, mTORC1 signaling was active and unaffected by leucine deprivation (FIG. 11H). In these cells expression of wild-type Sestrin2 restored the leucine sensitivity of the mTORC1 pathway, but that of Sestrin2 S190W had no effect (FIG. 11H). Thus, Sestrin2 must be able to interact with GATOR2 for the mTORC1 pathway to sense the absence of leucine.

Example 11

Leucine Activation of mTORC1 and Proper Localization of mTORC1 to Lysosomes Requires Sestrin2 Binding to Leucine For Sestrin2 to be a leucine sensor, its capacity to bind leucine must be necessary for mTORC1 to sense the presence of leucine. To test this, we identified two Sestrin2 mutants by alanine scanning, L261A and E451A, which do not bind leucine to an appreciable degree (FIG. 12A) as determined by the binding and immunoprecipitation protocols described in Example 9.

Figures 12A, 12B, 12C:
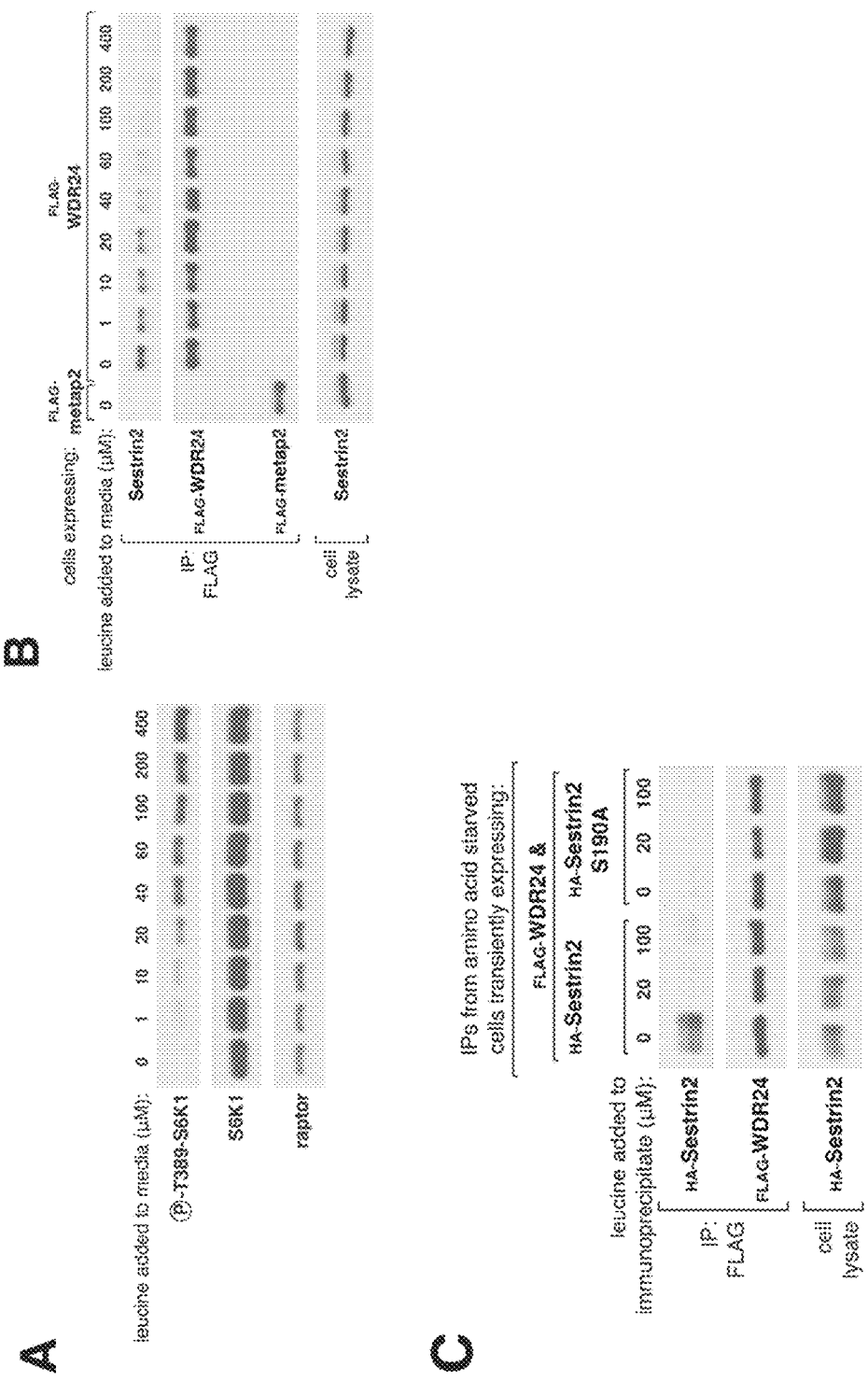
FIGS. 12A, 12B, 12C, 12D, 12E, 12F and 12G.
Figure 12D:
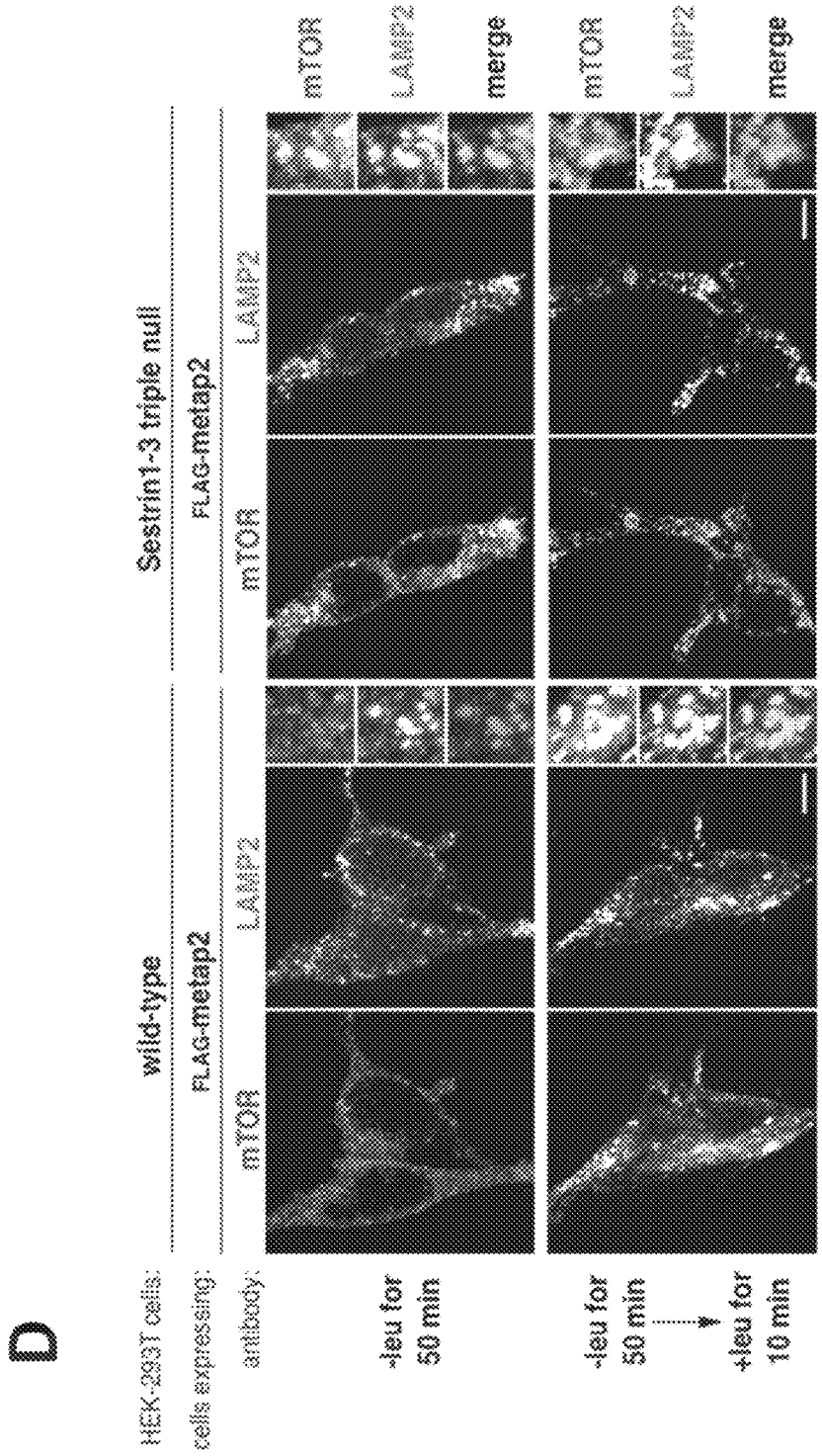
Figure 12E:
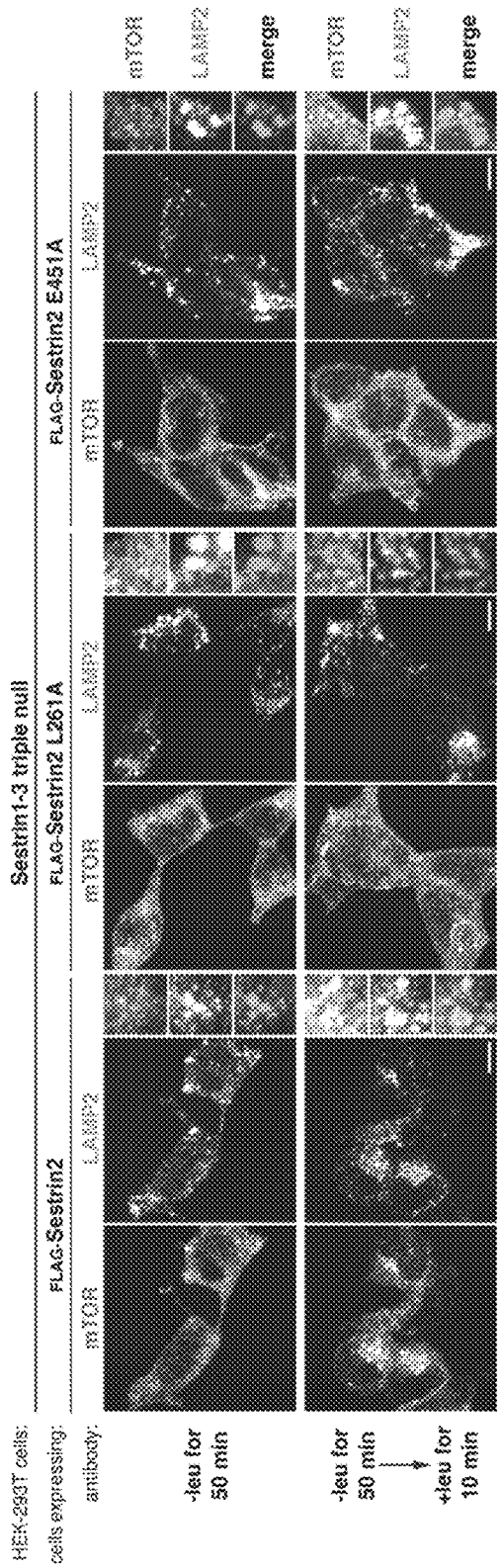
Figure 12F:
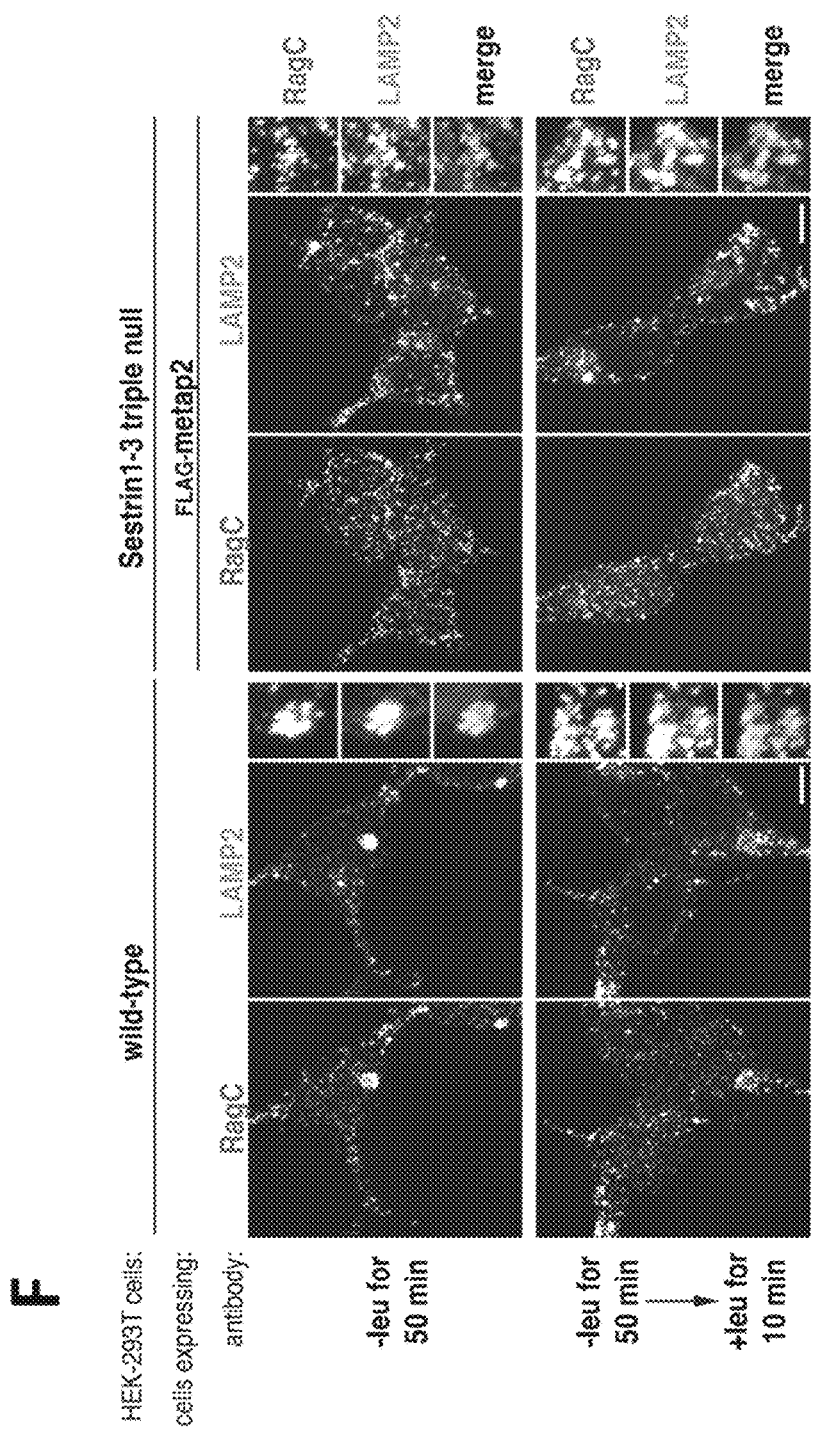
Figure 12G:
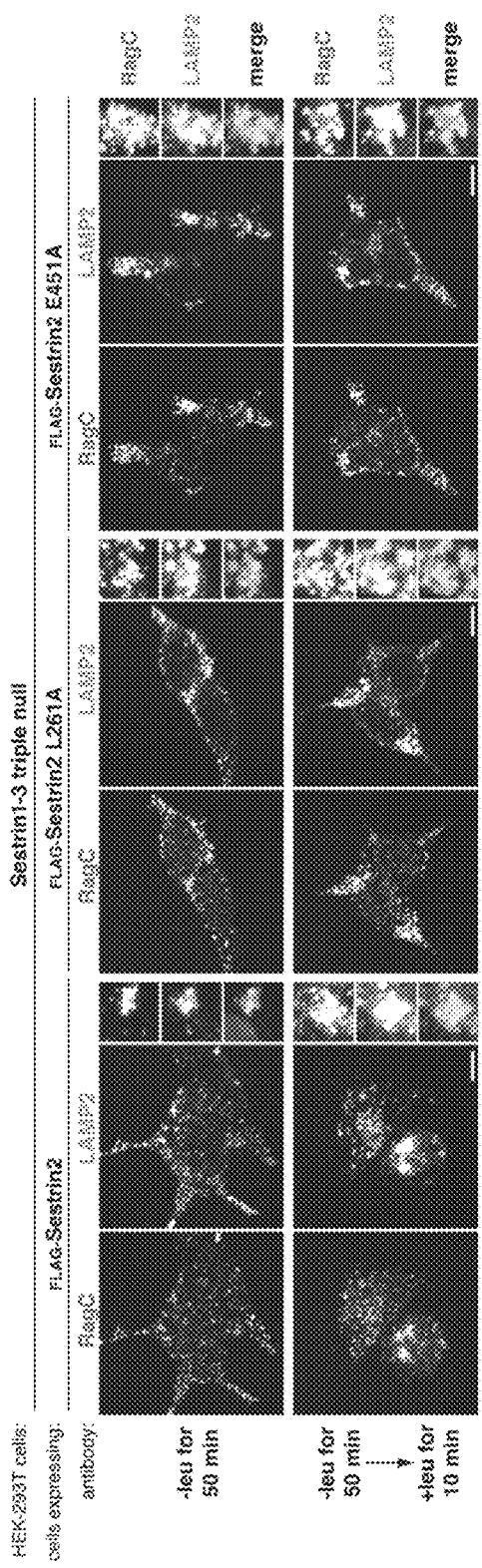

We then prepared FLAG immunoprecipitates from cells transiently expressing either one of the mutant Sestrin2 or wild-type Sestrin2, all of which were FLAG-tagged. The immunoprecipitates were treated with various concentrations of leucine and analyzed as described in Example 8. Leucine did not affect the interaction of the mutants with GATOR2 in vitro, consistent with Sestrin2 mediating the effects of leucine on the Sestrin2-GATOR2 complex (FIG. 12B).

To test the effects of these mutants on mTORC1 signaling, we created Sestrin1-3 triple null HEK-293T cells using the CRISPR/Cas9 system. The triple null cells were then used to express FLAG-tagged Sestrin2 mutants or FLAG-tagged wild-type Sestrin2. Cells were starved for leucine for 50 minutes and, either stimulated with leucine for 10 minutes or not stimulated. Lysates from the cells were analyzed via immunoblotting. In the triple null cells mTORC1 is constitutively active and unaffected by leucine deprivation (FIG. 12C). Expression in these cells of wild-type Sestrin2 restored the leucine sensitivity of the mTORC1 pathway, but that of either Sestrin2 mutant inhibited mTORC1 signaling and rendered it insensitive to leucine (FIG. 12C). Thus, activation of mTORC1 by leucine requires the binding of leucine to Sestrin2. Note that wild-type recombinant Sestrin2 is overexpressed relative to endogenous levels, explaining why it partially suppresses mTORC1 signaling. The Sestrin2 E451A mutant is expressed at levels similar to the endogenous protein.

In order to determine whether leucine binding to any of Sestrin1-3 is required for proper localization of mTORC1, we performed immunofluorescence localization of RagC and/or mTOR, as well as LAMP2 as a control in Sestrin1-3 triple mutant HEK-293T cells stably expressing FLAG-tagged wild-type or the L261A or E451A non-leucine binding mutant Sestrin2. The cells were deprived of leucine for 50 minutes and then either processed for immunofluorescence or treated with leucine for 10 minutes and then processed for immunofluorescence.

Immunofluorescence assays were performed as described in (Y. Sancak et al., Ragulator-Rag complex targets mTORC1 to the lysosomal surface and is necessary for its activation by amino acids. Cell 141, 290-303 (2010)). Briefly, 400,000 HEK-293T cells were plated on fibronectin-coated glass coverslips in 6-well tissue culture plates. Twenty-four hours later, the slides were rinsed once with PBS and fixed with 4% paraformaldehyde in PBS for 15 min at room temperature. The slides were subsequently rinsed three times with PBS and cells were permeabilized with 0.05% Triton X-100 in PBS for 5 min. After rinsing three times with PBS, cells were incubated with primary antibody in Odyssey blocking buffer for 1 hr at room temperature, rinsed three times with PBS, and incubated with secondary antibodies produced in donkey (diluted 1:400 in Odyssey blocking buffer) for 45 minutes at room temperature in the dark and washed three times with PBS. Slides were mounted on glass coverslips using Vectashield® (Vector Laboratories) and cells imaged on a spinning disk confocal system (Perkin Elmer).

As shown in FIG. 12D-12G, in Sestrin1-3 triple null cells expressing the mutant Sestrin2, the localization of mTOR to lysosomes in the presence of leucine was decreased, while that of RagC was not affected. Thus, activation of mTORC1 by leucine requires the binding of leucine to Sestrin2.

Example 12

ELISA Assays

HEK293T cells engineered to co-express HA-tagged GATOR2 complex and FLAG-tagged Sestrin2 are starved for leucine for at least 50 minutes to promote the interaction between Sestrin2 and the GATOR2 complex. Cells are then lysed, and the GATOR2 complex is immobilized on an ELISA plate via anti-HA antibodies. Varying concentrations of test compounds are then added to each well for an amount of time sufficient for them to affect the GATOR2-Sestrin2 interaction. DMSO is used as a negative control in place of the test compound. Leucine may be used as a positive control. The ELISA is then finished by detecting co-bound Sestrin2 via a horseradish peroxidase (HRP)-conjugated anti-FLAG antibody followed by a suitable HRP substrate. Test compounds that decrease the ELISA signal in a statistically significant manner compared to the DMSO control will be scored as a hit.

The above ELISA assay is also adapted to identify test compounds that promote the interaction of GATOR2 and Sestrins. HEK293T cells engineered to express a FLAG-tagged GATOR2 complex are grown and then lysed in the presence of leucine. Leucine inhibits the GATOR2-Sestrin interaction and prevents any native Sestrin from binding to the tagged GATOR2 complex. The lysate from these cells is immobilized on anti-HA antibody coated ELISA plates. HEK293T cells engineered to express FLAG-tagged Sestrin2 are grown and then lysed in the presence of leucine and resulting lysates plus test compounds to be screened are added to ELISA wells. The interaction between GATOR2 and Sestrin2 is probed using anti-FLAG antibody conjugated to HRP as described above. Compounds that promote binding between GATOR2 and Sestrin2 as measured by a statistically significant increase in signal will be scored as hits.

In either of the assays set forth above, HRP-conjugated antibodies may be replaced with fluorescent lanthanide or europium-conjugated antibodies (such as DELFIA® TRF from Perkin Elmer) and the signal read out using a spectrophotometer. Also, in either of the assays set forth above, Sestrin2 can be immobilized on the ELISA plate and changes in GATOR2 complex binding measured using appropriate antibodies.

Example 13

Solution Phase Assays

Commercial technology that uses energy transfer mediated fluorescence emission (e.g. Amplified Luminescent Proximity Homogeneous Assay technology by Perkin Elmer or Fluorescence/Förster Resonance Energy Transfer) is also used to measure the interaction between HA-tagged GATOR2 and FLAG-tagged Sestrin2. The proteins can either be separately expressed and purified or simply co-expressed in cells. HEK293T cells co-expressing HA-tagged GATOR2 and FLAG-Sestrin2 are lysed under substantially leucine-free conditions and the resulting lysate is added to wells of an assay plate along with test compounds to be screened. After incubation with test compounds, anti-HA antibodies conjugated to a donor FRET molecule and anti-FLAG antibodies conjugated to a corresponding acceptor FRET molecule are added and subsequent fluorescent emission is assayed. Compounds that reduce the fluorescent signal in a statistically significant manner due to disrupting the complex are scored as potential inhibitors of the GATOR2-Sestrin interaction.

This solution-based FRET method is also employed with tagged GATOR2 and Sestrin proteins isolated from cells in the presence of leucine. Test compounds that promote the interaction between GATOR2 and Sestrin2 can be screened and identified in wells where the fluorescent signal is increased.

A variation of these assays is performed with GATOR2 and Sestrin2 each fused to a complementary polypeptide fragment of a reporter protein, such as luciferase or a fluorescent protein, such YFP. In this variation, neither GATOR2 nor Sestrin need comprise an epitope tag, as no antibodies are used in detection. Rather, when GATOR2 and Sestrin interact, the reporter protein polypeptide fragments reconstitute non-covalently and emit a signal.

Other variations include direct conjugation of a FRET donor onto one of GATOR2 or Sestrin, and direct conjugation of a corresponding FRET acceptor onto the other; the use of complementary polypeptide fragments of an enzyme on GATOR2 and Sestrin, followed by detection using a colorimetric substrate for that enzyme; and the use of complementary polypeptide fragments of an enzyme on the anti-FLAG and anti-HA antibodies to detect the interaction between HA-tagged GATOR2 and FLAG-Sestrin.

Example 14

Solid Phase Surface Plasmon Resonance Assays

Highly purified GATOR2 complex (free of bound Sestrin) is immobilized to a matrix plate for a surface plasmon resonance assay device (e.g. Biacore, ForteBio). The immobilization can occur through direct amine coupling of the protein to the plate or through the addition of an avidity-tag such as biotin to the GATOR2 protein and tethering the tagged protein to a streptavidin-coated matrix. Purified Sestrin2 is then added to each well in the absence or presence of varying concentrations of test compound and the resulting binding and dissociation curves of GATOR2-Sestrin2 are then analyzed. Compounds that either statistically increase or decrease the binding affinity of Sestrin2 for GATOR2 as compared to a negative control are identified as modulators of the GATOR2-Sestrin interaction and as potential mTORC1 antagonists or agonists, respectively. Test compounds that promote binding of Sestrin2 to GATOR2, can be re-assayed at various concentrations in the presence of leucine to determine their relative potency for promoting interaction in the presence of leucine at levels sufficient to disrupt the interaction. This assay can also be performed in a reciprocal manner whereby avidity-tagged-Sestrin2 is immobilized to the corresponding matrix and the binding affinity of the purified GATOR2 component that directly binds Sestrin2 is assessed in the presence or absence of compound. The assay is also performed to screen for compounds that directly bind purified Sestrin2. Compounds identified in this manner then are assayed for modulation of the Sestrin2/GATOR2 interaction or for modulation of the affinity of Sestrin2 for leucine binding.

Example 15

Solution Based Fluorescence Polarization Assay

A small polypeptide comprising the GATOR2-binding domain of Sestrin2 (MW<1.5 kD) is coupled to 5-carboxyfluorecein via its N or C-terminus in a manner that does not disrupt its ability to interact with the GATOR2 complex. The resulting peptide is then incubated in the presence or absence of test compound and highly purified GATOR2 complex for 30 minutes. The binding of the 5-carboxyfluorecein-tagged Sestrin2 peptide to the GATOR2 complex is then measured on a luminescence spectrometer equipped with polarizers. The fluorophore is excited with vertical polarized light at the appropriate excitation wavelength and the polarization value of the emitted light is observed through vertical and horizontal polarizers at the corresponding emission wavelength. The ability of the test compound to disrupt the interaction between GATOR2 and the GATOR2 binding fragment of Sestrin2 is assessed by determining the fluorescence through each of the polarizers. When GATOR2 and the GATOR2 binding fragment of Sestrin interact, more fluorescence will be observed through the vertical polarizer (because more of the emitted fluorescence is in the same plane as that of the excitation wavelength than when the two do not interact).

This assay can also be performed in a reciprocal manner using a peptide corresponding to the domain on GATOR2 that binds Sestrin2 and full-length Sestrin2.

Example 16

Western Blot Assay and Confirmation Assays
Western Blot after 30 Minute Incubation This screening assay measured test compound activity in vitro on GATOR2/Sestrin2 complexes purified via immunoprecipitation of stably expressed FLAG-WDR24 from HEK293T cells. HEK293T cells (293 Ts) were engineered to stably express N-terminally tagged FLAG-WDR24 via transduction by lentivirus. Lentiviruses were produced by co-transfection of the lentiviral transfer vector pLJM60 with the ΔVPR envelope and CMV VSV-G packaging plasmids into HEK-293T cells using the XTremeGene 9 transfection reagent (Roche Diagnostics). The media was changed 24 hours post-transfection to Dulbecco's Modified Eagle's media (DMEM) supplemented with 30% Inactivated Fetal Serum. The virus-containing supernatants were collected 48 and 72 hours after transfection and passed through a 0.45 μm filter to eliminate cells. Target cells in 6-well tissue culture plates were infected in media containing 8 μg/mL polybrene and spin infections were performed by centrifugation at 2,200 rpm for 1 hour. Twenty-four hours after infection, the virus was removed and the cells selected with the appropriate antibiotic. Cells were then grown in DMEM supplemented with 10% fetal bovine serum and antibiotics.

To screen for leucine mimetic compounds, 2,000,000 FLAG-WDR24 expressing 293T cells were plated in a 10 cm tissue culture plate. Seventy-two hours later, cells were placed in standard RPMI media formulated with no amino acids and supplemented with 5 mM Glucose (-AA RPMI, US Biological Life Sciences) for 1 hour then subsequently lysed in lysis buffer (40 mM HEPES, 1% Triton, 10 mM sodium β-glycerophosphate, 10 mM sodium pyrophosphate, 2.5 mM $MgCl_2$ and protease inhibitors). To isolate the FLAG-WDR24/endogenous-Sestrin2 complex, crude lysate (equivalent to 2-4 mg of total protein) in a volume of 1 ml was subjected to immunoprecipitation with 30 μl of anti-flag resin (SIGMA) for 2 hours at 4° C., washed twice in cold lysis buffer plus 0.5M NaCl and resuspended in 1 ml of cold cytosolic buffer (40 mM HEPES pH 7.4, 140 mM KCl, 10 mM NaCl, 2.5 mM MgCl2, 0.1% TritonX-100). Test compounds or controls (water or leucine) were then added to each immunoprecipitation sample at various concentrations and incubated with rotation at 4° C. for 60 minutes. After the incubation period, samples were centrifuged to pellet the FLAG-WDR24/endogenous-Sestrin2 complex bound to the anti-flag resin, the supernatant was completely removed and resin was resuspended in SDS-PAGE sample buffer and boiled for 5 minutes. Samples were then processed by SDS-PAGE and western blots were performed with anti-FLAG (SIGMA) and anti-Sestrin2 (Cell Signaling Technology) antibodies as described in L. Chantranupong, et al., *Cell Reports* 9:1-8 (2014).

Figure 13:
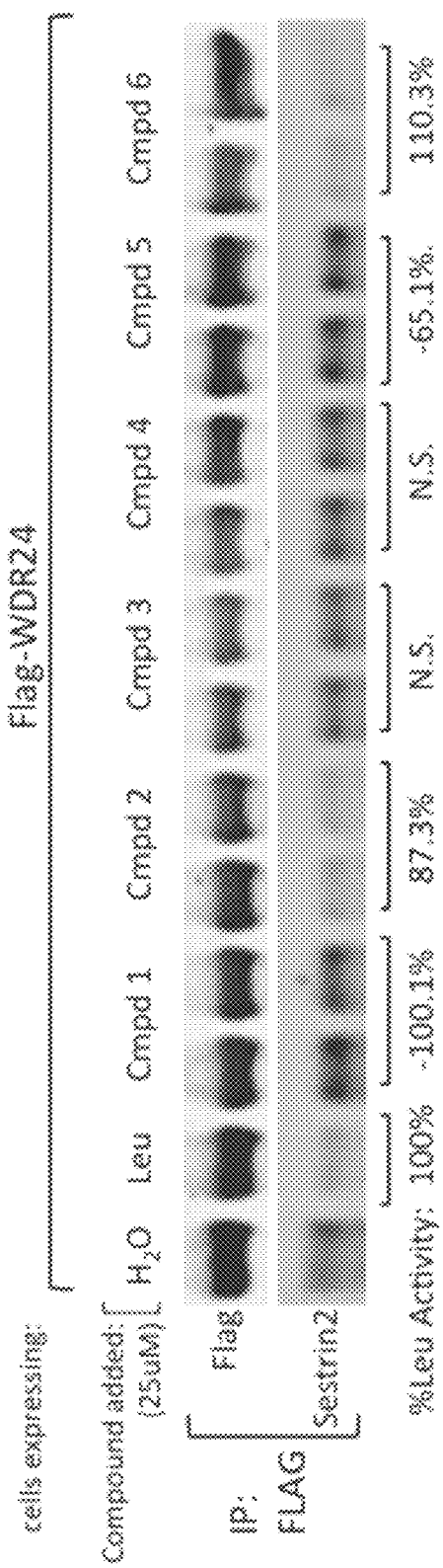
FIG. 13 depicts an anti-FLAG and anti-Sestrin2 immunoblot from HEK-293T cells expressing FLAG-tagged WDR24 starved of amino acids for 60 minutes, lysed, immunoprecipitated with anti-FLAG resin and then incubated with various test or control compounds for 60 minutes.

The resulting western blots were scanned and band intensities corresponding to Sestrin2 and FLAG-WDR24 were quantified using the LI-COR® imaging platform. To determine the amount of Sestrin2 bound to GATOR2 for each condition, the band intensity for Sestrin2 was normalized to the band intensity of FLAG-WDR24. For every batch of compounds tested, a negative control (water) and a positive control (leucine, 25 µM, SIGMA) were also performed. The depletion of bound endogenous Sestrin2 to FLAG-WDR24 by leucine was normalized to represent 100% activity. Compounds were assayed in duplicate and activity of each compound was quantified as percent of leucine activity and averaged. Repeated attempts of the assay resulted in a standard deviation of 20% in the average activity of leucine compared to water; therefore, test compounds that reduce the amount of Sestrin2 bound to GATOR2 by at least 40% at 25 µM in duplicate were considered statistically significant and were characterized as leucine mimetics. Some compounds increased the amount of Sestrin2 bound to FLAG-WDR24. Compounds that increased the amount of Sestrin2 bound to GATOR2 by more than 40% (represented as less than −40% of leucine activity) were characterized as leucine antagonists. FIG. 13 shows results obtained for 6 different test compounds and their corresponding values for average % activity of leucine. This in vitro assay was used to screen over 40 test compounds and resulted in the identification of nine leucine mimetics and four leucine antagonists. The activity of twelve of the thirteen hit compounds was confirmed in vitro by a dose response study, and three of the nine mimetics and two of the four antagonists have been confirmed to also modulate mTORC1 in the expected manner in intact cells.

Time-Course Western Blot Over 120 Minute Incubation

Figures 14A, 14B, 14C:
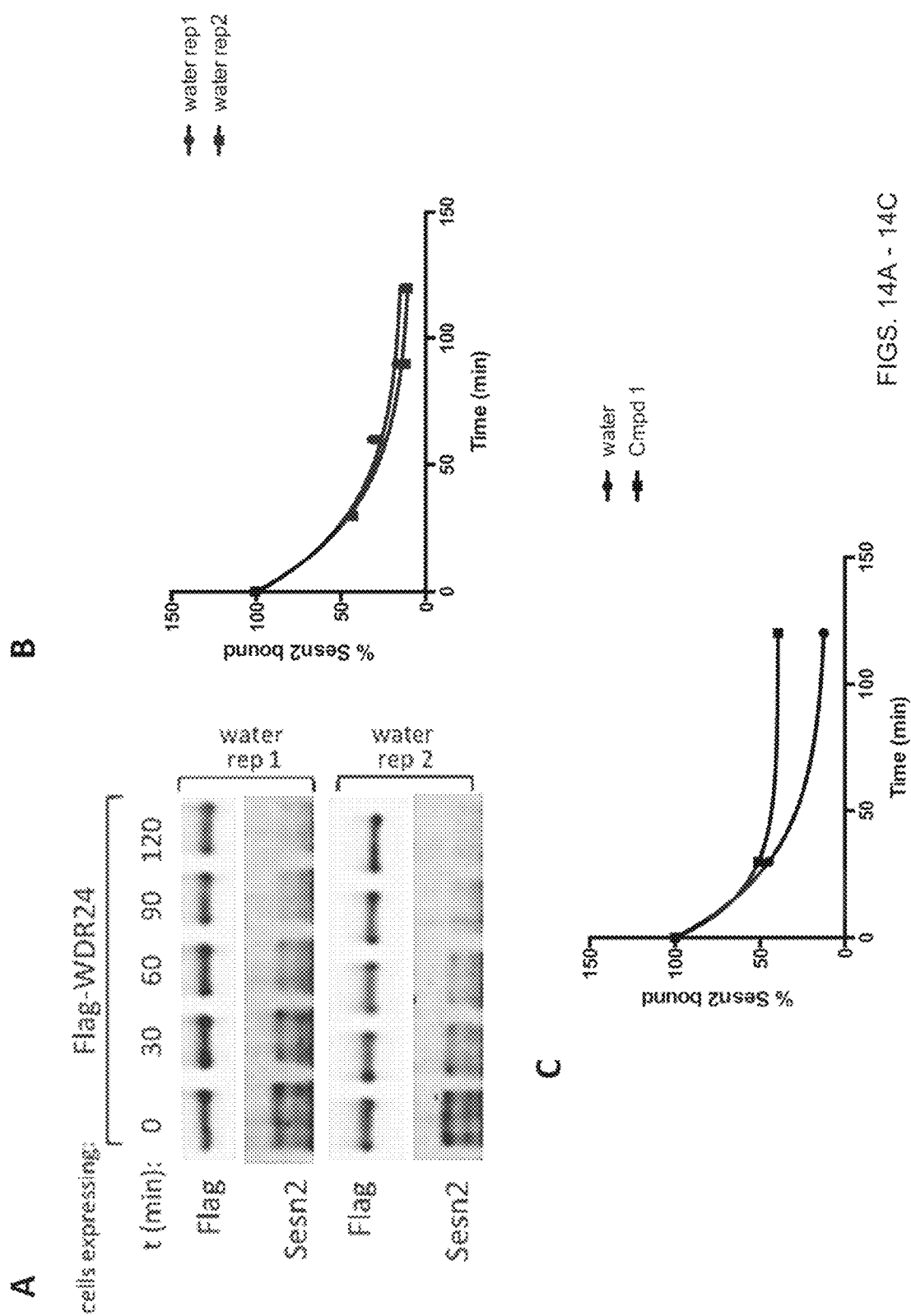
FIGS. 14A, 14B, and 14C.

We determined that the half-life of bound Sestrin2 in the GATOR2-Sestrin2 complex is approximately 22 minutes. This measurement was performed by immunoprecipitation of the GATOR2-Sestrin2 complex via stably expressed FLAG-WDR24, and, at various times after, adding water as a negative control (FIGS. 14A and 14B). To confirm that compounds identified as leucine antagonists prevent the baseline dissociation of endogenous Sestrin2 from GATOR2, the same assay described above was repeated, but samples for western blotting were collected at 0, 30, and 120 minutes after compound addition instead of 60 minutes, and the amount of Sestrin2 hound to FLAG-WDR24 was normalized to time=0 min. These time points were chosen to cover ~90% loss of Sestrin2 from GATOR2 in the presence of water. Test compounds that significantly increased the amount of Sestrin2 bound to GATOR2 at time=30 and/or 60 minutes, as determined by statistical significance (student t-test, p<0.05) over replicate experiments, were confirmed as being leucine antagonists. FIG. 14C shows that one of the test compounds previously identified as a leucine antagonist by the prior method (Cmpd 1) was confirmed to significantly increase the amount of Sestrin2 bound to GATOR2 at 60 minutes as compared to water.

Confirmation Assay for Leucine Mimetics Identified by Western Blotting

Upon leucine starvation, addition of exogenous leucine activates mTORC1 when signaling is measured 10 to 90 minutes after addition of leucine (Wang, S., Tsun, Z., et al. Science 347:188-194 (2015)). Based on this, we designed an assay to test whether compounds identified as leucine mimetics in the previous western blotting assay could activate mTORC1 signaling following leucine starvation in intact cells.

Briefly, 800,000 HEK293T cells were plated in each well of a 6-well plate in DMEM supplemented with 10% fetal bovine serum and antibiotics. The next day, cells were placed in modified DMEM without leucine (Thermo Scientific) or serum for 1 hour followed by addition of leucine mimetic (n=3) at a given concentration for 60 minutes. Cells were then lysed, processed for SDS-PAGE and western blotting was performed with antibodies directed against the mTORC1 substrates phosphorylated S6 Kinase (pS6K) (Thr389) and phosphorylated 4E-BP1 (Thr37/46) (Cell Signaling Technology) and loading controls (beta-actin, Santa Cruz Biotechnology) (Kang, S. A., et al. Science 341(6144): 364-374 (2013)). The intensity of the bands corresponding to the phosphorylated substrates were then normalized to the actin band using the LI-COR® imaging platform. Compounds that significantly increased mTORC1 signaling relative to leucine-starved cells treated with no compound (student t-test, p<0.05) were confirmed as leucine mimetics. As a positive control, leucine was added at 100 µM to leucine-starved cells for 60 minutes.

Confirmation Assay for Leucine Antagonists Identified by Western Blotting

Figures 15A, 15B:
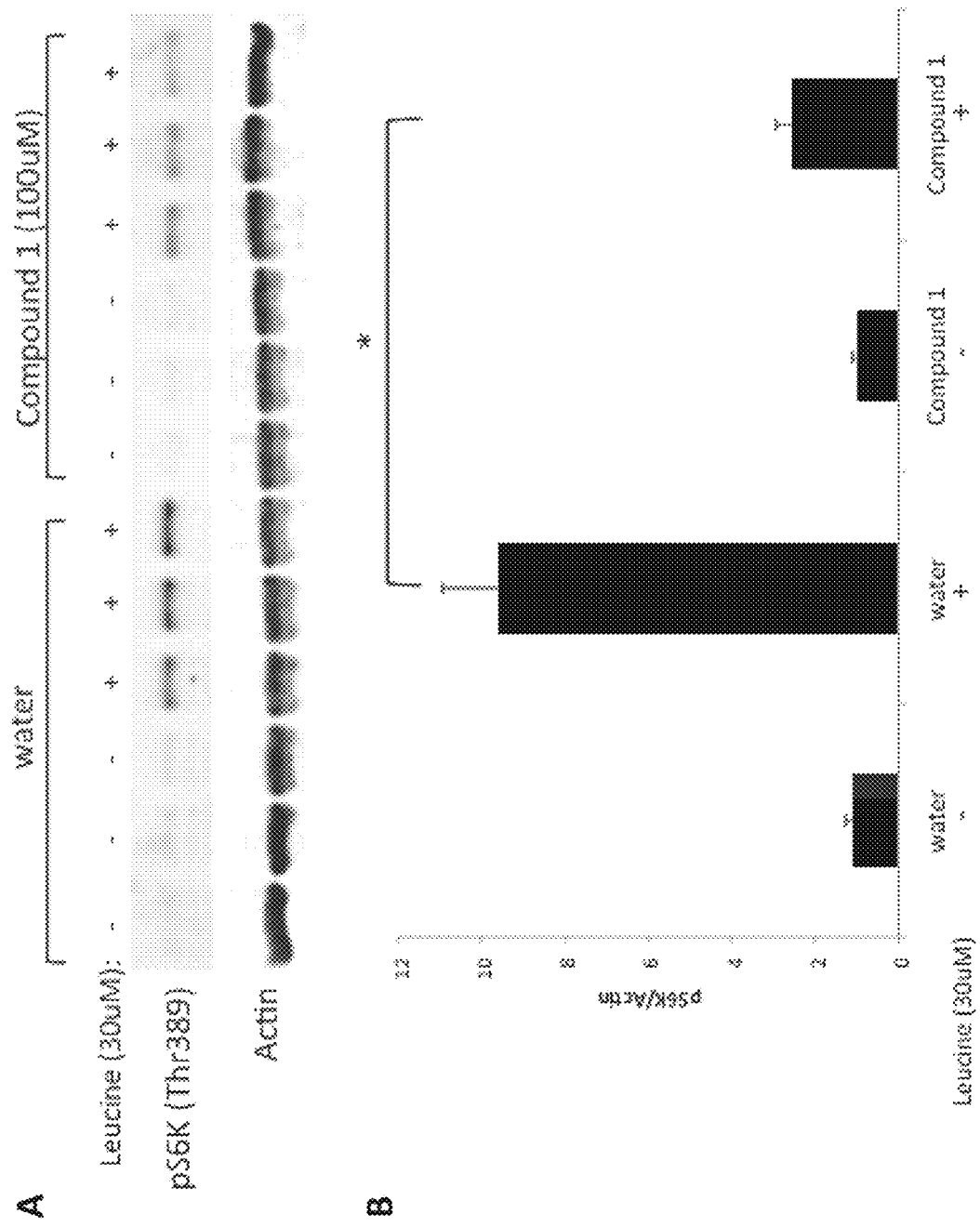
FIGS. 15A and 15B.

To confirm the activity of compounds identified as leucine antagonists in intact cells, the same assay described above was carried out with the following changes: cells were placed in leucine-minus DMEM media (as described above) for 30 minutes followed by incubation with test compound (n=3) for an additional 30 minutes. After test compound treatment, the cells were stimulated with 30 and 100 µM of leucine for 60 minutes. mTORC1 signaling was measured via western blotting as described above. Compounds that reduced levels of actin-normalized phosphorylated substrates of mTORC1 (i.e., lower pS6K/actin ratio) in response to leucine at either 30 µM or 100 µM in a statistically significant manner (student t-test, p<0.05) were considered confirmed as leucine antagonists. FIGS. 15A and 15B demonstrate that Compound 1, previously identified as a putative leucine antagonist in both the 30 minute and 120 minute time course western blotting assays, caused a significant reduction in pS6K/actin ratio in the presence of 30 µM leucine as compared to control, i.e. leucine-starved cells that were pre-treated with water prior to addition of leucine.

Another method for determining the ability of hit test compounds to modulate the interaction between Sestrin2 and GATOR2 is to carry out the confirmatory assays described above in HEK293T cells engineered to stably express FLAG-WDR24 plated in 10 cm tissue culture dishes. The interaction between endogenous Sestrin2 and FLAG-WDR24 is measured from lysate obtained from cells after test compound treatment (n=3). The lysate is obtained as described in the 30 minute western blot assay procedure above.

To measure the amount of endogenous Sestrin2 bound to FLAG-WDR24 after cell treatment, an immunoprecipitation is performed with the anti-FLAG resin and the resulting samples are processed for SDS-PAGE and western blotting to measure amount of endogenous Sestrin2 bound to FLAG-WDR24. Compounds that modulate the amount of Sestrin2 bound to GATOR2 in a statistically significant manner (student t-test, p<0.05) are considered confirmed hits.

Example 17

AlphaLISA® Assay

Identifying compounds that modulate the Sestrin2/WDR24 interaction may also be determined in a high-throughput manner using the AlphaLISA® technology developed by Perkin Elmer. HEK293T cells stably expressing FLAG-WDR24 (as described in the 30 minute western blotting assay above) were transiently transfected with 10 to 160 ng of N-terminal tagged HA-Sestrin2 as described in the art (Chantranupong, L., et al. Cell Reports 9:1-8 (2014)). Forty-eight hours post-transfection, cells were lysed in lysis buffer (as described above) plus the addition of 150 mM NaCl. The resulting lysate was diluted to between 0.3 ng/µl to 300 ng/µl of total protein for use in this assay. Lysate can also be generated from HEK293T cells transiently transfected with FLAG or HA-tagged WDR24 and FLAG or HA-tagged Sestrin2 as performed in the art (Chantranupong, L., et al. Cell Reports 9:1-8 (2014)).

Figures 16A, 16B, 16C, 16D:
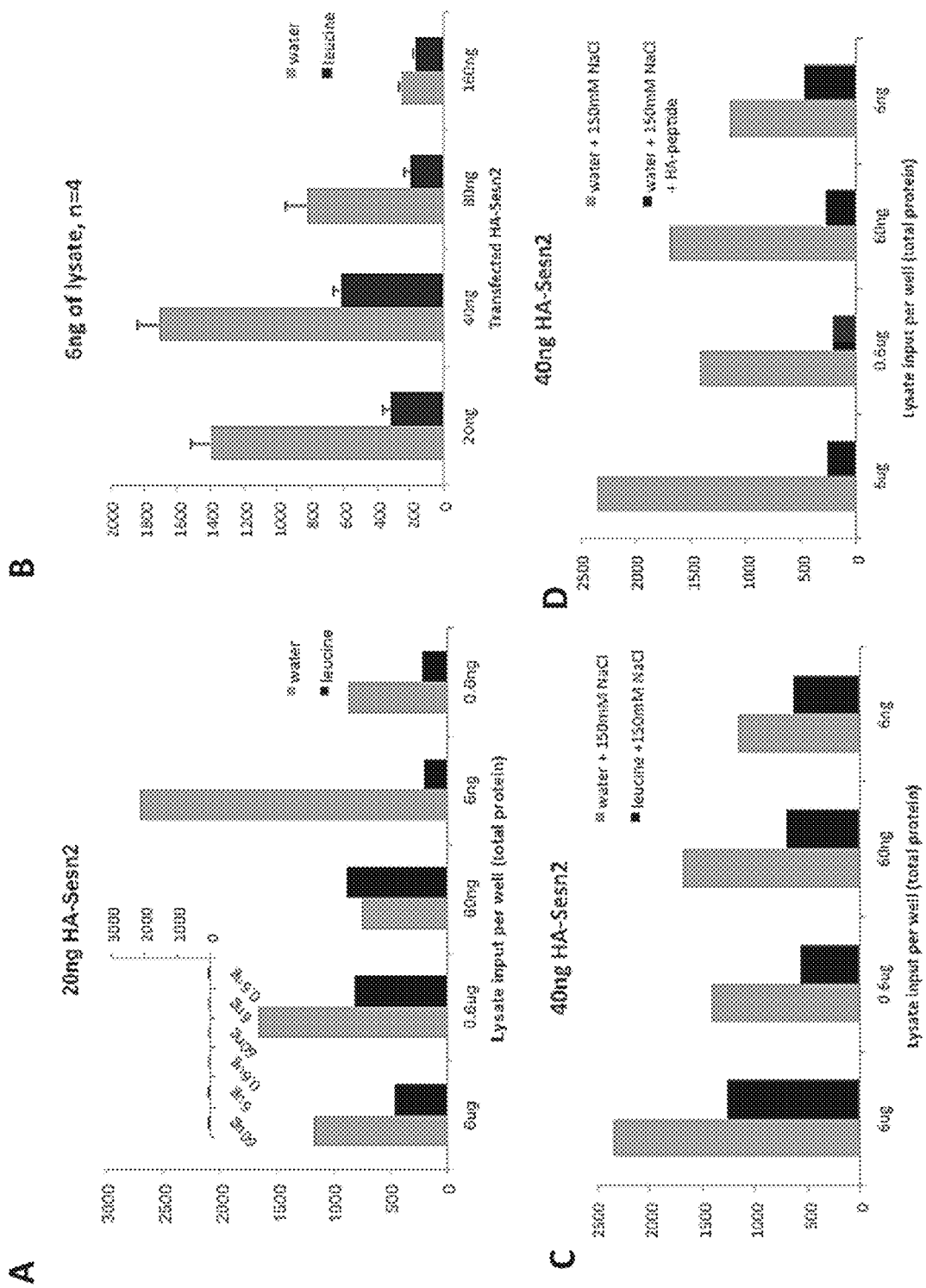
FIGS. 16A, 16B, 16C and 16D.

The lysate is incubated with test compound (n=3) for 30 to 60 minutes at 4° C. with agitation in a 384-well plate); leucine (100 µM) is used as a positive control compound and water is used as a negative control compound (FIG. 16A). As an additional negative control, lysate from HEK293T cells stably expressing FLAG-WDR24 transfected with empty vector is used (FIG. 16A, inset). After compound incubation, FLAG-donor beads and HA-acceptor beads (Perkin Elmer) are diluted in lysis buffer plus 150 mM NaCl and added simultaneously at a final concentration ranging between 5-80 µg/ml for 3 hours at 4° C. Alternatively, biotinylated anti-HA antibody (SIGMA) is added to lysate at a final concentration of 1 nM for 1 hour prior to simultaneous addition of FLAG-donor and streptavidin-acceptor beads (Perkin Elmer) at concentrations ranging from 5-80 µg/ml (FIG. 16C). Alternatively, compound treatment can also be performed after addition of AlphaLISA® bead reagents. Negative controls for this iteration of the assay include the use of biotinylated HA peptides at concentrations required to suppress the assay signal (FIG. 16D).

For a 384-well plate, the total assay volume for each well is 25 µL The assay plate is then processed to generate a final signal according to manufacturer's protocol. Compounds that significantly reduce the AlphaLISA® signal compared to the negative controls (student t-test, p<0.05) are considered hits and would be characterized as leucine mimetics. Compounds that significantly increase the signal compared to the negative controls would be considered potential leucine antagonists.

The assay is alternatively performed with lysate from cells treated with compounds prior to lysis. In this iteration, HEK293T cells stably expressing FLAG-WDR24 (as described above) are transiently transfected with 10 to 160 ng of N-terminal tagged HA-Sestrin2. Twenty-four hours after transfection, cells are trypsinized and plated into a 96-well plate. The following day, cells are starved for amino acids and treated with compounds as described in the confirmatory methods set forth above. After compound treatment, cells are lysed in lysis buffer (as described above) at a volume of 100 µl per 2×10$^5$ cells. The resulting lysate is processed in the AlphaLISA® assay as described above.

Example 18

Sestrin Binding Assays
Radioligand Binding Assay

Screening for leucine mimetics, leucine antagonists or other compounds that either increase or decrease the affinity of leucine for Sestrin1 or Sestrin2 is also performed through the use of direct binding assays that measure the binding of leucine to purified Sestrin1 or Sestrin2 in a quantitative manner.

One such assay is a radioligand binding assay (Maguire J J et al. Methods Mol Biol. 897:31-77 (2012)) that measures the binding of [$^3$H]-Leucine to purified Sestrin1 or Sestrin2 in either a kinetic manner or with saturating amounts of $^3$H-Leucine at equilibrium. Compounds are screened for their ability to modulate the $K_d$ of leucine for purified Sestrin1 or Sestrin2. Compounds that increase the $K_d$ of leucine for Sestrin1 or Sestrin2 are considered mTORC1 inhibitors while compounds that decreased the Kd would be considered activators of mTORC1.

REFERENCES

Bamford, S., Dawson, E., Forbes, S., Clements, J., Pettett, R., Dogan, A., Flanagan, A., Teague, J., Futreal, P. A., Stratton, M R., et al. (2004). The COSMIC (Catalogue of Somatic Mutations in Cancer) database and website. British Journal of Cancer.

Bar-Peled, L., Chantranupong, L., Cherniack, A. D., Chen, W. W., Ottina, K. A., Grabiner, B. C., Spear, E. D., Carter, S. L., Meyerson, M., and Sabatini, D. M. (2013). A Tumor Suppressor Complex with GAP Activity for the Rag GTPases That Signal Amino Acid Sufficiency to mTORC1. Science 340, 1100-1106.

Bar-Peled, L., and Sabatini, D. M. (2014). Regulation of mTORC1 by amino acids. Trends in cell biology 24, 400-406.

Bar-Peled, L., Schweitzer, L. D., Zoncu, R., and Sabatini, D. M. (2012). Ragulator Is a GEF for the Rag GTPases that Signal Amino Acid Levels to mTORC1. Cell 150, 1196-1208.

Boussif, O., Lezoualc'h, F., Zanta, M. A., Mergny, M. D., Scherman, D., Demeneix, B., and Behr, J. P. (1995). A versatile vector for gene and oligonucleotide transfer into cells in culture and in vivo: polyethylenimine. Proceedings of the National Academy of Sciences of the United States of America 92, 7297-7301.

Brugarolas, J., Lei, K., Hurley, R. L., Manning, B. D., Reiling, J. H., Hafen, E., Witters, L. A., Ellisen, L. W., and Kaelin, W. G. (2004). Regulation of mTOR function in response to hypoxia by REDD1 and the TSC1/TSC2 tumor suppressor complex. Genes & Development 18, 2893-2904.

Buckbinder, L., Talbott, R., Seizinger, B. R., and Kley, N. (1994). Gene regulation by temperature-sensitive p53 mutants: identification of p53 response genes. Proceedings of the National Academy of Sciences of the United States of America 91, 10640-10644.

Budanov, A. V., and Karin, M. (2008). p53 Target Genes Sestrin1 and Sestrin2 Connect Genotoxic Stress and mTOR Signaling. Cell 134, 451-460.

Budanov, A. V., Lee, J. H., and Karin, M. (2010). Stressin' Sestrins take an aging fight. EMBO Molecular Medicine 2, 388-400, Budanov, A. V., Sablina, A. A., Feinstein, E., Koonin, E. V., and Chumakov, P. M. (2004). Regeneration of peroxiredoxins by p53-regulated Sestrins, homologs of bacterial AhpD. Science 304, 596-600, Budanov, A. V., Shoshani, T., Faerman, A., Zelin, E., Kamer, I., Kalinski, H., Gorodin, S., Fishman, A., Chajut, A., Einat, P., et al. (2002). Identification of a novel stress-responsive gene Hi95 involved in regulation of cell viability. Oncogene 21, 6017-6031.

Buerger, C., DeVries, B., and Stambolic, V. (2006). Localization of Rheb to the endomembrane is critical for its signaling function. Biochemical and Biophysical Research Communications 344, 869-880.

Dibble, C. C., Elis, W., Menon, S., Qin, W., Klekota, J., Asara, J. M., Finan, P. M., Kwiatkowski, D. J., Murphy, L. O., and Manning, B. D. (2012). TBC1D7 is a third subunit of the TSC1-TSC2 complex upstream of mTORC1. Molecular cell 47, 535-546.

Efeyan, A., Zoncu, R., Chang, S., Gumper, I., Snitkin, H., Wolfson, R. L., Kirak, O., Sabatini, D. D., and Sabatini, D. M. (2012a). Regulation of mTORC1 by the Rag GTPases is necessary for neonatal autophagy and survival. Nature 493, 679-683.

Efeyan, A., Zoncu, R., and Sabatini, D. M. (2012b). ScienceDirect.com—Trends in Molecular Medicine—Amino acids and mTORC1: from lysosomes to disease. Trends in Molecular Medicine.

Fingar, D. C., Salama, S., Tsou, C., Harlow, E., and Blenis, J. (2002). Mammalian cell size is controlled by mTOR and its downstream targets S6K1 and 4EBP1/eIF4E. Genes Dev 16, 1472-1487.

Garami, A., Zwartkruis, F., Nobukuni, T., and Joaquin, M. (2003). ScienceDirect.com—Molecular Cell—Insulin Activation of Rheb, a Mediator of mTOR/S6K/4E-BP Signaling, Is Inhibited by TSC1 and 2. Molecular cell.

Hirose, E., Nakashima, N., Sekiguchi, T., and Nishimoto, T. (1998). RagA is a functional homologue of S. cerevisiae Gtr1p involved in the Ran/Gsp1-GTPase pathway. Journal of cell science 111 (Pt 1), 11-21.

Howell, J. J., Ricoult, S. J. H., Ben Sahra, I., and Maiming, B. D. (2013). A growing role for mTOR in promoting anabolic metabolism. Biochemical Society transactions 41, 906-912.

Inoki, K., Li, Y., Xu, T., and Guan, K.-L. (2003). Rheb GTPase is a direct target of TSC2 GAP activity and regulates mTOR signaling. Genes & Development 17, 1829-1834.

Kim, D.-H., Sarbassov, D. D., Ali, S. M., King, J. E., Latek, R. R., Erdjument-Bromage, H., Tempst, P., and Sabatini, D. M. (2002). mTOR Interacts with Raptor to Form a Nutrient-Sensitive Complex that Signals to the Cell Growth Machinery. Cell 110, 163-175.

Kim, E., Goraksha-Hicks, P., Li, L., Neufeld, T. P., and Guan, K.-L. (2008). Regulation of TORC1 by Rag GTPases in nutrient response. Nature cell biology 10, 935-945.

Kim, S. G., Buel, G. R., and Blenis, J. (2013). Nutrient regulation of the mTOR Complex 1 signaling pathway. Molecules and cells 35, 463-473.

Laplante, M., and Sabatini, D. M. (2012). mTOR Signaling in Growth Control and Disease. Cell 149, 274-293.

Long, X., Lin, Y., Ortiz-Vega, S., Yonezawa, K., and Avruch, J. (2005). Rheb Binds and Regulates the mTOR Kinase. Current Biology 15, 702-713.

Menon, S., Dibble, C. C., Talbott, G., Hoxhaj, G., Valvezan, A. J., Takahashi, H., Cantley, L. C., and Manning, B. D. (2014). Spatial Control of the TSC Complex Integrates Insulin and Nutrient Regulation of mTORC1 at the Lysosome. Cell 156, 771-785.

Nobukuni, T., Joaquin, M., Roccio, M., Dann, S. G., Kim, S. Y., Gulati, P., Byfield, M. P., Backer, J. M., Natt, F., Bos, J. L., et al. (2005). Amino acids mediate mTOR/raptor signaling through activation of class 3 phosphatidylinositol 3OH-kinase. Proceedings of the National Academy of Sciences of the United States of America 102, 14238-14243.

Panchaud, N., Peli-Gulli, M.-P., and De Virgilio, C. (2013). Amino Acid Deprivation Inhibits TORC1 Through a GTPase-Activating Protein Complex for the Rag Family GTPase Gtr1. Science Signaling 6, ra42.

Peeters, H., Debeer, P., Bairoch, A., Wilquet, V., Huysmans, C., Parthoens, E., Fryns, J. P., Gewillig, M., Nakamura, Y., Niikawa, N., et al. (2003). PA26 is a candidate gene for heterotaxia in humans: identification of a novel PA26-related gene family in human and mouse. Human genetics 112, 573-580.

Petit, C. S., Roczniak-Ferguson, A., and Ferguson, S. M. (2013). Recruitment of folliculin to lysosomes supports the amino acid-dependent activation of Rag GTPases. The Journal of Cell Biology 202, 1107-1122.

Roccio, M., Bos, J. L., and Zwartkruis, F. J. T. (2005). Regulation of the small GTPase Rheb by amino acids. Oncogene 25, 657-664.

Saito, K., Araki, Y., Kontani, K., Nishina, H., and Katada, T. (2005). Novel role of the small GTPase Rheb: its implication in endocytic pathway independent of the activation of mammalian target of rapamycin. Journal of Biochemistry 137, 423-430.

Sancak, Y., Bar-Peled, L., Zoncu, R., Markhard, A. L., Nada, S., and Sabatini, D. M. (2010a). Ragulator-Rag complex targets mTORC1 to the lysosomal surface and is necessary for its activation by amino acids. Cell 141, 290-303.

Sancak, Y., Bar-Peled, L., Zoncu, R., Markhard, A. L., Nada, S., and Sabatini, D. M. (2010b). Ragulator-Rag complex targets mTORC1 to the lysosomal surface and is necessary for its activation by amino acids. Cell 141, 290-303.

Sancak, Y., Peterson, T. R., Shaul, Y. D., Lindquist, R. A., Thoreen, C. C., Bar-Peled, L., and Sabatini, D. M. (2008). The Rag GTPases bind raptor and mediate amino acid signaling to mTORC1. Science (New York, N.Y.) 320, 1496-1501.

Saucedo, L. J., Gao, X., Chiarelli, D. A., Li, L., Pan, D., and Edgar, B. A. (2003). Rheb promotes cell growth as a component of the insulin/TOR signalling network. Nature cell biology 5, 566-571.

Schmittgen, T. D., and Livak, K. J. (2008). Analyzing real-time PCR data by the comparative CT method. Nature Protocols 3, 1101-1108.

Schürmann, A, Brauers, A., Maßmann, S., Becker, W., and Joost, H.-G. (1995). Cloning of a Novel Family of Mammalian GTP-binding Proteins (RagA, RagBs, RagB1) with Remote Similarity to the Ras-related GTPases. The Journal of biological chemistry 270, 28982-28988.

Sekiguchi, T., Hirose, E., Nakashima, N., Ii, M., and Nishimoto, T. (2001). Novel G proteins, Rag C and Rag D, interact with GTP-binding proteins, Rag A and Rag B. The Journal of biological chemistry 276, 7246-7257.

Smith, E. M., Finn, S. G., Tee, A. R., Browne, G. J., and Proud, C. G. (2005). The tuberous sclerosis protein TSC2 is not required for the regulation of the mammalian target of rapamycin by amino acids and certain cellular stresses. The Journal of biological chemistry 280, 18717-18727.

Stocker, H, Radimerski, T., Schindelholz, B., Wittwer, F., Belawat, P., Daram, P., Breuer, S., Thomas, G., and Hafen, E. (2003). Rheb is an essential regulator of S6K in controlling cell growth in *Drosophila*. Nature cell biology 5, 559-565.

Tee, A. R., Fingar, D. C., Manning, B. D., Kwiatkowski, D. J., Cantley, L. C., and Blenis, J. (2002). Tuberous sclerosis complex-1 and -2 gene products function together to inhibit mammalian target of rapamycin (mTOR)-mediated downstream signaling. Proceedings of the National Academy of Sciences of the United States of America 99, 13571-13576.

Tsun, Z.-Y., Bar-Peled, L., Chantranupong, L., Zoncu, R., Wang, T., Kim, C., Spooner, E., and Sabatini, D. M. (2013). The Folliculin Tumor Suppressor Is a GAP for the RagC/D GTPases That Signal Amino Acid Levels to mTORC1. Molecular cell 52, 495-505.

Woo, H. A., Bae, S. H., Park, S., and Rhee, S. G. (2009). Sestrin 2 Is Not a Reductase for Cysteine Sulfinic Acid of Peroxiredoxins. Antioxidants & Redox Signaling 11, 739-745.

Yuan, H.-X., Xiong, Y., and Guan, K.-L. (2013). Nutrient Sensing, Metabolism, and Cell Growth Control. Molecular cell 49, 379-387.

Zoncu, R., Bar-Peled, L., Efeyan, A., Wang, S., Sancak, Y., and Sabatini, D. M. (2011). mTORC1 Senses Lysosomal Amino Acids Through an Inside-Out Mechanism That Requires the Vacuolar H+-ATPase. Science Signaling 334, 678-683.

---

What is claimed is:

1. A method of identifying a test compound as an activator of mTORC1 activity comprising the steps of:
   a) providing a mixture comprising:
      (i) a first polypeptide comprising the amino acid sequence of Sestrin1 (SEQ ID NO:1), Sestrin2 (SEQ ID NO:2), Sestrin3 (SEQ ID NO:3), or a polypeptide having at least 90% sequence identity to any one of SEQ ID NOs:1-3 that retains the ability to bind GATOR2; and
      (ii) a second polypeptide or protein complex comprising the amino acid sequence of a GATOR2 complex (SEQ ID NOs:4-8), or a polypeptide or protein complex having at least 90% sequence identity to SEQ ID NOs:4-8 that retains the ability to bind to at least one of Sestrin1, Sestrin2 or Sestrin3,
   under conditions that allow the first polypeptide to associate with the second polypeptide or protein complex;
   b) incubating the mixture of a) with the test compound;
   c) determining whether the amount of the first polypeptide associated with the second polypeptide or protein complex is altered in the presence of the test compound as compared to either the absence of the test compound or the presence of a negative control, wherein if the amount of association is decreased the test compound is identified as an activator of mTORC1 activity.

2. The method of claim 1, wherein the first polypeptide comprises the amino acid sequence of Sestrin1 (SEQ ID NO:1), Sestrin2 (SEQ ID NO:2), Sestrin3 (SEQ ID NO:3), or SEQ ID NOs:9-11.

3. The method of claim 1, wherein the second polypeptide or protein complex comprises the amino acid sequence of a GATOR2 complex (SEQ ID NOs:4-8).

4. The method of claim 1, wherein the second polypeptide or protein complex comprises the amino acid sequence of WDR24 (SEQ ID NO:4).

5. The method of claim 1, wherein the mixture comprises a first polypeptide comprising the amino acid sequence of Sestrin1 (SEQ ID NO:1), Sestrin2 (SEQ ID NO:2), Sestrin3 (SEQ ID NO:3), or a polypeptide having at least 95% sequence identity to any one of SEQ ID NOs:1-3 that retains the ability to bind GATOR2; and a second polypeptide or protein complex comprising the amino acid sequence of a GATOR2 complex (SEQ ID NOs:4-8), or a polypeptide or protein complex having at least 95% sequence identity to SEQ ID NOs:4-8 that retains the ability to bind to at least one of Sestrin1, Sestrin2 or Sestrin3.

6. A method of identifying a test compound as an inhibitor of mTORC1 activity comprising the steps of:
   a) providing a mixture comprising:
      (i) a first polypeptide comprising the amino acid sequence of Sestrin1 (SEQ ID NO:1), Sestrin2 (SEQ ID NO:2), Sestrin3 (SEQ NO:3), or a polypeptide having at least 90% sequence identity to any one of SEQ ID NOs:1-3 that retains the ability to bind GATOR2, and
      (ii) a second polypeptide or protein complex comprising the amino acid sequence of a GATOR2 complex (SEQ ID NOs:4-8), or a polypeptide or protein complex having at least 90% sequence identity to SEQ ID NOs:4-8 that retains the ability to bind to at least one of Sestrin1, Sestrin2 or Sestrin3,
   under conditions that prevent the first polypeptide from associating with the second polypeptide or protein complex;
   b) incubating the mixture of a) with the test compound;
   c) determining whether the amount of the first polypeptide associated with the second polypeptide or protein complex is altered in the presence of the test compound as compared to either the absence of the test compound or the presence of a negative control, wherein if the amount of association is increased the test compound is identified as an inhibitor of mTORC1 activity.

7. The method of claim 6, wherein the conditions that prevent the first polypeptide from associating with the second polypeptide or protein complex comprises the presence of leucine.

8. The method of claim 6, wherein the first polypeptide comprises the amino acid sequence of Sestrin1 (SEQ ID NO:1), Sestrin2 (SEQ ID NO:2), Sestrin3 (SEQ ID NO:3), or SEQ ID NOs:9-11.

9. The method of claim 6, wherein the mixture comprises a first polypeptide comprising the amino acid sequence of Sestrin1 (SEQ ID NO:1), Sestrin2 (SEQ ID NO:2), Sestrin3 (SEQ ID NO:3), or a polypeptide having at least 95% sequence identity to any one of SEQ ID NOs:1-3 that retains the ability to bind GATOR2; and a second polypeptide or protein complex comprising the amino acid sequence of a GATOR2 complex (SEQ ID NOs:4-8), or a polypeptide or protein complex having at least 95% sequence identity to SEQ ID NOs:4-8 that retains the ability to bind to at least one of Sestrin1, Sestrin2 or Sestrin3.

10. A method of identifying a test compound as a modulator of mTORC1 by determining if the test compound can induce or increase the affinity of Sestrin1 or Sestrin2 for leucine comprising the steps of:
   a. providing a mixture comprising:
      i. polypeptide comprising the amino acid sequence of Sestrin1 (SEQ ID NO:1) or Sestrin2 (SEQ ID NO:2), or a polypeptide having at least 90% sequence identity to any one of SEQ ID NOS:1-2 that retains the ability to bind leucine; and
      ii. leucine; and
      iii. the test compound, under conditions that allow leucine to bind to the polypeptide; and
   b. determining whether the amount of leucine bound to the polypeptide associated is altered in the presence of the test compound as compared to either the absence of the test compound or the presence of a negative control, wherein if the amount of binding is decreased in the presence of test compound, the test compound is identified as an inhibitor of mTORC1 activity; and if the amount of binding is increased in the presence of the test compound, the test compound is identified as an activator of mTORC1 activity.

11. The method of claim 10, wherein the leucine is tagged with a detectable label.

12. The method of claim 11, wherein the leucine is tagged with a radiolabel.

* * * * *